(12) United States Patent
Perry

(10) Patent No.: US 11,129,566 B1
(45) Date of Patent: Sep. 28, 2021

(54) INSTRUMENT FOR MEASURING PRESSURE-INDUCED SENSORY THRESHOLD WITH NON-ELECTRICAL POWER ASSIST PIVOT MECHANISM

(71) Applicant: Anthony Gerald Perry, New Orleans, LA (US)

(72) Inventor: Anthony Gerald Perry, New Orleans, LA (US)

(73) Assignee: Anthony Perry, New Orleans, LA (US)

( * ) Notice: Subject to any disclaimer, the term of this patent is extended or adjusted under 35 U.S.C. 154(b) by 428 days.

(21) Appl. No.: 16/054,230

(22) Filed: Aug. 3, 2018

Related U.S. Application Data

(60) Provisional application No. 62/541,496, filed on Aug. 4, 2017.

(51) Int. Cl.
*A61B 5/00* (2006.01)

(52) U.S. Cl.
CPC .......... *A61B 5/4827* (2013.01); *A61B 5/0053* (2013.01); *A61B 5/4005* (2013.01); *A61B 5/0051* (2013.01); *A61B 5/4076* (2013.01); *A61B 5/6829* (2013.01)

(58) Field of Classification Search
None
See application file for complete search history.

(56) References Cited

U.S. PATENT DOCUMENTS

| | | | | | |
|---|---|---|---|---|---|
| 2,704,539 | A | * | 3/1955 | Fisher | A61B 5/441 600/557 |
| 3,933,148 | A | * | 1/1976 | Wyler | A61B 5/0053 600/557 |
| 4,313,446 | A | * | 2/1982 | Kanatani | A61B 5/4827 600/553 |
| 4,823,806 | A | * | 4/1989 | Bajada | A61H 39/08 600/557 |
| 4,964,412 | A | * | 10/1990 | Kelly | A61B 5/441 600/553 |
| 5,316,011 | A | * | 5/1994 | Weinstein | A61B 5/4827 600/557 |
| 5,492,132 | A | * | 2/1996 | Weinstein | A61B 5/4827 600/557 |
| 5,823,969 | A | * | 10/1998 | Christy | A61B 5/4824 600/557 |

(Continued)

*Primary Examiner* — Patrick Fernandes
*Assistant Examiner* — Benjamin S Melhus
(74) *Attorney, Agent, or Firm* — McGlew and Tuttle, P.C.

(57) ABSTRACT

An improved pressure sensory threshold testing instrument comprised of a filamentous testing element (132) mounted on a head member (102) that is pivotally attached to a handle member (100) with a nonelectrical power assist pivot mechanism. The power assist pivot mechanism aids in actively biasing the head member (102) into either an open, testing position or a closed, storage position. The power assist mechanism and geometry resist accidental opening that could expose and damage the filament. The design facilitates one-handed operation with no change in grasp needed throughout the whole process of retrieval, testing, and storage. This singular grasp allows for increased ease and efficiency of the testing procedure. The configuration speeds the testing process while protecting the filament more securely in an instrument that is portable in a pocket. The design also minimizes the potentially threatening appearance of this type of medical testing device.

20 Claims, 44 Drawing Sheets

(56) References Cited

U.S. PATENT DOCUMENTS

| | | | | |
|---|---|---|---|---|
| 6,113,551 A * | 9/2000 | Isaacs | .................. | A61B 5/0053 |
| | | | | 600/557 |
| D439,336 S * | 3/2001 | Najmi | .......................... | D19/902 |
| 6,196,976 B1 * | 3/2001 | Christy | ................ | A61B 5/0053 |
| | | | | 600/557 |
| 6,200,272 B1 * | 3/2001 | Linden | ................ | A61B 5/4824 |
| | | | | 600/557 |
| 6,234,976 B1 * | 5/2001 | Linden | ................ | A61B 5/4824 |
| | | | | 600/557 |
| 6,234,977 B1 * | 5/2001 | Christy | ................ | A61B 5/0053 |
| | | | | 600/557 |
| D489,455 S * | 5/2004 | Mork | .......................... | D24/142 |
| 7,678,064 B2 * | 3/2010 | Kuban | ................. | A61B 5/4824 |
| | | | | 600/557 |
| 8,512,259 B2 * | 8/2013 | Christy | ................ | A61B 5/4047 |
| | | | | 600/557 |
| 8,864,679 B2 * | 10/2014 | Krotoski | .............. | A61B 5/4827 |
| | | | | 600/557 |
| 2008/0097236 A1 * | 4/2008 | Kuban | ................. | A61B 5/4824 |
| | | | | 600/557 |
| 2009/0105606 A1 * | 4/2009 | Bell Krotoski | ...... | A61B 5/4827 |
| | | | | 600/557 |
| 2010/0056949 A1 * | 3/2010 | Christy | ................ | A61B 5/0053 |
| | | | | 600/557 |
| 2011/0288434 A1 * | 11/2011 | Christy | ................ | A61B 5/4824 |
| | | | | 600/557 |
| 2011/0288435 A1 * | 11/2011 | Christy | ................ | A61B 5/4824 |
| | | | | 600/557 |
| 2014/0005568 A1 * | 1/2014 | O'Brien | ............... | A61B 5/4827 |
| | | | | 600/557 |

* cited by examiner

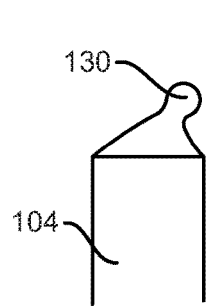 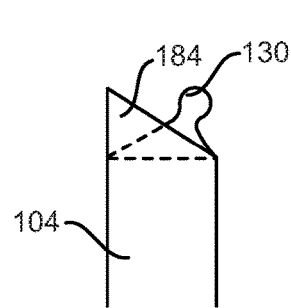 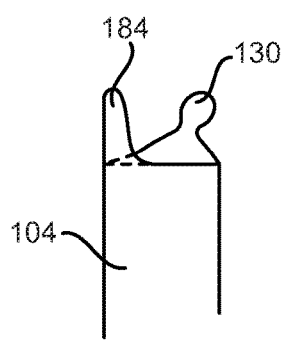 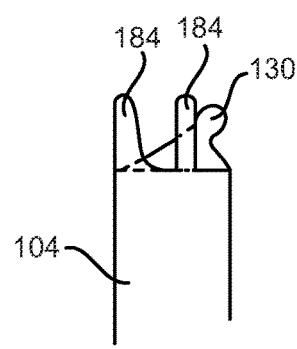
FIG. 14A   FIG. 14B   FIG. 14C   FIG. 14D
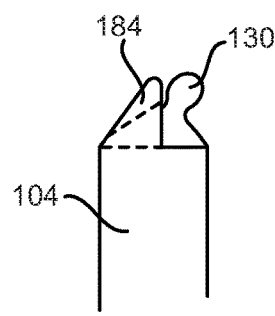 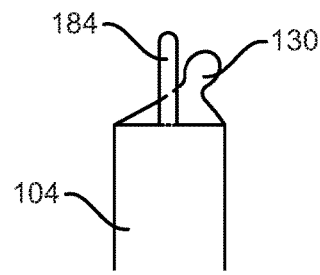 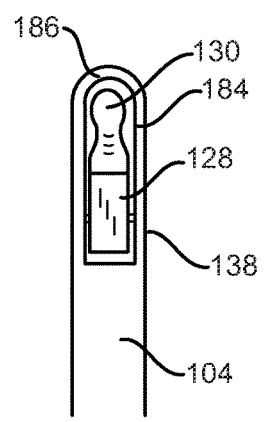
FIG. 14E   FIG. 14F   FIG. 14G

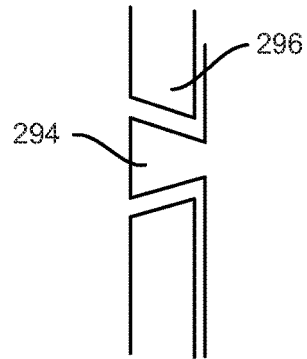
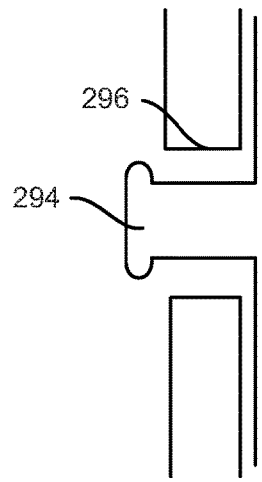
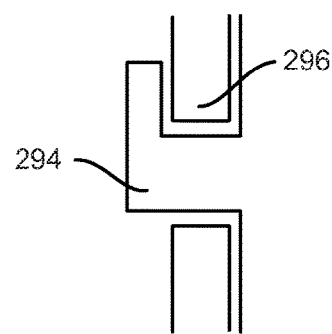
FIG. 25A          FIG. 25B          FIG. 25C
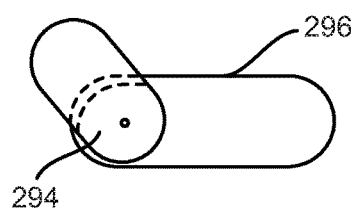
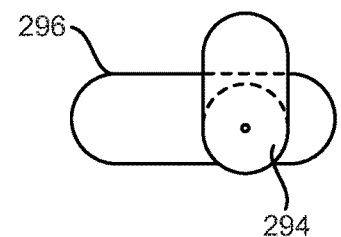
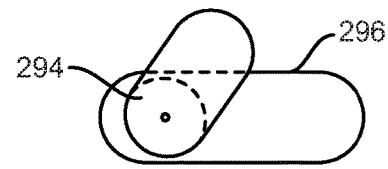
FIG. 25D          FIG. 25E          FIG. 25F

INSTRUMENT FOR MEASURING PRESSURE-INDUCED SENSORY THRESHOLD WITH NON-ELECTRICAL POWER ASSIST PIVOT MECHANISM

CROSS REFERENCE TO RELATED APPLICATIONS

This application claims the benefit of priority under 35 U.S.C. § 119 of U.S. Provisional Application 62/541,496 filed Aug. 4, 2017, the entire contents of which are incorporated herein by reference.

FIELD OF THE INVENTION

The invention relates to medical testing devices, and more particularly relates to sensory testing devices.

BACKGROUND OF THE INVENTION

A standard medical test to quantitate a patient's ability to feel utilizes a device commonly referred to as a Semmes-Weinstein monofilament. This device utilizes a resilient/elastic monofilament made of a known material (nylon) with a known length (38 mm) and known diameter. These known parameters give a known force under which the length of the filament will buckle when an axial load is applied. This device delivers a reliable/reproducible pressure to the testing surface (usually skin) of the patient. The testing procedure relies on the sense of touch alone with no visual or audible cues to the patient. The examiner/operator touches the tip of the Semmes-Weinstein monofilament very lightly with no impact to the patient's skin. Pressure is slowly applied until the filament buckles and then the tip of the filament is gently withdrawn from contact with the patient's skin. The patient communicates each time the filament is felt. Filaments of different parameters may be used to deliver different known degrees of pressure. The filaments usually vary only in diameter with the length and material of composition remaining constant. A pressure sensory threshold may be determined for a specific body location by determining the lightest pressure sensed by the patient at that location. Normal values for different areas and surfaces of the body have been established from previous research testing. The pressure sensory threshold may be used to determine presence or absence of sensory deficit, degree of deficit, location of deficit and to monitor course (improving or worsening) of the deficit. This test is very commonly used in current medical practice, especially to detect and quantitate sensory deficit in diabetic feet. Many medical practitioners perform this test on many patients each day. The test can be time consuming. Testing instructions are first explained to the patient. Fears of testing often need to be addressed since many patients visually confuse the appearance of the filament with a sharp needle despite the verbal explanation. This further adds time to the testing procedure. Multiple sights on the skin are tested and multiple different strength filaments may be used to quantitate sensory thresholds. Anything to make this process quicker and more efficient, yet accurate, will be welcomed by a busy medical practitioner.

The touch from the filament must be applied in a specific reproducible manner which requires concentration, dexterity and finesse on the examiner's part. The contact with the patient's skin must be perpendicular to eliminate angular bending forces on the filament and should have the most minimal impact force possible. Once contact is achieved, the filament is gradually loaded with axial pressure from the operator, until the filament buckles. Once the filament buckles, it is lifted off the skin surface in a perpendicular manner. No shear force may be applied to the skin during any portion of testing, or the brushing sensation of the filament may be detected instead of the pressure sensation, thus giving a false result. The filament should contact the skin for approximately 1.5 seconds during the testing process. This process is repeated at each test site. Examinations usually are performed at multiple sites bilaterally which contributes to the time-consuming nature of this test.

A filament that is damaged, kinked, or worn will yield to buckling prematurely giving a false test result and therefore should not be used.

Attempts have been made to mount the filament for sensory testing in many ways. None of these allow a complete one-handed process from retrieval of the device from a breast pocket, testing on a subject/patient, and return to storage in the breast pocket, all with no need to change grasp on the testing device any time throughout the entire process. Previous attempts have not addressed the threatening appearance of the device that is often visually interpreted by the patient to be a sharp needle that is being jabbed at them. Other attempts also have not addressed the need to lock the testing filament in a protected storage position in a manner that can quickly and easily be locked and unlocked with single hand operation and no need for change in grasp. The other attempts also have not addressed a visually pleasing artistic presentation that adds interest to the device. The other attempts also do not provide a power assist mechanism that automatically positions the testing filament into the precise position/alignment needed for accurate testing and secure storage. The other attempts also do not add the interest of a power assist mechanism and the pleasing tactile sensation of operating the power assist mechanism. The previous attempts do not provide a completely one hand operated device that is as quick to use, as secure in breast pocket storage, as accurate in filament positioning, as nonthreatening in appearance, or as interesting to operate.

SUMMARY OF THE INVENTION

According to the invention in one embodiment, a sensory testing device is provided comprising a head member, a filament connected to the head member, a handle member, a pivot connection between the handle member and the head member for pivoting movement of the head member about an axis relative to the handle member between a storage position and a testing position; and a biasing device, which is also referred to as a biasing means or power assist device. The biasing device biases the head member toward the storage position (a stable position) with the head member adjacent to the storage position and biases the head member toward the testing position (a stable position) with the head member adjacent to the testing position. The biasing means is such that a force (a biasing force) must be overcome for the pivoting movement of the head member in relation to the handle member about the axis of the pivoting connection out of the storage position toward the testing position. This biasing force is overcome with an external activating force or actuating force. The biasing means is such that a force (the biasing force) must be overcome for the pivoting movement of the head member in relation to the handle member about the axis of the pivoting connection out of the testing position toward the storage position. This biasing force is overcome with an external activating force or actuating force. The biasing force has two directions of action with the biasing device exerting the biasing force to bias assist or bias retard a forward or backward motion whereby in an initial storage angular range of pivot motion from the storage position, the biasing force biases the head member toward the storage position and in a further angular range of pivot motion from the storage position, the biasing force biases the head member toward the testing position and in an initial testing angular range of pivot motion from the testing position, the biasing force biases the head member toward the testing position and in a further angular range of pivot motion from the testing position, the biasing force biases the head member toward the storage position. The device is bi-stable, namely with a stable storage position and a stable testing position.

The biasing force acts in the two directions, or the testing biasing force acts in the direction toward the testing position and the storage biasing force acts in the direction toward the storage position. The testing biasing force and the storage biasing force may have force values and ranges of application that may be preset as desired. For example, the range of the testing biasing force, biasing the head member toward the testing position, may be 45 degrees or more of the approximately 90 degrees range of pivoting movement of the head member. The range of the storage biasing force, biasing the head member toward the storage position, may be less than 45 degrees of the total, approximately 90 degrees, range of pivoting movement of the head member. The two biasing forces may overlap or there may be essentially no biasing force in an angular range between the range applying the testing biasing force and the storage biasing force. Also, the testing biasing force and the storage biasing force may be stronger or may only be applied close to or adjacent to the testing position and the storage position respectively.

In accordance with one embodiment, a pressure sensory threshold testing instrument comprises a filamentous testing element protruding from a head member that is pivotally affixed to a handle member, A non-electrical power assist mechanism aids in quick and accurate positioning of the head member between two biased positions of open testing position (deployed position) and closed storage position (not deployed/retracted position). The device can be fully retrieved, operated, and stored quickly with just the use of one hand and a single unchanging grip/grasp.

Accordingly, several advantages of one or more aspects are as follows: to provide a sensory filament testing instrument that is rapid to use with complete single hand operation, that is constructed with a non-electrical power assist mechanism that securely and accurately positions the head member, that is relatively nonthreatening in appearance to reduce the time and effort to reassure the patient of the painless nature of the test, that is visually pleasing and interesting, such as with sculpted components, that is relatively inexpensive and simple to manufacture and assemble, that is relatively resistant to debris accumulation in crevices to maintain a clean aseptic appearance expected of medical equipment, that has a head member and/or filament tip that can be used independently from the handle member, that is portable and able to be transported in a pocket without damage to the testing filament, that is able to actively autocorrect and reposition the filament back to the protected storage position if accidently exposed from this protected position, that is enjoyable to use with a power assist mechanism that is interesting and pleasing to operate (like a fidget device), that is able to be locked in a closed storage position, that is able to double as a scraping device to test the Babinski reflex, that is relatively small, thin, and streamlined to fit easily in crowded pockets or storage containers/pencil cups, that can be used with minimal explanation and reassurance to the patient, that is durable and reliable (has durable and reliable power sources such as springs and magnets which are unlikely to fatigue and fail), that is amendable to multiple artistic designs that add visual interest, that has components that relative to one another can be made of materials that differ in composition, texture, appearance, color, etc., that is operational with little concentration needed to deploy and store the filament, that is able to be labeled and or color coded to signify filaments of different testing forces/strengths, that is not likely to accidently open and damage the filament while stored in a breast pocket when the operator leans forward even while unlocked and ready for immediate use (due to the activation lever angling away from the body and the power assist force to favor the closed storage position), that is configured with surfaces for sharp and dull sensory testing, that has a handle member with cutouts or cross sectional shape that allows tactile reference for alignment, that has exchangeable filament tip units and/or head member mounted filament tip units that can be used for accurate testing independent of mounting on a head member or handle member, that has a testing filament aligned perpendicular to the handle member so the patient/testing subject does not confuse the instrument with a hypodermic needle axially mounted on a syringe. Other advantages of one or more aspects will be apparent from a consideration of the drawings and ensuing description.

BRIEF DESCRIPTION OF THE DRAWINGS

In the drawings:

FIGS. 14A to 14G show various views of various schematic configurations for a guard for activation lever;

FIGS. 25A to 25F show various views of peg and slot variations;

DESCRIPTION OF THE PREFERRED EMBODIMENTS

Figure 1:
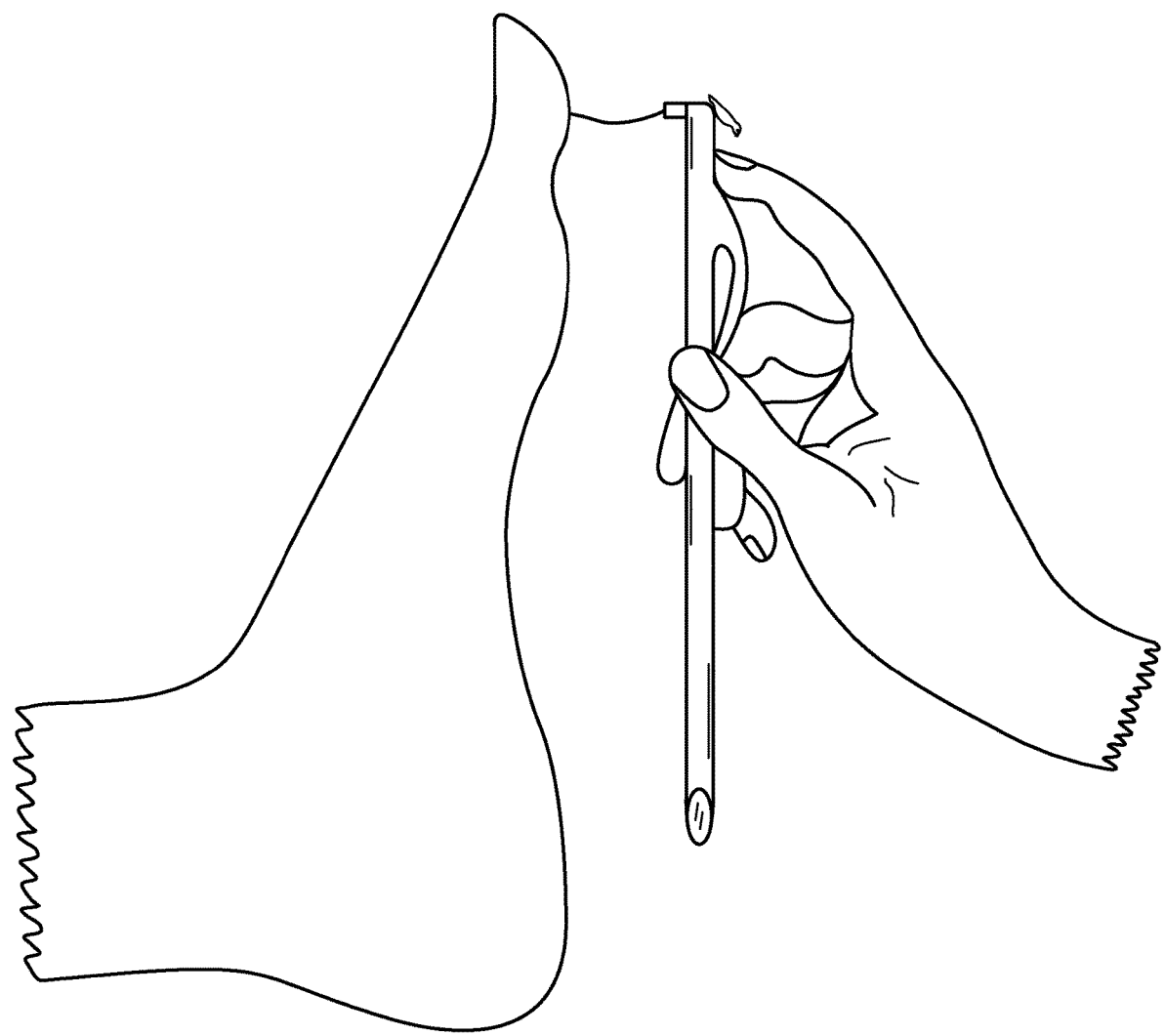
FIG. 1 shows a first embodiment in testing use.

In the drawings, closely related figures have the same number but different alphabetical suffixes. Orientation terms will refer to the embodiment in closed, storage position.

FIG. 1 shows the overall appearance of a first embodiment in open, testing position as it is used to test the sensation of a body surface.

Figure 2:
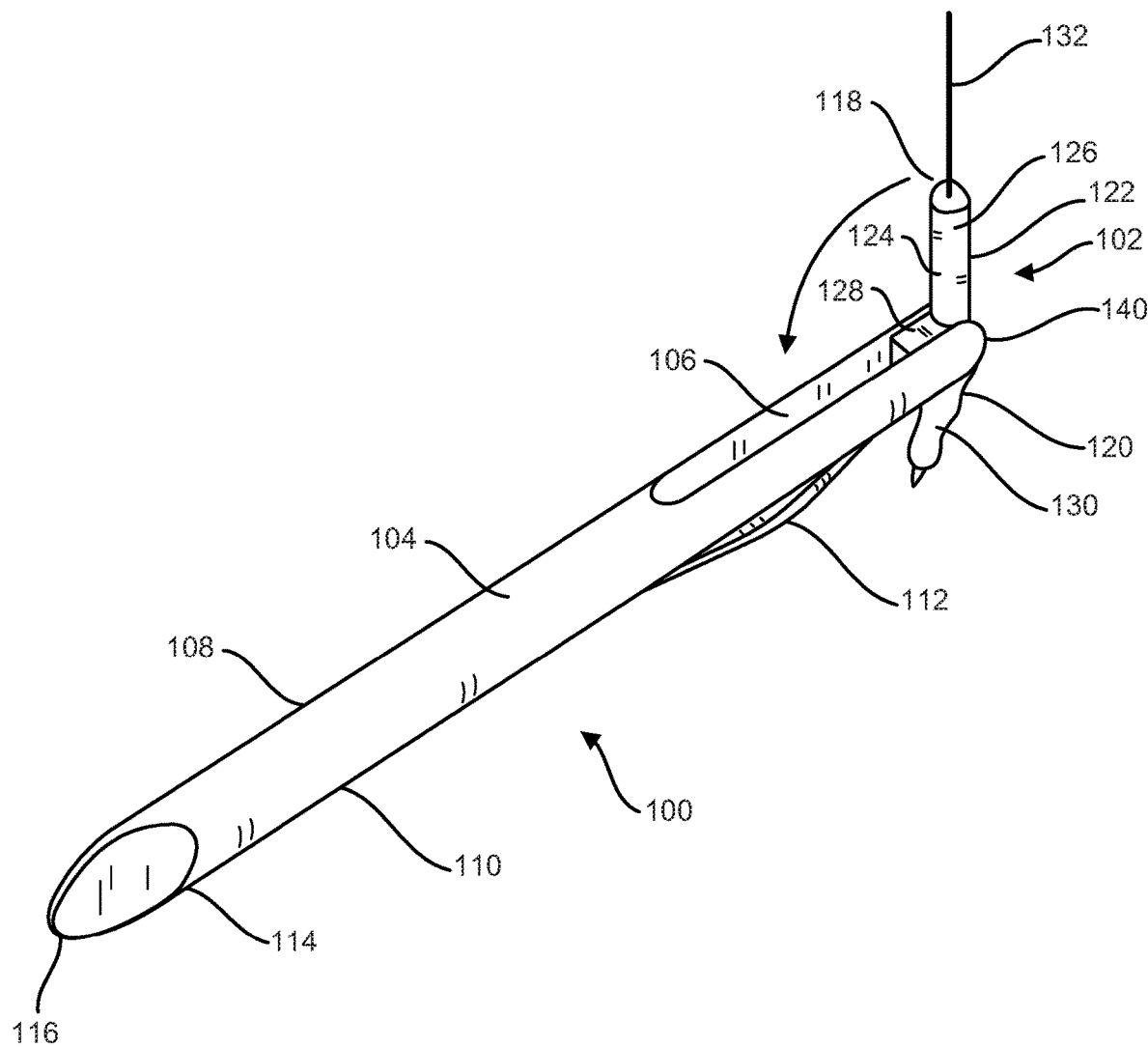
FIG. 2 shows a ventral left lateral perspective view of the first embodiment with the head member pivoted into open, testing position.
Figure 3:
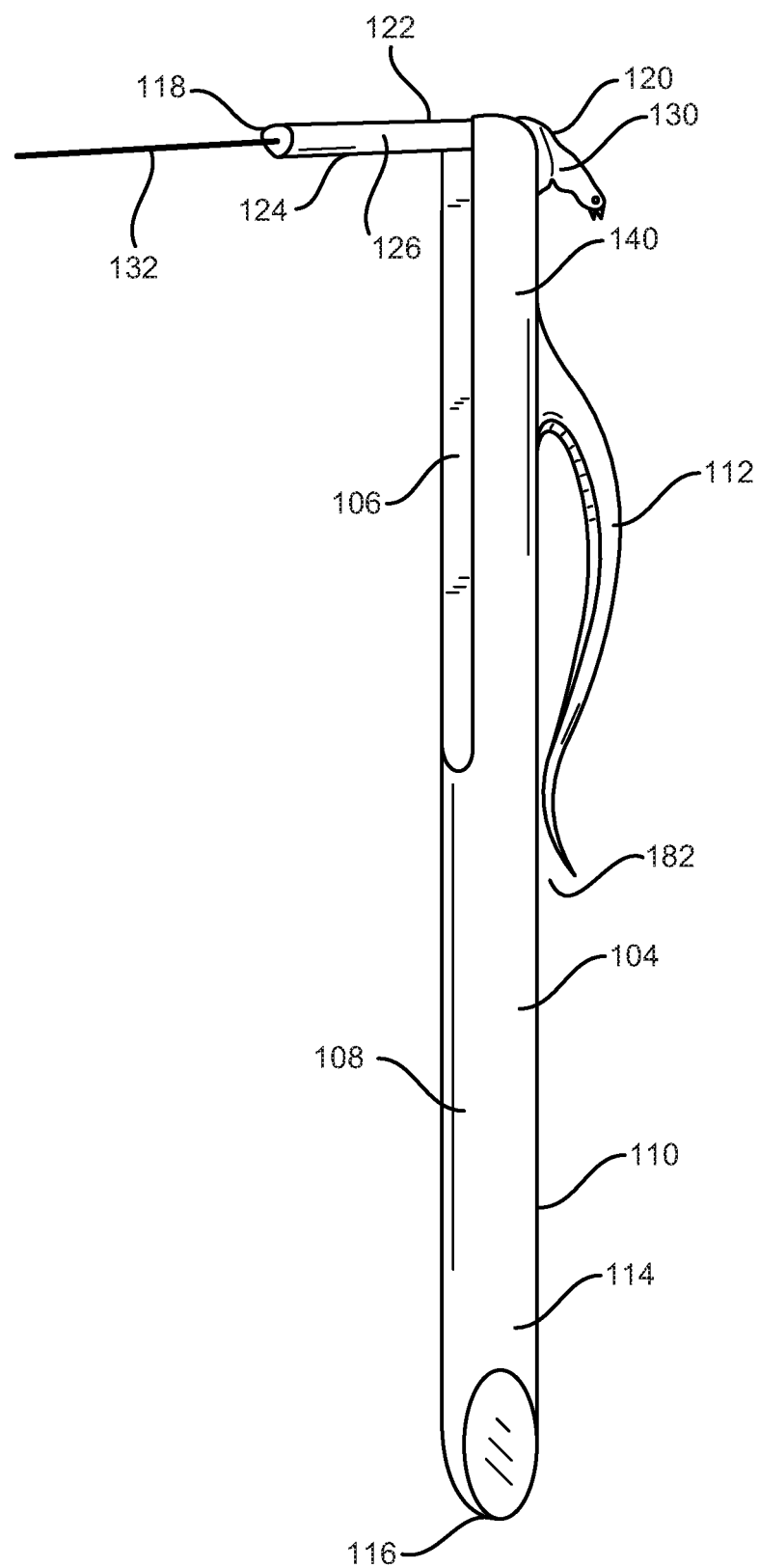
FIG. 3. shows a left lateral perspective view of the first embodiment in open, testing position.
Figure 32:
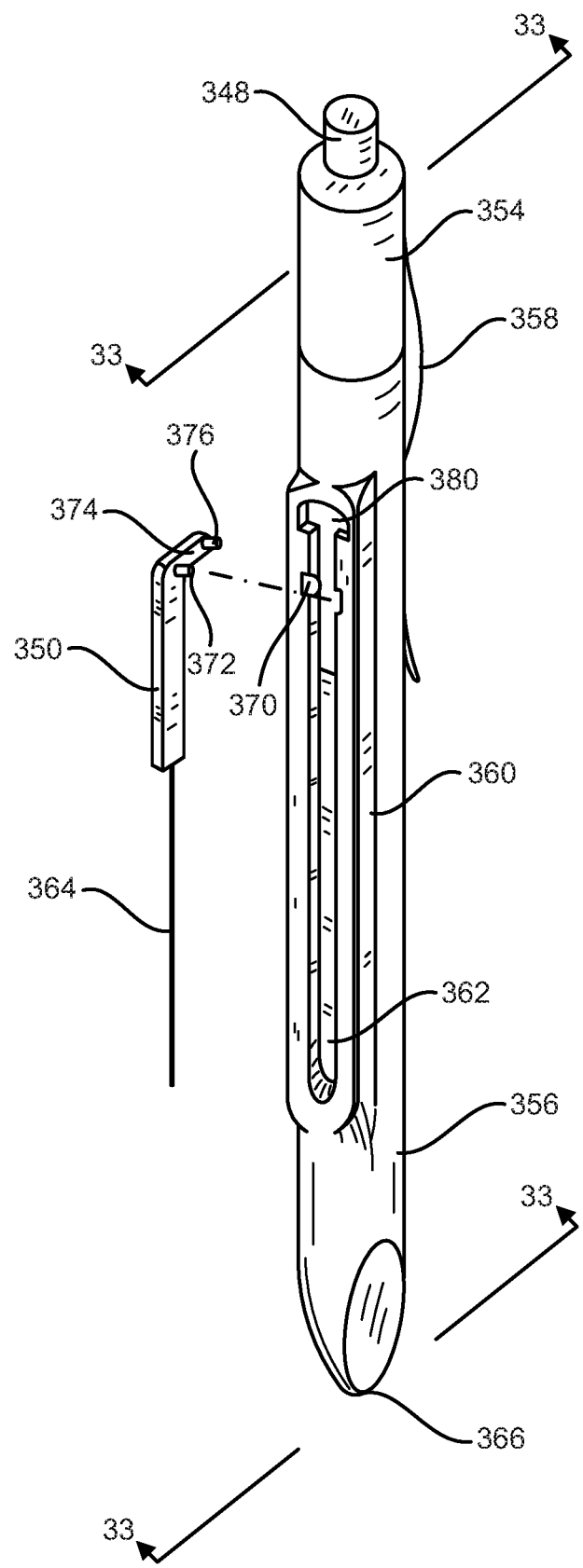
FIG. 32 shows a partially exploded ventral lateral perspective view of a seventh embodiment in closed, storage position (with filament arm exploded)

FIG. 2 is a ventral lateral perspective view of the first embodiment in open, testing position. The embodiment is composed of a handle member 100 and a pivotally attached head member 102. An elongated body 104 of the handle member 100 has an elongated channel 106 on a ventral, belly surface 108 toward a distal end 140 of the handle member 100. A channel lip 360 as shown in FIG. 32 is a variation. FIG. 3 is a lateral perspective view that shows a dorsal, back surface 110 of the handle member 100 that has a pocket clip 112 which is similar to (like) one on a retractable ballpoint pen. At a proximal end 114 of the handle member 100, there is a tapered beveled scrape tip 116.

The head member 102 is oriented with a proximal end 118, a distal end 120, a ventral, belly surface 122, and a dorsal, back surface 124. The head member 102 (also shown in isolated views in FIGS. 8A and 8B) comprises a filament arm 126, toward the proximal end 118 and a head body 128 which is seen more clearly in FIG. 4. The head body 128 has an activation lever 130 that protrudes distally and may be angled dorsally. The filament arm 126 receives a functional tip in the form of a sensory testing filament 132 that protrudes longitudinally relatively in line with the filament arm 126. Various other functional tips such as sharp probe, temperature probe, vibratory probe, tool tips, etc. may be used at the proximal end of the head member 118 in place of the testing filament 132.

The axial cross section of the handle member 100 in the first embodiment is shown as oval, however, it can have different cross-sectional shapes such as square, round, rectangular, triangular, etc. The handle member 100 may also have tactile features such as flattened portions, ridges or grooves to aid the operator in aligning the handle member 100 with no visual cues. The beveled scrape tip 116 at the proximal end 114 of the handle member 100 in the first embodiment has a beveled relatively flat surface on each side of the handle member 100 leaving a laterally flattened tip that is relatively blunt and of significant strength to scrape a skin surface without yielding. This beveled scrape tip 116 at the proximal end 114 of the handle member 100 can have other functional and nonfunctional geometries such as a sculpted configuration, rounded, pointed, squared off (axially flattened), wobble tip, flared wide for a broad flat base to stand upright, resilient conductive tip for operation of touch screen devices, etc.

The pocket clip 112, as seen more clearly in FIG. 3, can be molded or machined as one with the body of the handle member 104 near the distal end 120 of the handle member 100. This pocket clip 112 can also be a separate piece of material such as spring steel, plastic, etc. that clips on, slides on, or attaches in some secure manner to serve as a pocket clip on a retractable writing pen. The channel 106 for filament storage in the first embodiment (seen more clearly in FIGS. 3 and 5A) is long enough and deep enough for the filament 132 to rest in without protruding, while the head member 102 is in the closed, storage position as seen in FIG. 5A.

Figure 9A:
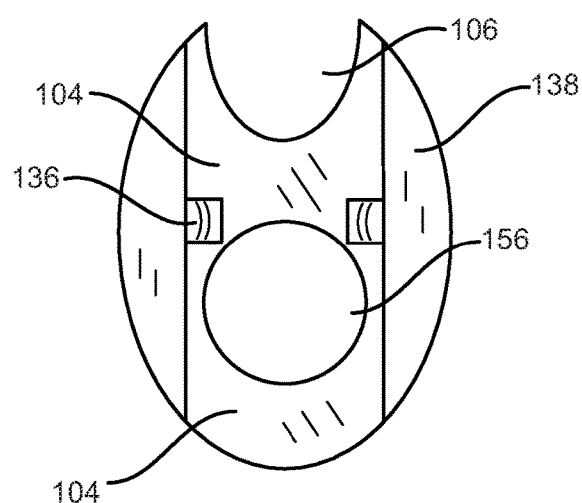
FIG. 9A shows a distal view of the handle member with the head member, piston, pocket clip, and spring removed.
Figure 9B:
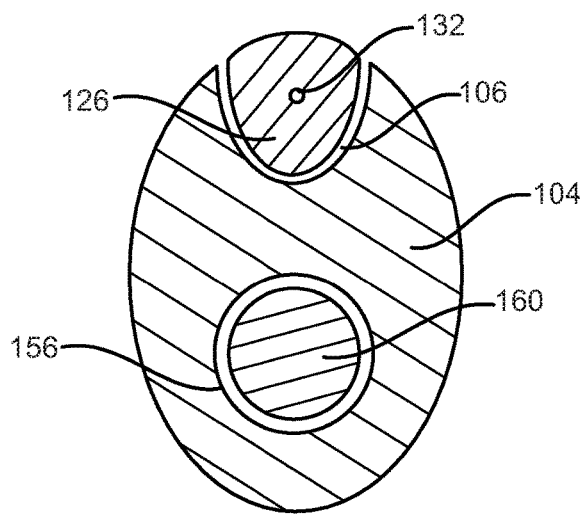
FIG. 9B shows a sectional view of the embodiment of FIG. 6 taken at the sectioning plane indicated by section lines 9B-9B with head member and piston in place.

FIGS. 9A and 9B show the axial cross section of the elongated channel 106 for filament storage in the first embodiment is relatively "u" shaped with a rounded deep surface to prevent sharp recessed corners where dirt and debris can accumulate. FIGS. 5A and 5B show the sagittal cross section of the channel 106 for filament storage, which at the proximal end is also rounded for the same reason. The axial cross section of the channel 106 can have other variations such as triangular/"V" shaped, square, rectangular, etc. The shape of the channel 106 cross section securely mates with the shape of the back, dorsal surface/side of the filament arm 126 for a stable, secure fit while the head member 102 is positioned in the closed storage position.

Figure 4:
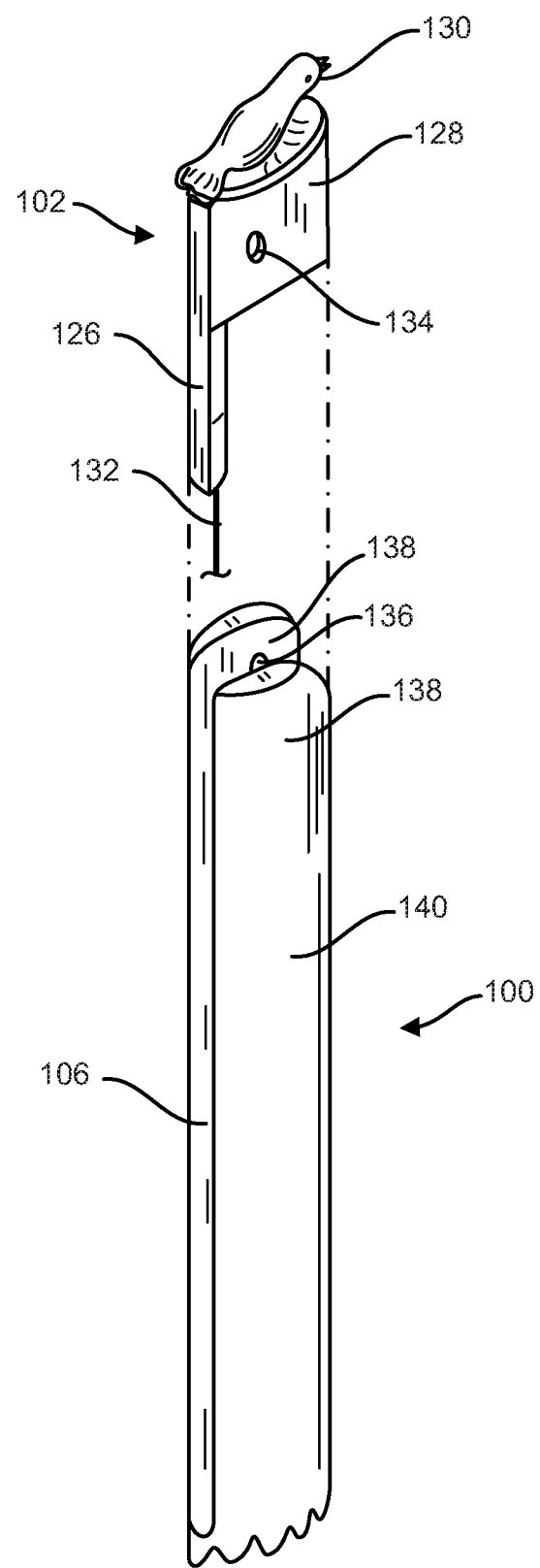
FIG. 4 shows an exploded left lateral perspective partial view of the first embodiment with the head member in closed, storage position.

FIG. 3 shows the first embodiment from a left lateral perspective view with the head member 102 pivoted 90 degrees upon the handle member 100 into the open, testing position. However, this pivot can be less or greater than 90 degrees. FIG. 3 more clearly shows the profile of the pocket clip 112 and the activation lever 130. FIG. 4 shows a ventral lateral exploded view of the first embodiment. This view more clearly shows the relationship of the filament arm 126 extending proximally from the ventral edge of the body 128 of head member 102. FIG. 4 also more clearly shows the relationship of the activation lever 130 extending from the distal edge of the body 128 of head member 102.

Figure 5A:
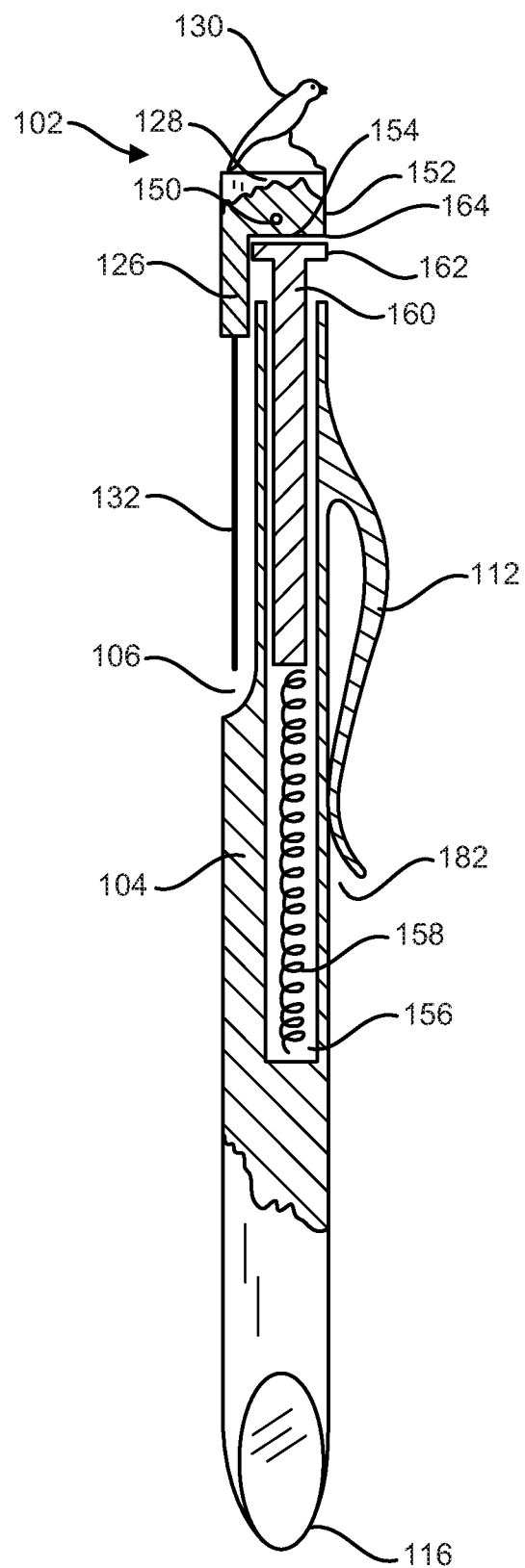
FIG. 5A shows a lateral partial middle sectional view of the first embodiment in closed, storage position.
Figure 5B:
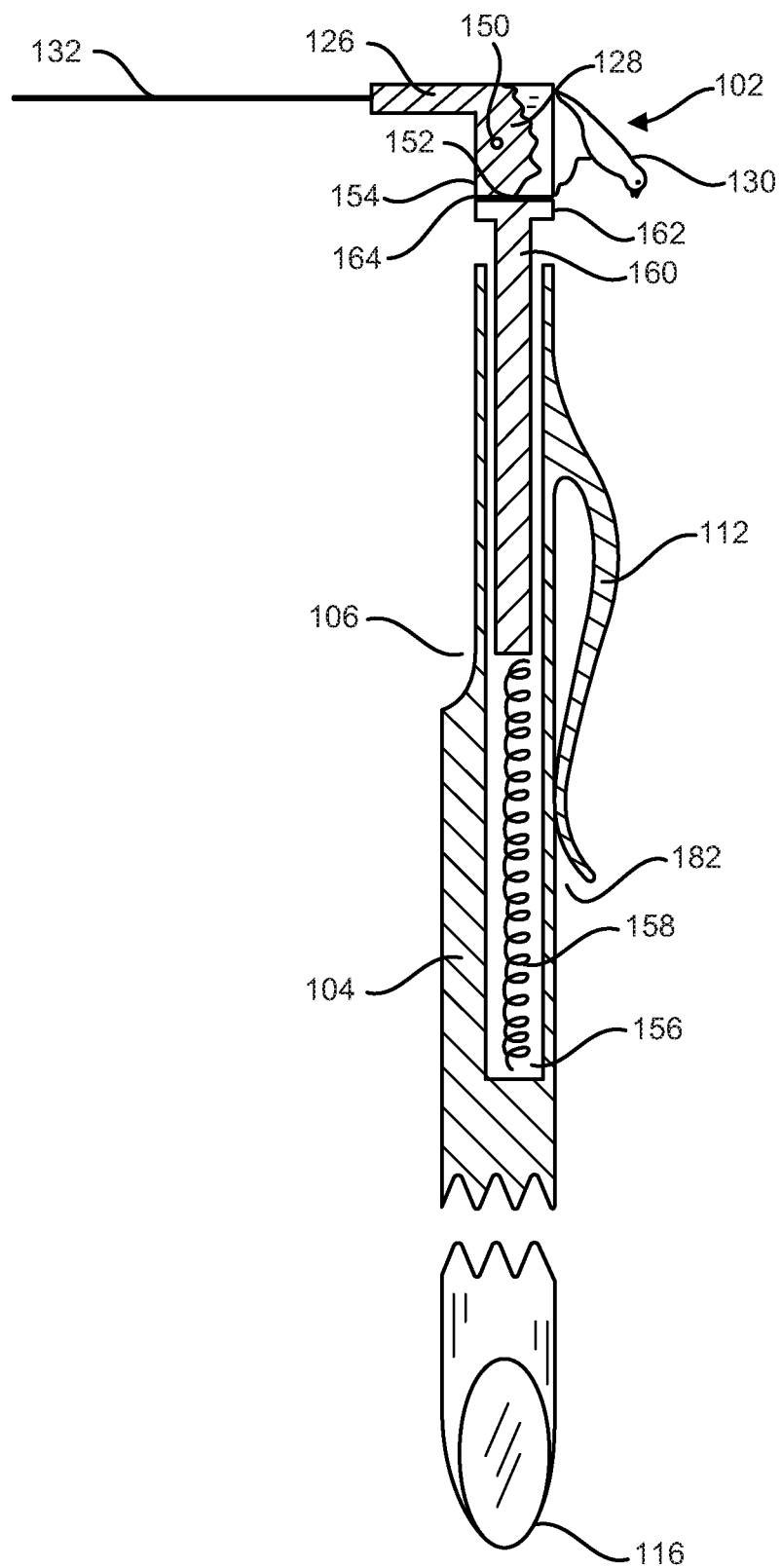
FIG. 5B shows a lateral partial middle sectional view of the first embodiment in open, testing position.

FIG. 5A more clearly shows a lateral profile view of the head member 102 with its component parts. In this embodiment, the activation lever 130 extends at a distal dorsal angle relative to the length of the handle member 100 while the head member 102 is in the closed storage position. The angle and structure of the activation level 130 allows it to protrude from the dorsal surface of the handle member when the head member 102 is pivoted into the open, testing position as seen in FIG. 5B.

FIG. 4 also shows an axle mounting hole/bore 134 on the head member 102. The axle mounting hole/bore 134 mates with an axle peg 136 that protrudes from a deep surface of a retaining flange, arm, upright 138 portion of the distal end 140 of handle member 100. The mating of the axle mounting hole 134 and the axle peg 136 is secure enough to hold the head member 102 securely fastened to, and aligned with the handle member 100, yet loose enough to allow pivoting/rotary motion around the axle. In the first embodiment, the head member 102 snap fits onto the axle pegs 136 via the axle mounting holes 134 on the body 128 of the head member 102.

Figure 7A:
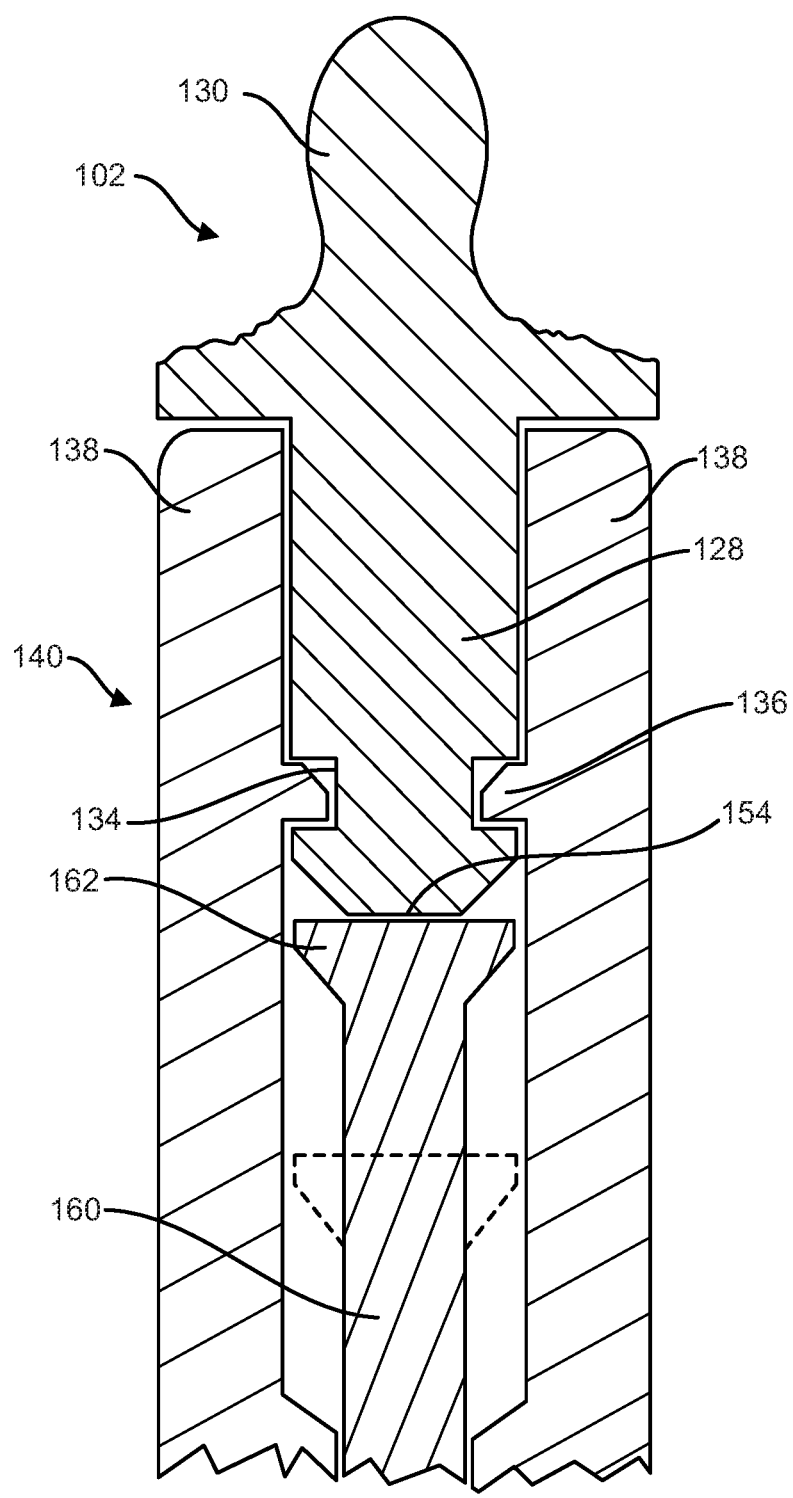
FIG. 7A shows a dorsal sectional partial view of the embodiment of FIG. 6 taken at the sectioning plane indicated by section lines 7A-7A of FIG. 6 (in closed, storage position)

The retaining flanges 138 in the first embodiment are elastically resilient enough to allow adequate spread of the retaining flanges 138 to allow the width/distance between the tips of the axle pegs 136 to be expanded to allow snap fit insertion of the body 128 of head member 102 via the axle mounting holes 134 onto the axle pegs 136. The axle pegs 136 can have a beveled tip as seen in FIG. 7A to aid in ease of assembly. The portion of the body 128 of head member 102 that is proximal to the axle mounting holes 134 may also be beveled as shown in FIG. 7A to also aid in ease of assembly.

Figure 7B:
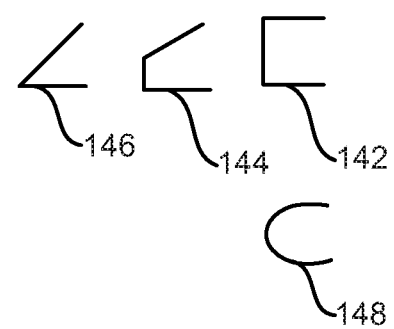
FIG. 7B shows various profiles of axle pegs.

Different geometries of a/the tip shape of the axle peg 136 are shown in FIG. 7B. These geometries may include but are not limited to a flat/squared tip 142, partial bevel tip 144, bevel to point tip 146, rounded tip 148, etc. These different geometries of the tip shape may ease assembly, resist disassembly, improve security and stability of fit of the head member 102 upon the handle member 100, and change the level of friction and resistance of the pivoting movement of the head member 102 upon the handle member 100.

A variation of this embodiment may a have a solid axle, singular through both sides or one on each side, that passes through the retaining flanges 138 and the body of head member 128 through a pivot moment 150 of head member 102 as shown in FIG. 5A. A variation of this embodiment could also have the axle pegs 136 protruding from the body 128 of head member 102 and the axle mounting holes 134 in the retaining flanges 138.

FIG. 5A shows the first embodiment in lateral sectional view while in closed storage position. The retaining flange 138 seen in FIG. 4 has been fully cut away in the FIG. 5A view. This sectional view reveals a plate/disc/radial cam and spring-loaded piston/plunger follower assembly. The body 128 of head member 102 has two functional surfaces, a testing position contact surface 152 of head member 102 and a storage position contact surface 154 of head member 102 that form the cam portion of the assembly. The pivot moment of head member 150 is marked in the first embodiment in the body of head member 128 at a point proximal to mid length of the testing position contact surface 152 of head member 102 and ventral to mid length of storage position contact surface 154 of head member 102.

This position of the pivot moment 150 favors the head member 102 to pivot into the closed storage position. The pivot moment of head piece 150 can be placed anywhere within the limits of the body 128 of head member 102 depending on the desired bias to favor pivoting into the closed position or open position. FIGS. 5A and 5B also shows a spring-loaded piston assembly deep within the body 104 of handle member consisting of a piston cylinder 156, a compression spring 158, a piston/plunger body 160 and a contact table 162 of piston. The piston cylinder 156 is sized tight enough to hold the piston/plunger body 160 stable and aligned during linear motion within the piston cylinder 156, yet loose enough to allow the piston/plunger body 160 to slide freely in a linear fashion within the piston cylinder 156.

The piston/plunger body 110 is long enough to allow maintained stable alignment within the piston cylinder 156 throughout the intended functional range of excursion. In this first embodiment, the piston cylinder 160 is parallel to the long axis of the handle member 100, but it may be angled in any direction that fits within the confines of the body 104 of handle member 100. The storage position contact surface 154 sits flush against the contact table 162 of piston while the first embodiment is in closed storage position, but the two surfaces are not attached. Similarly, the testing position contact surface 152 sits flush against the contact table 162 of the piston while the first embodiment is in the open, testing position, but the two surfaces are not attached.

During the pivoting motion of the head member 102, a bias corner 164 is created on the head body 128, where the storage position contact surface 154 meets the testing position contact surface 152. The bias corner 164 slides against the contact table 162. These two contact surfaces in this first embodiment can be made of durable material such as, but not limited to plastic, metal, etc. that will resist abrasive and compressive wear, yet allow relatively low friction as the bias corner 164 slides against the contact table 162.

FIG. 5A shows the first embodiment with the head member 102 pivoted into closed, storage position while FIG. 5B shows the first embodiment with the head member 102 pivoted into open, testing position. The compression spring 158 is more compressed in open, testing position FIG. 5B than in closed, storage position FIG. 5A due to the position of the pivot moment 150 of head member 102. This difference in spring compression favors the bias of closed, storage position. This favored bias helps to error on the side of filament protection in the closed, storage position.

Figure 6:
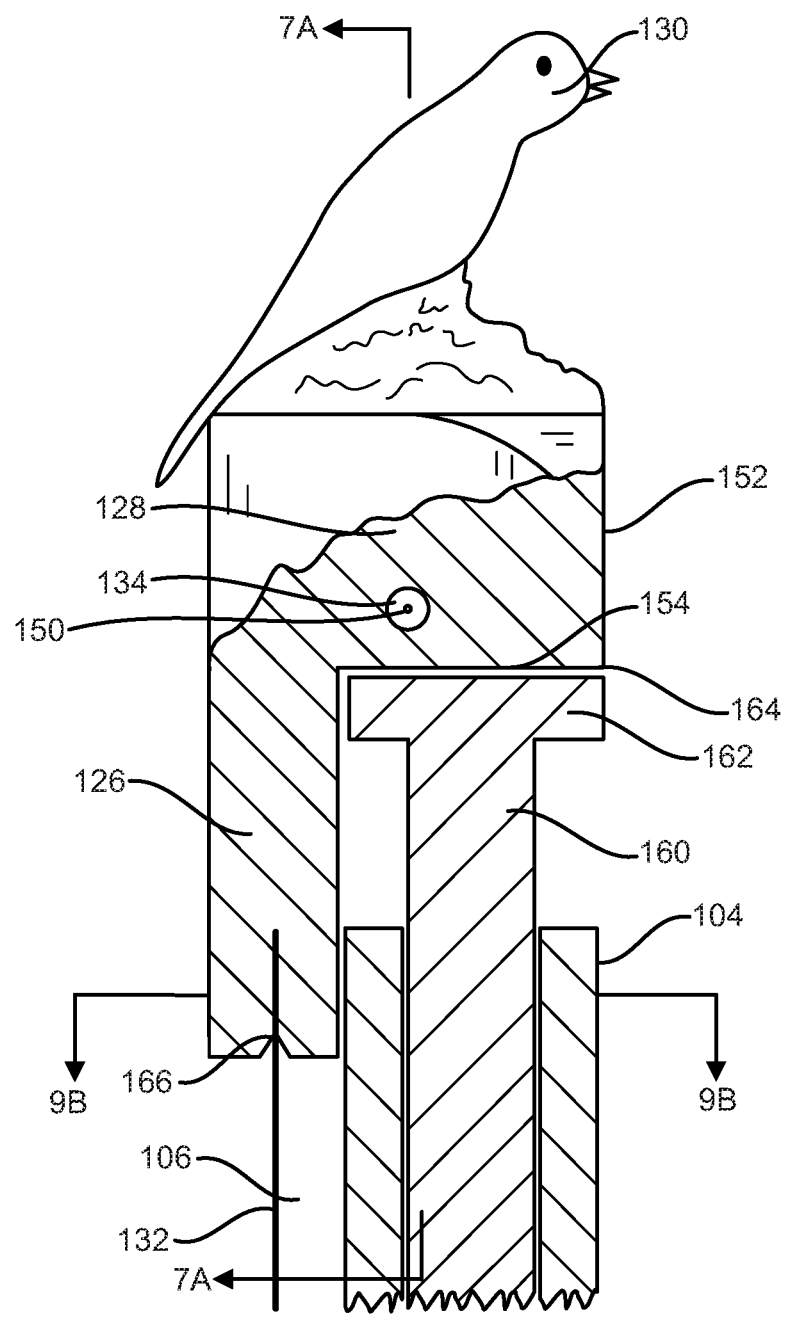
FIG. 6 shows a lateral partial middle sectional view of the distal end of the first embodiment in closed, storage position.

FIG. 6 shows a close-up lateral partial cutaway/sectional view of the distal portion of the first embodiment in closed, storage position. Note that there is clearance between the proximal surface of the contact table 162 of piston and the distal opposing surface of the body 104 of handle member 100, This clearance allows room for full functional excursion of the piston body 160. The filament 132 is mounted in a filament mounting bore 166 of similar diameter to hold the filament fixed and aligned parallel to the long axis of the filament arm 126. The bore 166 may not be needed if the filament arm 126 is molded onto the filament 132 during manufacture. In the first embodiment, the filament 132 is mounted centrally in a proximal tip of the filament arm 126, but it may be mounted in other positions such as more dorsally on the tip of the filament arm 126 so the filament 132 will sit deeper in the channel 106 for increased protection.

This deeper position may offer more protection of the filament 132 while in closed, storage position. In the first embodiment, the filament mounting bore 166 has a beveled opening to aid in ease of assembly but absence of the bevel is also an option.

FIG. 7A is a dorsal sectional view of the embodiment of FIG. 6 taken at the sectioning plane indicated by section lines 7A-7A. The contact table 162 of piston is shown in phantom/dotted lines to sit more proximal when the embodiment is in open, testing position.

Figure 10:
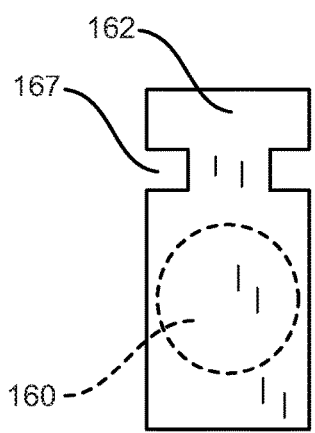
FIG. 10 shows a distal view of the contact table of the piston with the piston body in phantom beneath the contact table.

FIG. 7A also shows a bevel in the proximal surface of the contact table 162 of piston at the sectional plane of the axle peg 136. This bevel can help the contact table 162 of piston pass the protrusion of the axle pegs 136 during assembly. FIG. 10 shows a distal plan view of the contact table 162 with a cutout 167 that is optional to allow passage around the axle pegs 136 upon assembly. The cutouts 167 could have a tight fit to allow the contact table 162 of piston to snap past axle pegs 136 upon assembly. This moderate resistance to pass the axle pegs 136 will prevent projectile spring-loaded ejection of the piston body 160 when the head member 102 is removed during disassembly.

FIG. 7B shows various profiles of axle pegs 142, 144, 146, 148 which may favor ease of assembly, stability, and or ease of rotation to varying degrees.

Figures 8A, 8B:
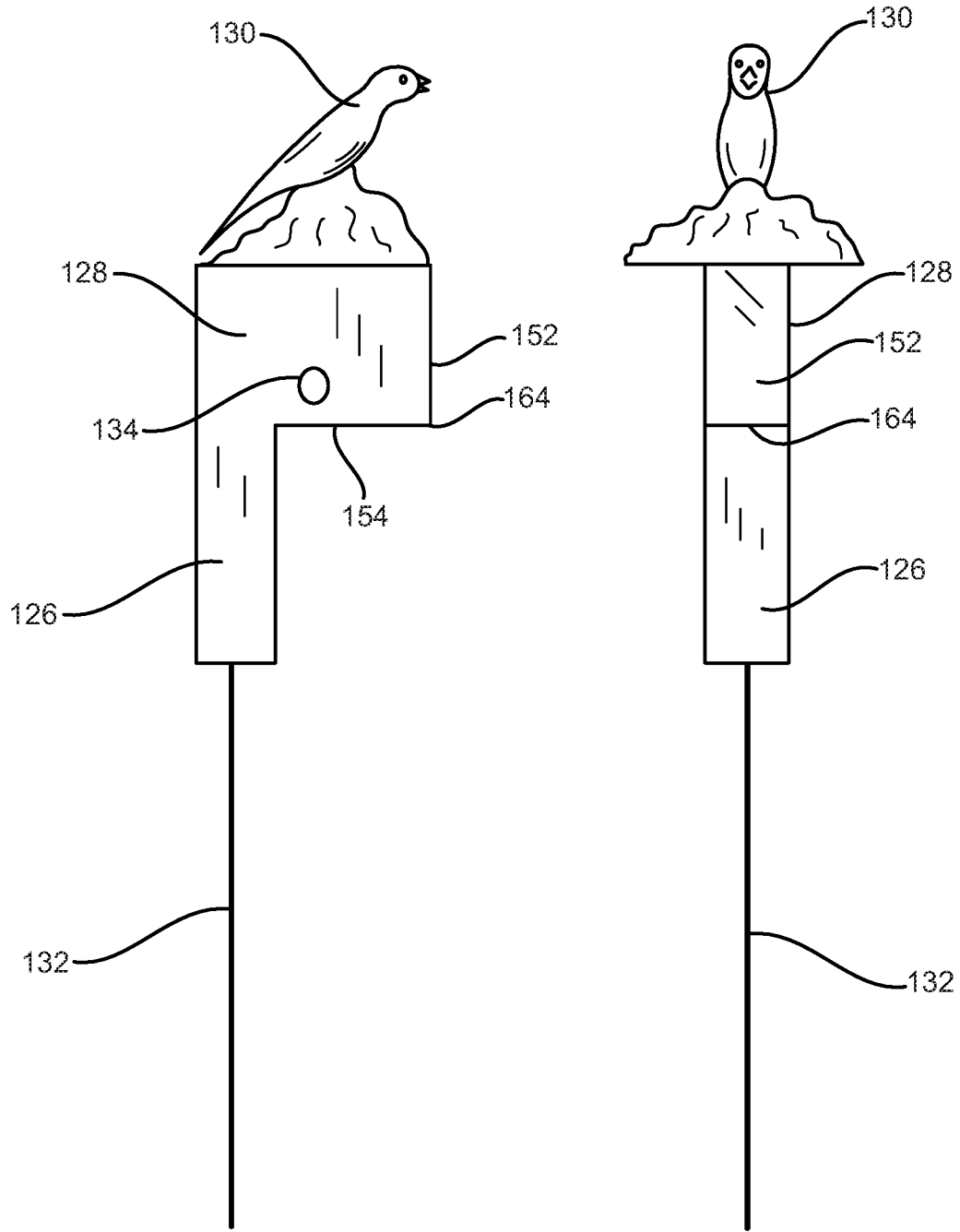
FIG. 8A shows the head member of the first embodiment in lateral view.
FIG. 8B shows the head member of the first embodiment in dorsal view.

FIG. 8A shows a lateral view and FIG. 8B shows a dorsal view of the head member 102. The head body 128 has a width that fits between the retaining flanges 138 of the distal end 140 of handle member 100 when pivoted into any functional position. The activation lever 130 may be wider than the head body 128 as seen in this first embodiment, as long as it does not interfere with the required range of pivoting motion of the head member 102 relative to the handle member 100. The activation lever 130 that is wider than the gap between the two retaining flanges 138 may be useful to prevent over excursion during pivoting by abutting against the retaining flanges 138 at each end of the functional range of pivot motion. The filament arm 126 may be of various shapes and lengths. A filament arm 126 is not necessary, and the filament 132 may be mounted protruding directly from the closed, storage state proximal surface of the body 128 of head member 102, as long as the filament 132 rests without distortion in the channel 106 when in closed, storage position.

The filament arm 126 in the first embodiment is long enough to abut against the deep surface of the channel 106 when in closed, storage position. This length prevents over excursion when pivoting the head member 102 into closed, storage position.

FIG. 9A is a distal view of the handle member 100 with the head member 102, piston body 160, spring 158, and pocket clip 112 removed. In this first embodiment, the relatively oval cross section of the body of handle member 104 and relative confluency of the retaining flanges 138 with the rest of the handle member 100 can be appreciated. Also, the relative position of the piston cylinder 156, the axle pegs 136, and the channel 106 can be appreciated. Shapes, configurations, and positions of these features may vary from this first embodiment.

FIG. 9B shows a sectional view of the embodiment of FIG. 6 taken at the sectioning plane indicated by section lines 9B-9B with the head member 102 and piston body 160 in place. In this embodiment, the filament arm 126 on its closed, storage state ventral surface is confluent with the oval cross section of the body of handle member 104. In this embodiment, the closed, storage state dorsal side of the filament arm 126 mates closely and securely with the contour of the channel 106. The piston body 160 has a stable fit in the cylinder 156.

FIG. 10 is a distal view of the contact table 162 of piston and the profile of the piston body 160 is represented in dotted lines/phantom beneath the contact table of piston 162. This view shows the cutouts 167 in the contact table 162 of piston to clear the axle pegs 136 during assembly of the piston body 160 into the cylinder 156. Similar cutouts can be made in the profile of the piston body 160 if a larger diameter piston body is desired. The cutouts in the contact table 162 could have a size that snap fits past the axle pegs 136 upon assembly. This snap fit feature can prevent spring-loaded ejection of the piston 160 when the head member is removed/detached.

Figure 11:
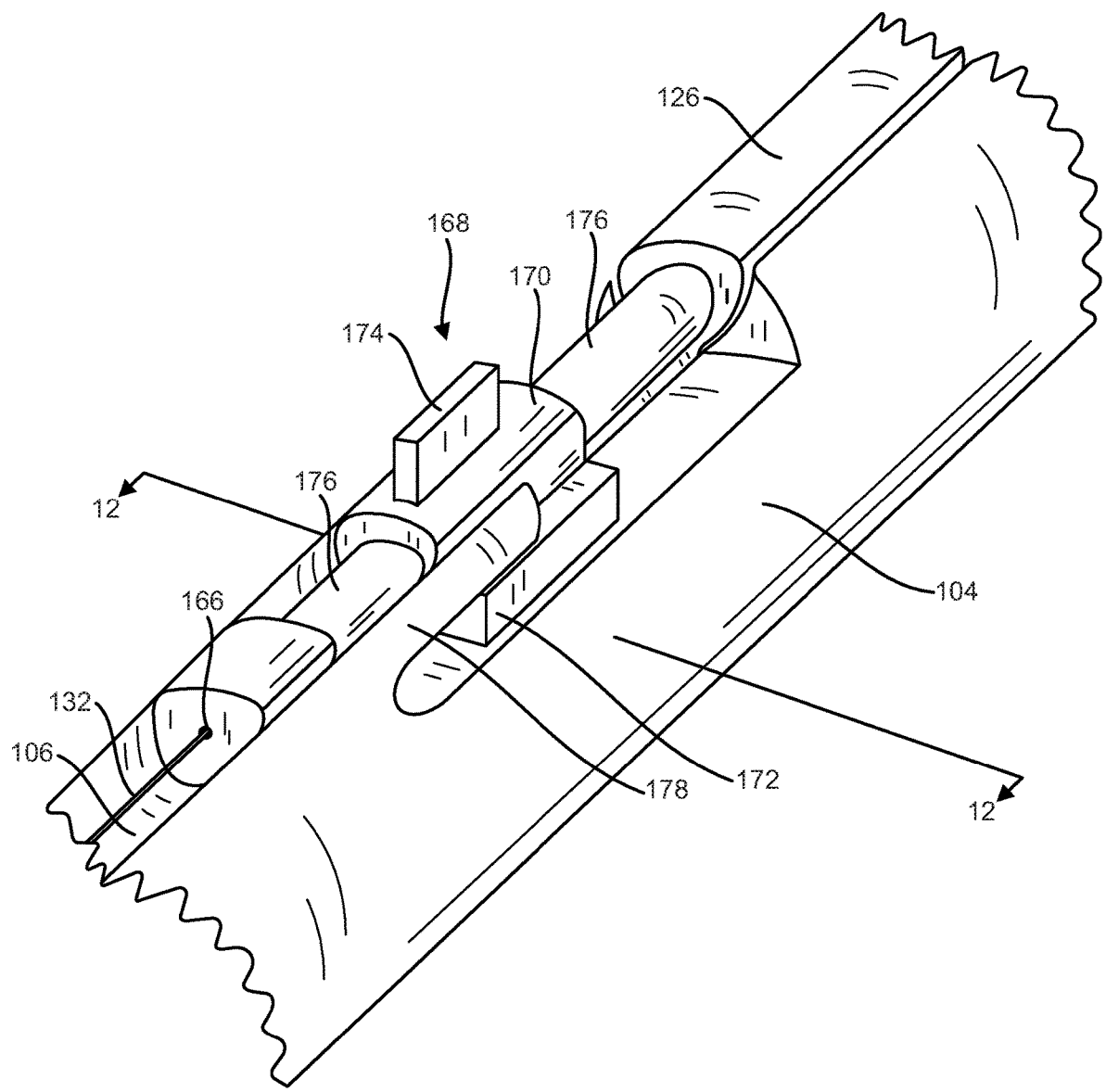
FIG. 11 shows a ventral lateral perspective partial view of the first embodiment with a filament arm locking mechanism partially engaged.

FIG. 11 shows a left lateral ventral partial perspective view of a variation of the first embodiment. This view includes the body 104 of handle member 100, the filament arm 126, and the filament 132 while in closed, storage position. In this variation of the first embodiment there is a locking slider 168 to secure the filament in closed, storage position. This locked position of the locking slider will protect the filament 132 from damage that could occur if the head member 102 were to unintentionally pivot the filament 132 out of the protective channel 106, such as could occur during transport in a pants pocket.

The locking slider 168 is composed of a slider body 170, a pair of slider locking flanges 172 which extend laterally from both sides of the slider body 170, and a slider finger tab/projection 174 extending from the closed, storage state ventral surface of the slider body 170. The filament arm 126 has a narrowed section somewhere approximately mid-length that serves as a slider shaft 176. The slider body 170 mates with the slider shaft 176. The mating should be secure to prevent unintentional detachment yet allow the slider body 170 to be slid into position to any desired location along the length of the slider shaft 176. The protrusion of the slider finger tab 174 allows for easy one finger operation to position the locking slider 168 along the length of the slider shaft 176 into the desired locked or unlocked position.

The mating of the slider body 170 and the slider shaft 176 should have an appropriate amount of friction to allow one finger positioning of the slider body 170 along the length of the slider shaft 176. The amount of friction between these two components also should be great enough for the slider body 168 to maintain the desired position upon the length of the slider shaft when forces less than one finger operation strength are applied. In this first embodiment of the variation, the slider body 170 clips onto the slider shaft 176 and the slider body 170 maintains some compression against the slider shaft 176. This degree of compression helps to maintain the desired friction between the two mating surfaces. The degree of compression depends on the friction coefficient between the materials of the two mating surfaces. The material of the slider body 170 must also maintain its elasticity with repeated use to maintain the compression and resulting friction against the slider shaft 176.

Materials such as, but not limited to, ABS plastic, other plastics, metals, etc. may be used.

The body 104 of handle member 100 in this variation has a body locking flange 178 formed into the side walls of the channel 106. The body locking flange 178 is positioned and shaped where the slider locking flanges 172 may slide into position beneath the body locking flanges 178 while the head member 102 is positioned in the closed, storage position. While the slider locking flanges 172 are positioned beneath the body locking flanges 178, the head member 102 may not be pivoted from the closed, storage position.

Figure 12:
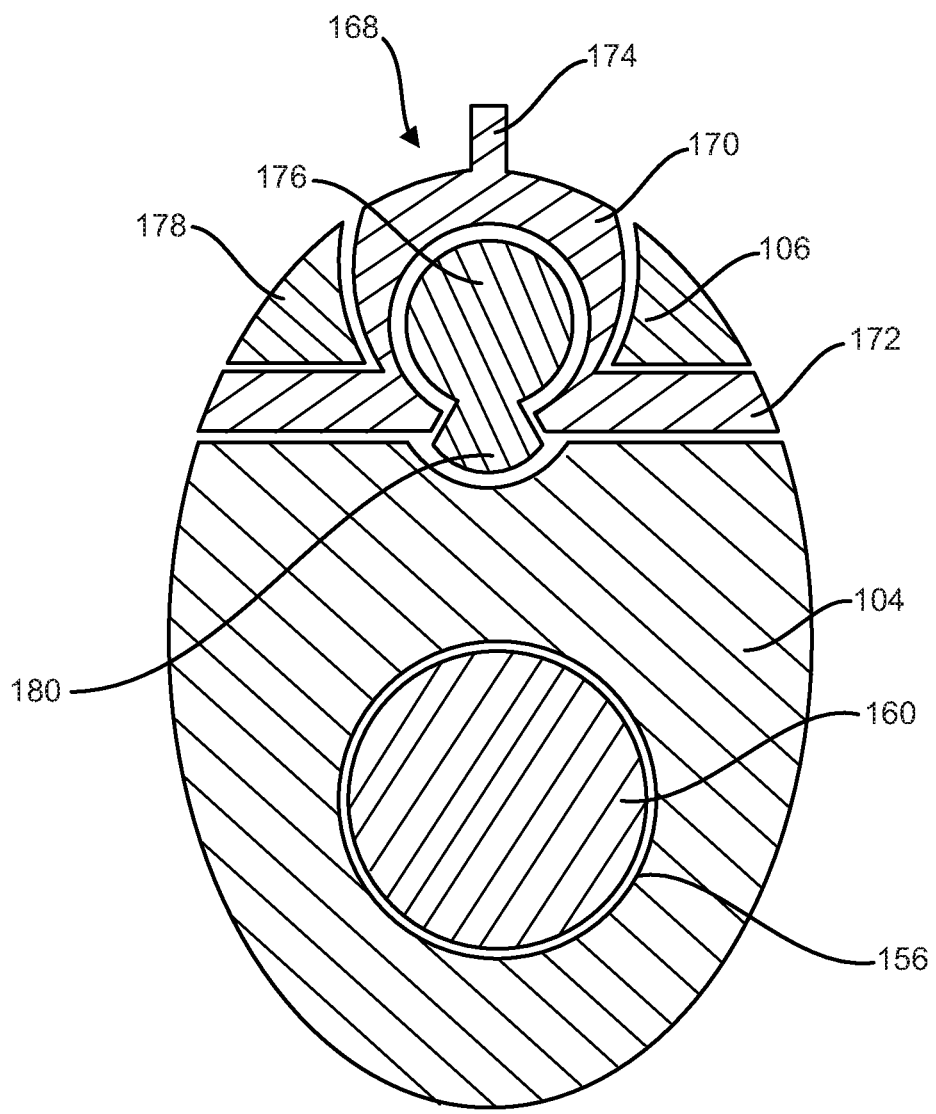
FIG. 12 shows a sectional view of the embodiment of FIG. 11 taken at the sectioning plane indicated by section lines 12-12.

When the slider locking flanges 172 are positioned out completely from beneath the body locking flanges 178, the head member 102 may be pivoted relative to the handle member 100, FIG. 12 shows a sectional view of the variation of the embodiment in FIG. 11 taken at the sectioning plane indicated by section lines 12-12 of FIG. 11 with the head member 102 in closed, storage position and the locking slider 168 positioned partially in locked position, with the slider locking flanges 172 positioned beneath the body locking flanges 178. In this locking variation of the first embodiment, the slider shaft 176 has a deep/closed, storage state dorsal ridge 180, for added strength through the relatively narrowed and weakened slider shaft 176 segment of the filament arm 126.

The slider body 170 in this embodiment of the locking variation is relatively "C" shaped with the opening facing deep/closed, storage state dorsal. This shape allows the slider body 170 to securely clip onto the slider shaft 176 for ease of assembly. In this embodiment of the locking variation, the slider finger tab 174 and slider locking flanges 172 are relatively rectangular while the closed, storage state ventral surface of the slider body 170 is confluent with the contour of the ventral surfaces of the body 104 of handle member. These shapes and contours may vary. The locking slider 168 in whole or in part may even be a sculpted yet functional form.

The pocket clip 112 (FIGS. 3, 5A, 5B) is a slightly flexible resilient flange similar in structure and function to a pocket clip on a modern retractable ball point writing pen. The pocket clip 112 protrudes from the dorsal surface of the body 104 of handle member 100. The pocket clip 112 in this embodiment differs slightly from that of an average pen in two ways. The pocket clip 112 may be longer to allow significant variation in depth of storage in the pocket. This allows for operator-controlled variation in the amount of the embodiment that protrudes from the pocket which can affect ease of grasp from the pocket. The other difference is the larger width of a gap 182 between the proximal tip of the pocket clip 112 and the body 104 of handle member 100. This increased gap 182 clearance allows the pocket clip 112 to more easily capture the lip of the pocket with less attention needed, during storage of the embodiment back into the pocket. The pocket clip 112 may also be a free piece that attaches or clips to the body 104 of handle member at an operator determined level to customize the protrusion of the embodiment from the pocket.

In the first embodiment, the activation lever 130 is a shaped configuration form with the head rising distally and dorsally. The dorsal position of the pocket clip 112 leaves the bird sculpted activation lever 130 facing outward away from the body of the operator when clipped in the pocket.

Figure 13A:
FIGS. 13A to 13L show examples of variations in geometry and sculpting of activation levers.
Figure 13B:
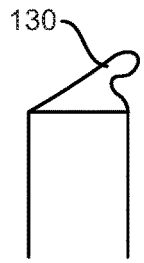
Figure 13C:
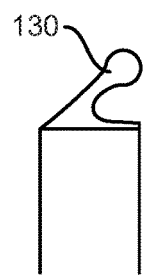
Figure 13D:
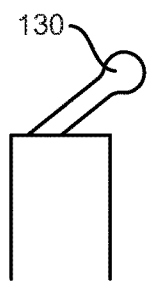
Figure 13E:
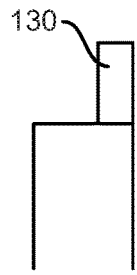
Figure 13F:
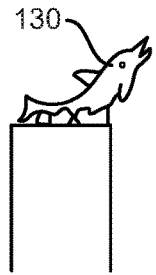
Figure 13G:
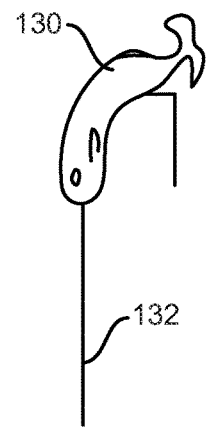
Figure 13H:
Figure 13I:
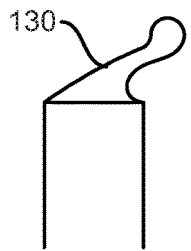
Figure 13J:
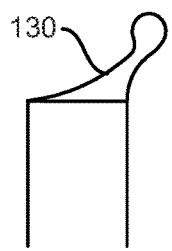
Figures 13K, 13L:
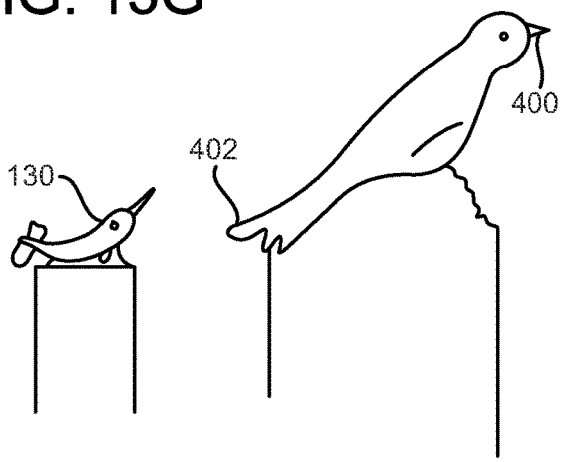

FIGS. 13A-13L show lateral views of examples of variations in geometry and sculpting of the activation lever 130 in the first embodiment. An infinite number of options exist. FIG. 13L shows a variation with a sharp/pointed tipped protrusion 400 on one end and a dull/blunt tipped protrusion 402 on the other end for testing a patient's sharp versus dull sensory perception FIGS. 14B-14G show schematic variations of a guard 184 for activation lever 130 in the first embodiment. FIG. 14A through FIG. 14F show left lateral views while FIG. 14G shows a dorsal view. FIG. 14A shows a schematic example of a geometric variation of the activation lever 130 without a guard 184 that will remain consistent relative to guard 184 variations depicted in FIG. 14B through FIG. 14G. The guard 184 for the activation lever 130 relatively protects the activation lever 130 from unintentional pivoting force while in closed, storage position.

The guards 184 for activation lever 130 may be distal extensions of the retaining flanges 138 that maintain a gap between the two retaining flanges 138. This gap allows room/space for the head member 102 to pivot freely. FIG. 14F (lateral view) and FIG. 14G (dorsal view) show a variation where the guard 184 of the activation lever 130 has a bridge/connection 186 that spans the gap between the retaining flanges 138 yet does not interfere with the pivoting motion of the head member 102.

Figure 15A:
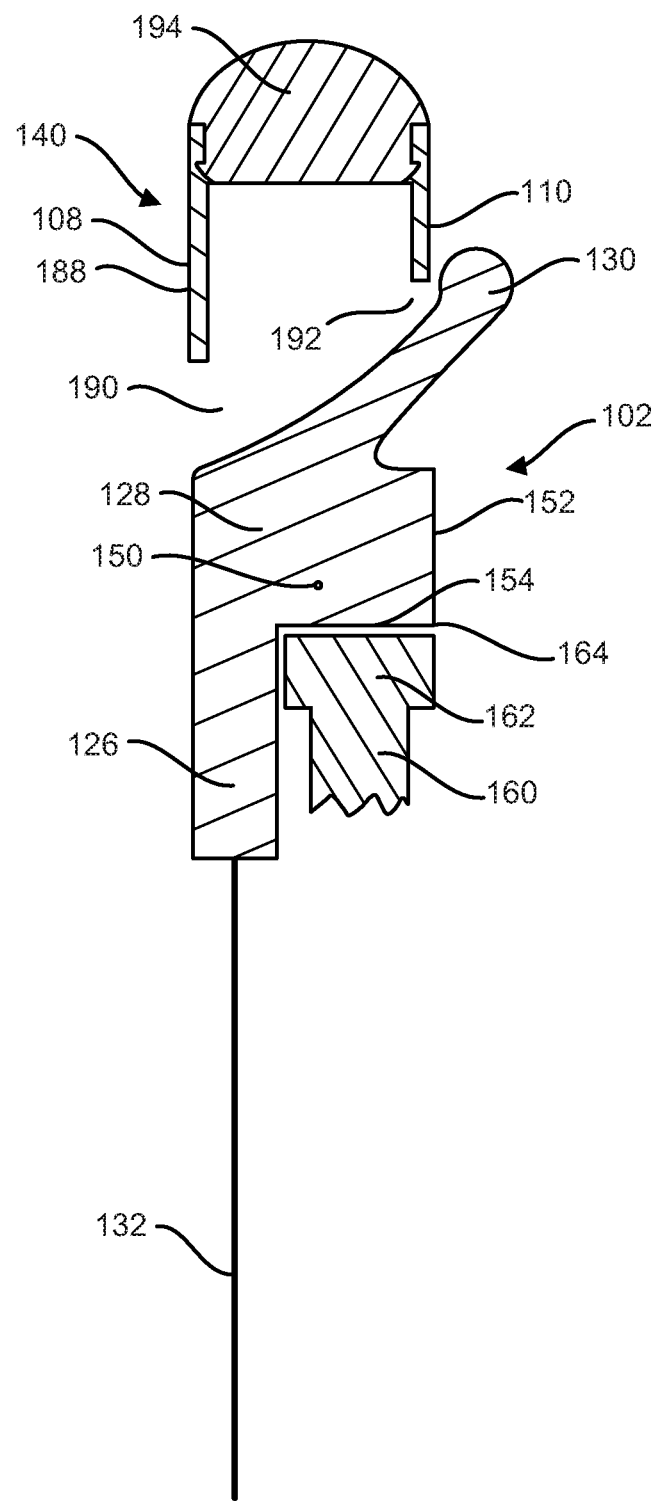
FIG. 15A shows a lateral middle sectional partial view of a variation of the first embodiment in closed, storage position with an activation lever that protrudes only from the dorsal side of the body member.
Figure 15B:
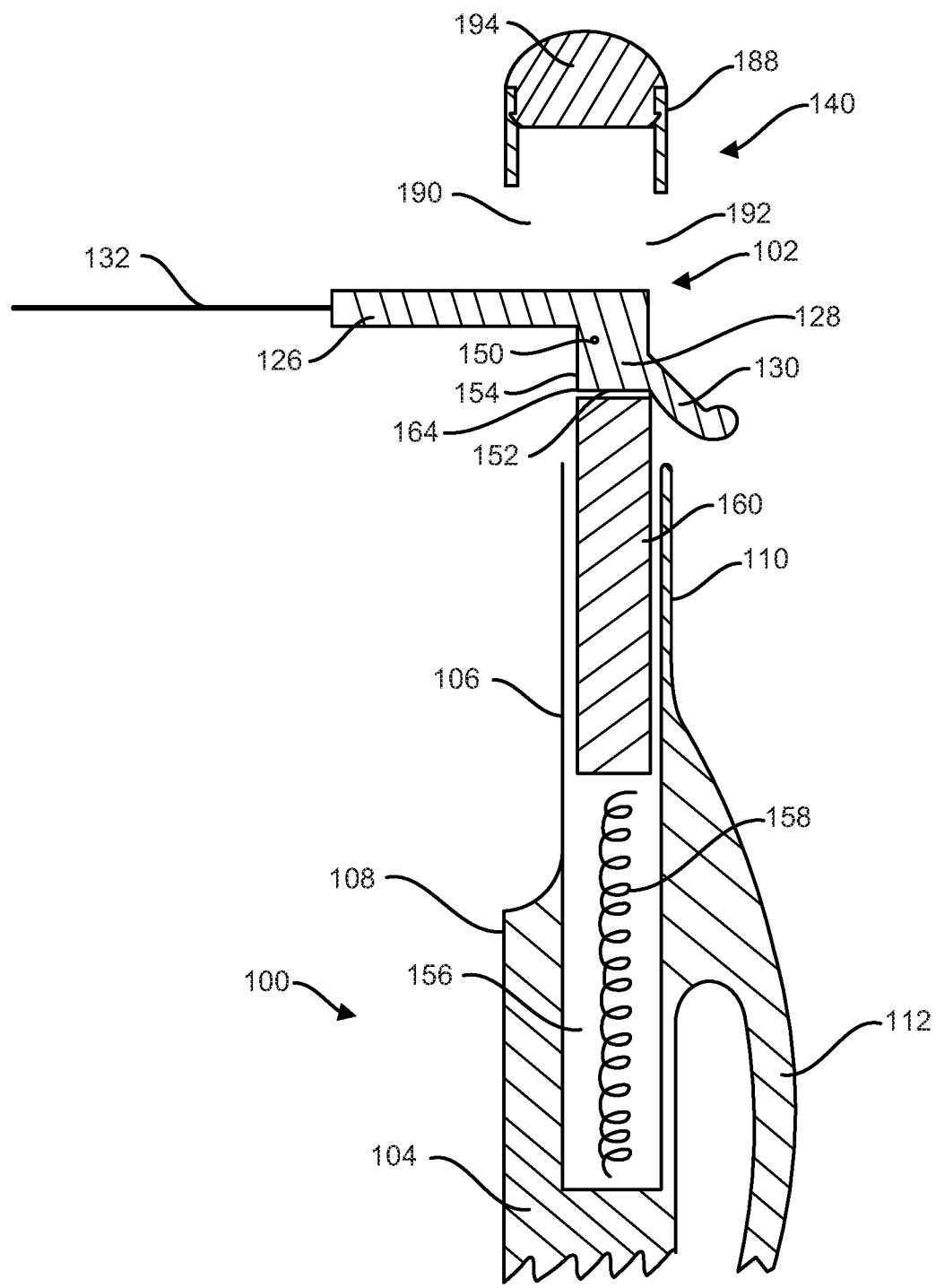
FIG. 15B shows a lateral middle sectional partial view of a variation of the first embodiment in open, testing position with an activation lever that protrudes only from the dorsal side of the body member.

FIG. 15A shows a left lateral sectional view of a variation of the first embodiment while in closed, storage position and FIG. 15B shows the same in open, testing position. In this variation, the distal end 140 of handle member 100 protrudes distally past the distal extent of the activation lever 130 while in closed, storage position forming a handle member cap extension 188. In this variation, the activation lever 130 protrudes only from the dorsal surface/side 110 of handle member 100 while the head member 102 is pivoted into any position within its range of motion.

This variation of the first embodiment provides further protection from unintended pivoting forces upon the activation lever 130 while in closed, storage position. This variation has a window 190 for filament arm 126 protrusion on the ventral surface/side 108 of handle member 100 which allows for unrestricted motion of the filament arm 126 within its allowed/contained range of motion. There also is a window 192 for activation lever 130 protrusion on the dorsal surface/side 110 of handle member 100 which allows for unrestricted motion of the activation lever 130 within its allowed range of motion.

A protective cap 194 may be provided at the distal end of handle member 140 in this variation. The cap 194 is optional. The cap 194 spans across the gap between the retaining flanges 138 and closes the distal end 140 of handle member 100. The cap may also be molded, machined, etc. as one continuous portion of the handle member 100. The cap 194 may also be manufactured as a free piece that is attached during assembly by various methods such a snap fit, glue on, screw on or other methods. The attachable cap 194 can leave a temporary open end to ease the insertion of the compression spring 158, the piston body 160, and the head member 102 during assembly.

This attachable variation of the cap 194 will also allow for simpler and less costly molding or machining of the handle member 100 during manufacture.

Figure 16:
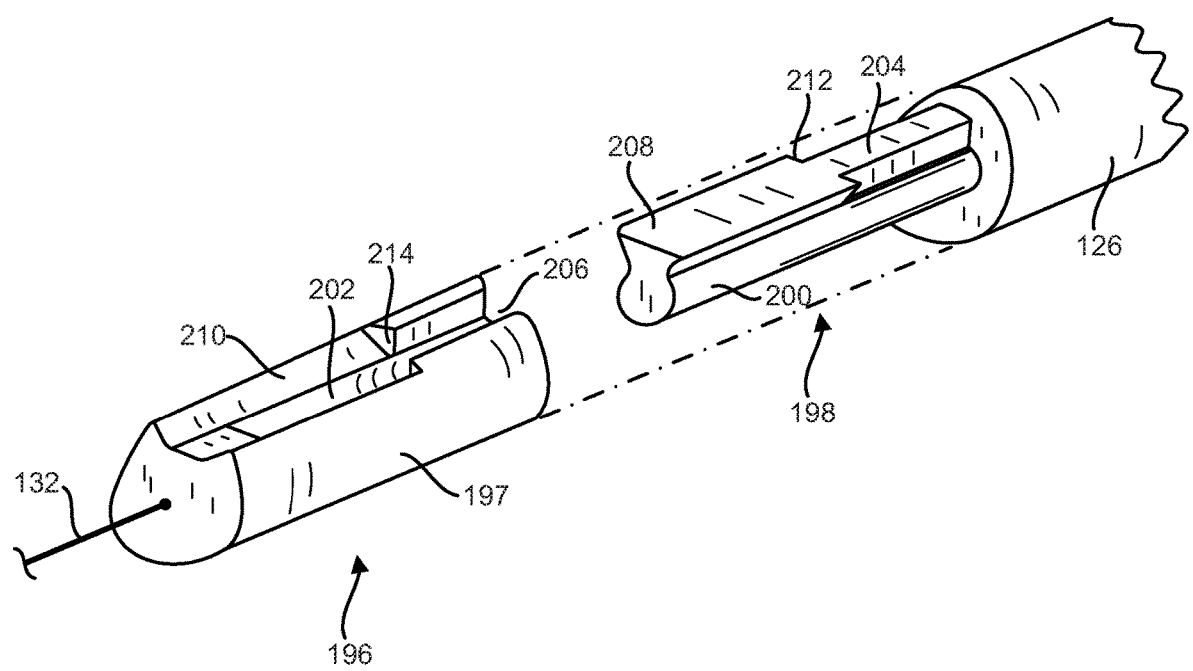
FIG. 16 shows an exploded ventral lateral perspective partial view of a variation of the filament arm with an exchangeable filament assembly.

FIG. 16 shows a closed storage state dorsal right lateral perspective view of the closed, storage state proximal end/tip of the filament arm 126 in a variation of the first embodiment with an exchangeable filament assembly 196. Different size filaments can be used to measure different levels of sensitivity. A 38 mm long nylon filament of varying standardized diameters is most commonly used. Tips of different function such as sharp sensation, dull sensation, temperature sensation, light touch sensation, itch sensation, two-point discrimination, tool tips, etc. can also be used.

Tips of different function or just a new replacement of the worn or damaged original tip can be exchanged in this variation. The version of the variation in FIG. 16 is a configuration of such geometry that the exchangeable filament assembly 196, and the head member 102 in toto, may both be manufactured using relatively inexpensive simple bivalve injection molding techniques without the need for die slides. This version has a receiving shaft 198 at the closed, storage state distal end of the filament arm 126 that securely snap fit mates in a detachable manner with the exchangeable filament assembly 196, The filament assembly 196 is comprised of the filament 132 and a filament base 197.

This version has the exchangeable filament assembly 196 that securely snap fit mates onto a receiving shaft 198. The receiving shaft 198 is composed of a spine 200 of receiving shaft that inserts and mates with a bore 202 in the exchangeable filament assembly 196, A closed, storage state dorsal ridge 204 of receiving shaft mates with an alignment slot 206 on the closed, storage state dorsal side of the exchangeable filament assembly 196 and prevents rotation of the two components around their long axis. A shaft locking flare/wedge 208 mates with a pair of a filament assembly locking bevels 210. When assembled, a shaft distraction buttress 212 abuts against a filament assembly distraction buttress 214 which prevents the exchangeable filament assembly 196 from axially sliding off the tip of the receiving shaft 198.

Figure 17:
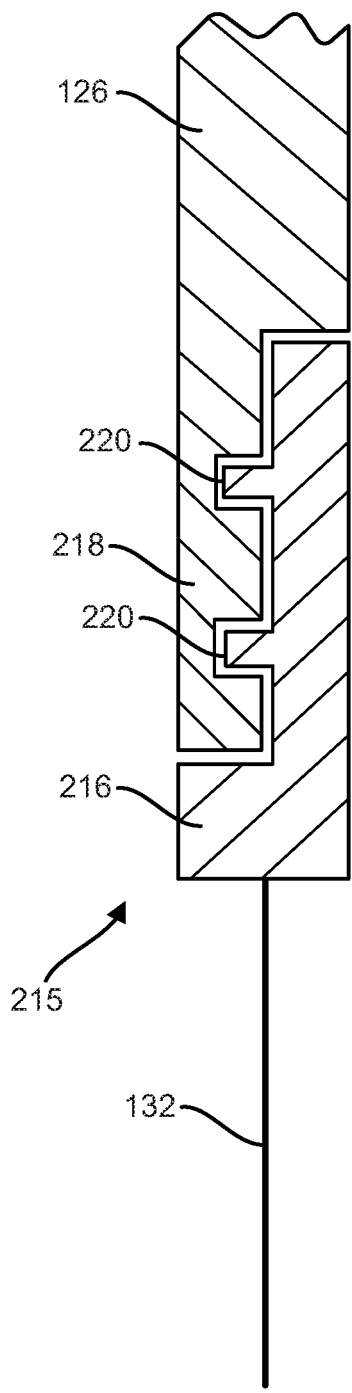
FIGS. 17 and 18 show sectional views of other variations of the filament arm with an exchangeable filament assembly.

FIG. 17 shows a closed, storage state dorsal or ventral sectional view of a variation of the filament arm 126 of the first embodiment with an exchangeable filament assembly 215. This variation has the exchangeable filament base 216 reversibly attached to a lateral receiving tip 218 via a lateral surface peg-in-hole arrangement 220 that reversibly snap fits together. The pegs may be manufactured on either the exchangeable filament base 216 or the lateral receiving tip 218, and the holes manufactured on the opposing surface. The geometry of this variation in FIG. 17 also allows for simple inexpensive bivalve injection molding manufacture of both components with no need for die slides.

Figure 18:
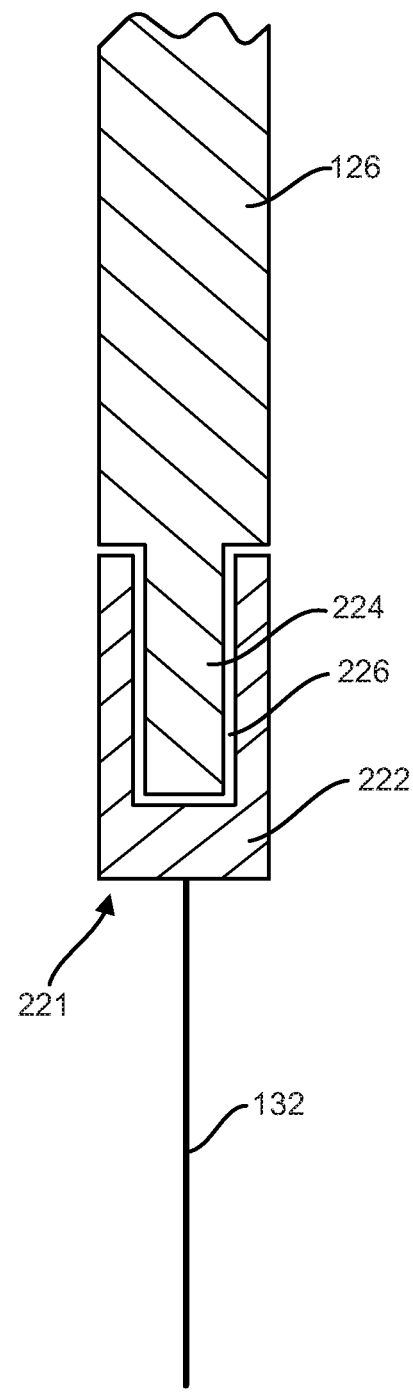

FIG. 18 shows a lateral or closed, storage state dorsal or ventral sectional view of another variation of the filament arm 126 of the first embodiment with an exchangeable filament assembly 221. This variation has a receiving tip 224 that is fashioned into a peg aligned with the long axis of the filament arm 126. An exchangeable filament base 222 has a corresponding bore 226 that fits securely over the receiving tip 224 via a reversible snap fit. This variation also allows for relatively inexpensive simple bivalve injection molding manufacture of both components with no need for die slides.

Operation—FIGS. 1, 5A, 5B: The manner of using the power-assisted-pivot sensory filament testing instrument of the first embodiment is similar to other sensory filament testing devices. In open, testing position, the tip of the sensory filament 132 is compressed against the testing surface/skin until the compression force is limited at a predetermined force by the buckling of the filament along its length. The first embodiment has a cylinder 156 in the handle member 100 that houses a spring 158 acting upon the piston body 160. The contact table 162 of piston acts upon a plate/radial/disc cam formed on the pivoting head member 102. The plate/radial/disc cam is formed by the testing position contact surface 152, the bias corner 164, and the storage position contact surface 154.

The spring-loaded piston force acting upon the cam creates a bias that forces the head member 102 to pivot in the direction of, and maintain the position of, either the open, testing position or the closed, storage position. With the spring-powered pivot assist, the activation lever 130 just needs to be urged in the desired direction with a quick "flick" of a single finger. The operator only needs to initiate the motion, and the power assisted cam and spring-loaded piston follower mechanism completes the motion and maintains the desired position.

This power assisted pivot mechanism (pivot mechanism with biasing device) allows for quicker deployment and quicker storage of the testing device with less effort and attention from the operator. The power assisted force to maintain the head position protects the filament 132 from unintentional exposure with potential damage while stored and, also provides a stable, consistent filament position while testing. Unintentional filament exposure from the storage position could easily lead to damage of the fragile sensory filament 132.

The power assisted pivot force will also help the filament position "auto correct" back into the channel 106, for safe storage, as long as the rotation that exposes the filament 132 does not exceed the tipping threshold of the cam and spring-loaded piston follower mechanism.

The pivot moment 150 of head member 102 is offset relative to the testing position contact surface 152 of head member 102 and the storage position contact surface 154 of head member 102. The pivot moment 150 of head member is a longer distance from the bias corner 164 along the storage position contact surface 154 of head member 102 than it is along the testing position contact surface 152. This allows the bias corner 164 to slide less distance along the contact table 162 to reach the tipping point when the head member 102 is pivoted toward the closed storage position. This position of the pivot moment 150 also requires the bias corner 164 to slide a greater distance along the piston contact table 162 to reach the tipping point when the head member 102 is pivoted toward the open testing position. The offset position of the pivot moment 150 of head member requires a longer arc of rotation to pivot the cam to the tipping threshold while opening the device, under the expansile force of the spring-loaded piston body 160, than while closing the device. This geometry favors the closed, storage position since it is more critical to prevent accidental opening during storage, than to prevent accidental closure while testing.

The offset position of the pivot moment 150 creates extra length between the pivot moment 150 and bias corner 164 along the storage position contact surface 154. This extra length causes the spring 158 to be significantly more compressed in the open testing position than in the closed storage position. This increased spring compression increases the power assist force that pivots the head member 102 back into closed storage position. This increased power assist force in the direction of closure also favors protection of the testing filament 132.

When grasped in the most likely manner as seen in FIG. 1, the activation lever 130 is operated by the index finger. In this position, the index finger has relatively great strength and control to flex and overcome the relatively increased opening resistance afforded by the offset pivot moment 150 of head member. While grasped in this manner the index finger has relatively weak strength and poor control to extend and close the device, so the offset position of the pivot moment 150 allows the head member 102 to pivot closed easily with just a slight crude urge of the activation lever 130 in the direction of closure. The mechanics favor the more stable bias of the closed, storage position to error on the side of filament protection.

The distal and dorsal protrusion of the activation lever 130 allows for easy pivoting of the head member in either opening or closing direction with a simple quick "flick" of an index finger while grasping the device from the dorsal side with the right hand. In this grasped position, the operator's thumb will grasp the left lateral side of the body of handle member 104 while the fingers three, four and possibly five grasp the right lateral side of the body of handle member 104. The grasp allows the index finger to be free and positioned to "flick" the activation lever 130 in either desired direction, thus pivoting the head member 102 freely between the two biased positions of closed, storage position and open, testing position. This grasp with the right hand to operate the pivot function also coincides with the identical grasp one would naturally use to retrieve the first embodiment from the left breast pocket of a lab coat, jacket, shirt, etc., from a horizontal surface, or from a pencil storage cup to initiate the sensory testing procedure. This allows for one quick seamless motion to retrieve the embodiment to initiate testing, perform testing, and clip back into the left breast pocket for storage, all without changing hand position upon the embodiment. This allows for maximum efficiency of the whole testing process.

The position of the pocket clip 112 can determine the amount of handle member 100 that protrudes from the breast pocket while clipped in place. This amount of protrusion can be optimized leaving much protruding for ease of grasping during retrieval from the breast pocket, or optimized leaving little protrusion making the embodiment relatively unobtrusive while clipped in the breast pocket for storage.

Without the guard 184 for activation lever 130, the activation lever 130 may be vulnerable to unintentional pivoting force as the operator bends the torso forward while the first embodiment is clipped in a breast pocket while in closed, storage position. The activation lever 130 is angled in the dorsal direction facing away from the operator's body while clipped in a breast pocket. This angle prevents body contact when the operator bends forward and thus prevents accidental pivoting of the head member 102 into the open, testing position. The position of the pocket clip 112 relative to the orientation of the activation lever 130 in this first embodiment gives the appearance of a small, bird sculpture perched on the tip of a stick (an elongated form) facing outward, when clipped in the breast pocket for storage. This adds visual interest to the embodiment.

A cross sectional shape of the handle member 100 that is oval or any shape except circular/round, helps the operator tactilely align the testing filament 132 by feel only at the necessary ninety degrees from the testing surface, without a need for visual confirmation of alignment. Partially flattened areas, ridges or grooves on the surface of the handle member 100 may also serve to aid this tactile alignment. This allows the operator's focus to be at the contact point of the filament tip and testing surface, to ensure that the testing force has been applied in the appropriate manner with minimal impact force. The channel lip 360 in FIGS. 32, and 37C-37G or similar ridge or prominence around the periphery of the channel 106 is a variation that can discourage placement of the grasping fingers from covering the channel 106. The channel lip 360 can also be used as a buttress against the grasping fingers to further stabilize the embodiment in use.

The variation of the first embodiment with the locking slider 168 on the filament arm 126 (FIG. 11) is used in an identical manner as the first embodiment that does not have this variation, except for the optional extra step of locking and unlocking the filament arm 126. The locking and unlocking mechanism is configured to be operated without changing grasp of the embodiment during the seamless retrieval, testing, and storage motion involved in its intended use sequence.

During the retrieval or storage motion of the process, the locking slider can be maneuvered to the desired position with the index finger or thumb of the operating hand, without the need for a time-consuming change in grasp. The handle member 100 may be axially rotated slightly along its long axis while grasped, to facilitate reaching the locking mechanism if the operator desires. This rotation will not slow or interfere with the intended use sequence or change the grasp.

The pocket clip 112 is also configured to facilitate rapid one-handed operation. The clipping tension is great enough to hold the embodiment securely at the desired depth in the breast pocket. The tension is appropriate to secure it to thinner material such as a dress shirt or scrub top as well as to thicker fabric such as on a lab coat.

The position of the pocket clip 112 can determine the amount of the handle member 100 that protrudes from the breast pocket while clipped in place. The length of the pocket clip 112 is also long enough to allow the embodiment to sit stored in the breast pocket with a various operator determined length of the embodiment protruding out of the pocket. Some operators may desire a minimal protrusion above the pocket favoring unobtrusiveness. Others may favor a longer length protruding favoring ease of rapid grasp for the intended use sequence.

The geometry of the pocket clip 112 and width of the gap 182, between the proximal tip of the pocket clip 112 and the body 104 of handle member 100, are such to favor the pocket clip 112 quickly and easily catching the lip of the pocket for storage with little attention needed.

The first embodiment is also configured to be relatively thin in cross section, roughly similar to the range of thin to thick writing pens. The components and features are configured to work with in this size range. A narrower thin profile will be favorable to fit in a breast pocket or container that is already filled and crowded with other objects such as pens, eyeglasses, tools, etc.

The end opposite the head member 102 may comprise a functional end. The functional end may be a beveled scraper tip 116 that is configured to part between other pens/objects for ease of storage in a crowded pocket, pencil cup, etc. The scraper edge also mimics a fingernail when used to scrape the sole of a foot to test for a Babinski reflex.

Other configurations of the functional end or scraper tip 116 may be used, such as rounded, squared, pointed, etc. The functional end or scraper tip 116 may also be fashioned for different purposes, such as a conductive resilient tip for operating touch screen devices.

The sharp-tipped protrusion 400 and dull-tipped protrusion 402 on the variation of the activation lever in FIG. 13L can be used to test sharp versus dull sensory perception. This is done by alternately touching the patient's skin randomly with either sharp or dull protrusion. The patient attempts to identify each touch as sharp or dull without any visual or audible cues. The handle member 100 can be rolled/twisted/spun around it's long axis without changing grasp to introduce either protrusion to the patient's skin surface for testing.

The power assist mechanism and configuration of the first embodiment make the filament testing process quicker to perform, and less threatening to the patient, while providing extra protection to the filament 132. The power assist mechanism (biasing device) also adds more interest for the operator similar to the interest and enjoyment of a fidget device. The embodiment also serves to test the Babinski reflex or perform other duties with the proximal end of handle member 114. The embodiment can also test sharp versus dull sensory perception. The embodiment is relatively inexpensive and easy to manufacture and assemble. The configuration attempts to minimize visible sharp crevices where debris can accumulate and flaw the aseptic appearance of the embodiment. The perpendicular protrusion of the filament 132 relative to the handle member 100 makes the embodiment unlikely to be confused by a fearful patient with a hypodermic needle and syringe.

Figure 19A:
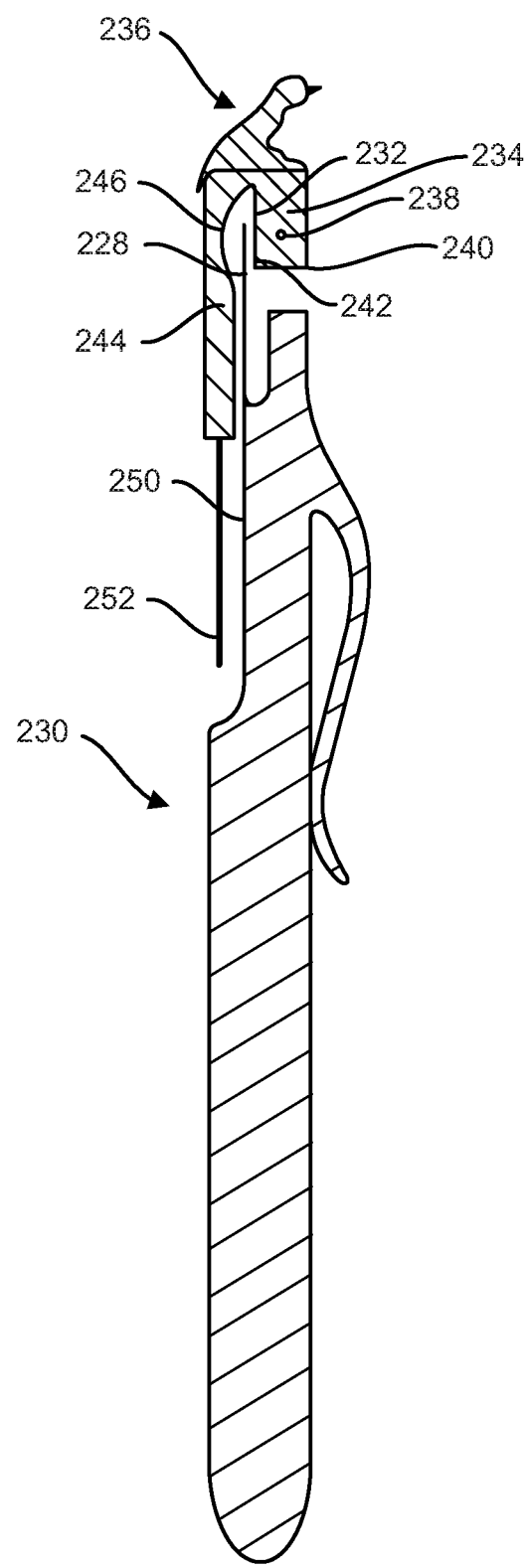
FIGS. 19A to 19C show middle sectional lateral views of a second embodiment with the head member pivoted into a range of different positions.
Figures 19B, 19C:
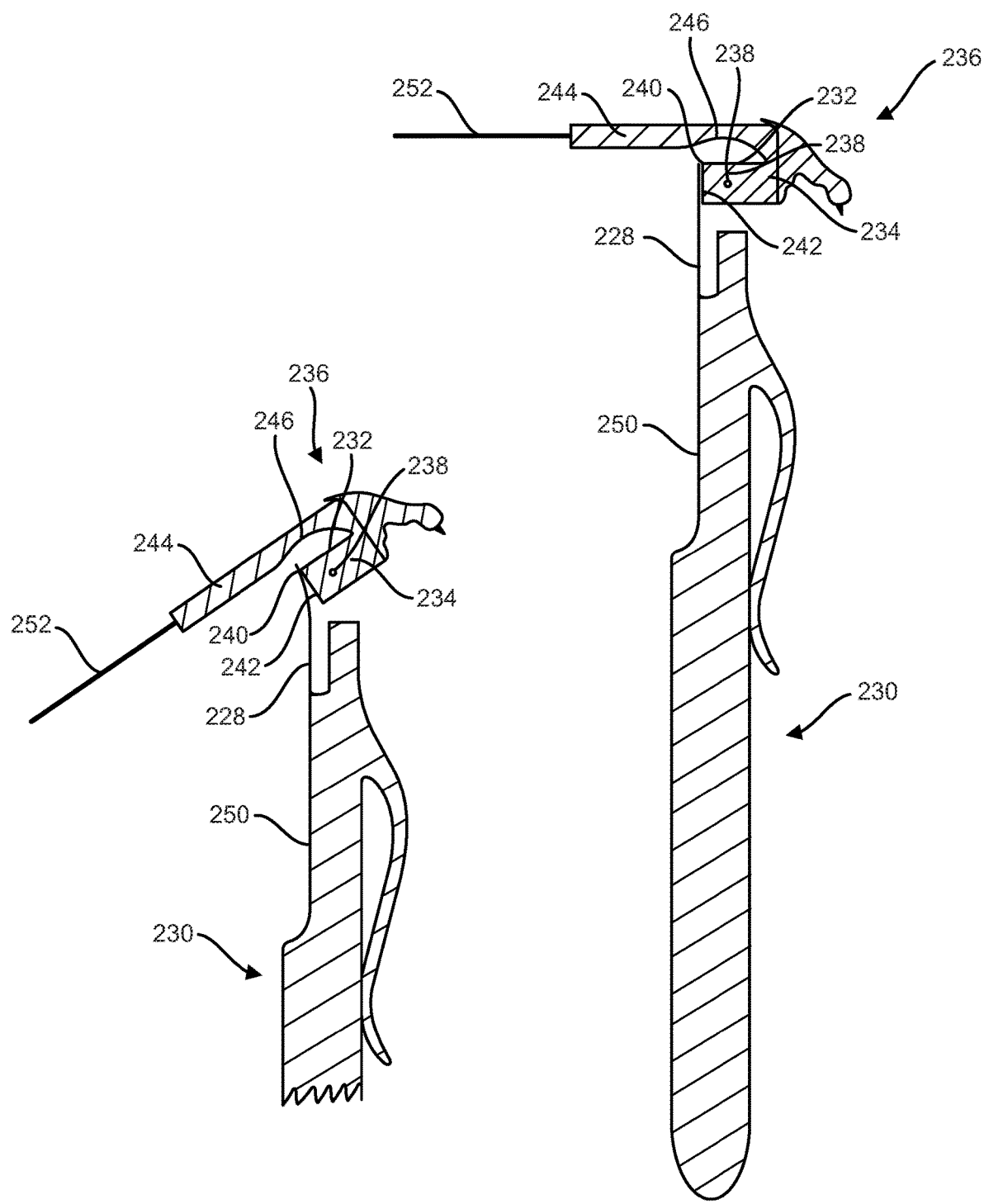

Second Embodiment FIGS. 19A, 19B, 19C

FIG. 19A shows a lateral middle sectional view of a second embodiment in closed, storage position. This embodiment uses a leaf/flat spring 228 axially aligned with a handle member 230. The distal end of the leaf spring 228 contacts a storage position contact surface 232 of a body 234 of head member 236 in a parallel manner when the spring 228 is in fully relaxed resting position. When a head member 236 is pivoted around a pivot moment 238 of head member into the open, testing position, a bias corner 240 flexes the leaf spring 228 as seen in FIG. 19B. Once the head member 236 is pivoted into the full open, testing position the leaf spring 228 once again rests in a fully relaxed position in parallel contact with a testing position contact surface 242 of head member 236 as shown in FIG. 19C. In this leaf spring embodiment, the closed, storage state dorsal surface of a filament arm 244 has a recess 246 so there is no interference between the leaf spring 228 and the filament arm 244. The function of this second embodiment is identical to the function of the first embodiment. The main difference is the type of spring and direction of the spring's force upon the body 234 of the head member 236.

This embodiment can be configured with various stops to prevent excess range of motion where a portion of the head member 236 abuts against a portion of the handle member 230. An example of this would be the filament arm 244 having adequate length to abut against the deep surface of the channel 250 when the head member is pivoted into full closed, storage position as shown in FIG. 19A. This will protect a filament 252 from damage if the head member 236 were to overshoot its storage position. The leaf spring 228 may be made of metal, plastic, or other relatively stiff yet elastic material to make an effective leaf spring. The leaf spring 228 may be a separate piece added to the handle member 230, or molded as part of the handle member 230 and of the same material such as, but not limited to, ABS plastic. The advantages of this embodiment may include less costly materials, less pieces to assemble, less time and effort for assembly, etc.

Figure 20A:
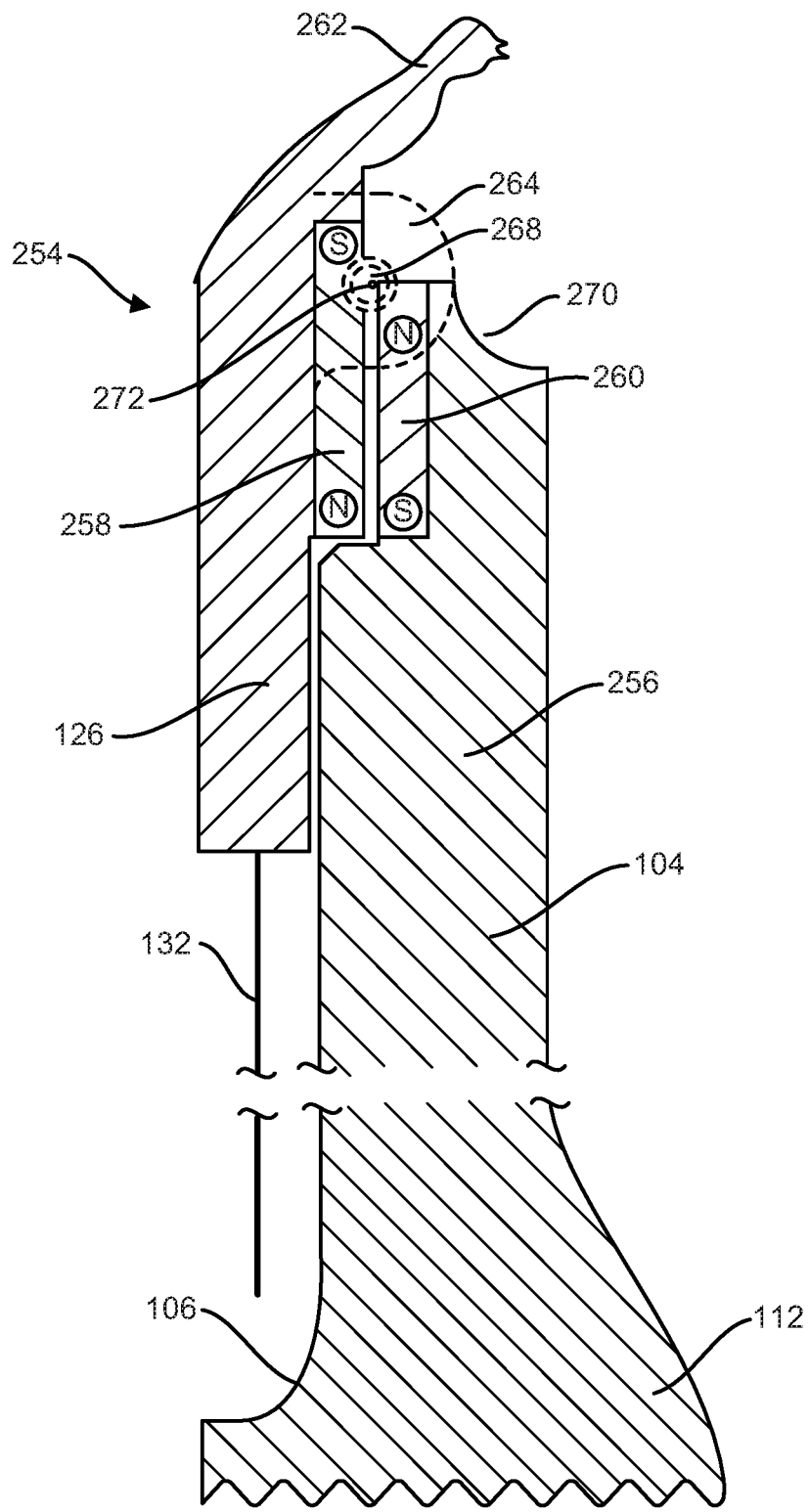
FIG. 20A shows a middle sectional lateral partial view of the third embodiment in closed, storage position.
Figure 20B:
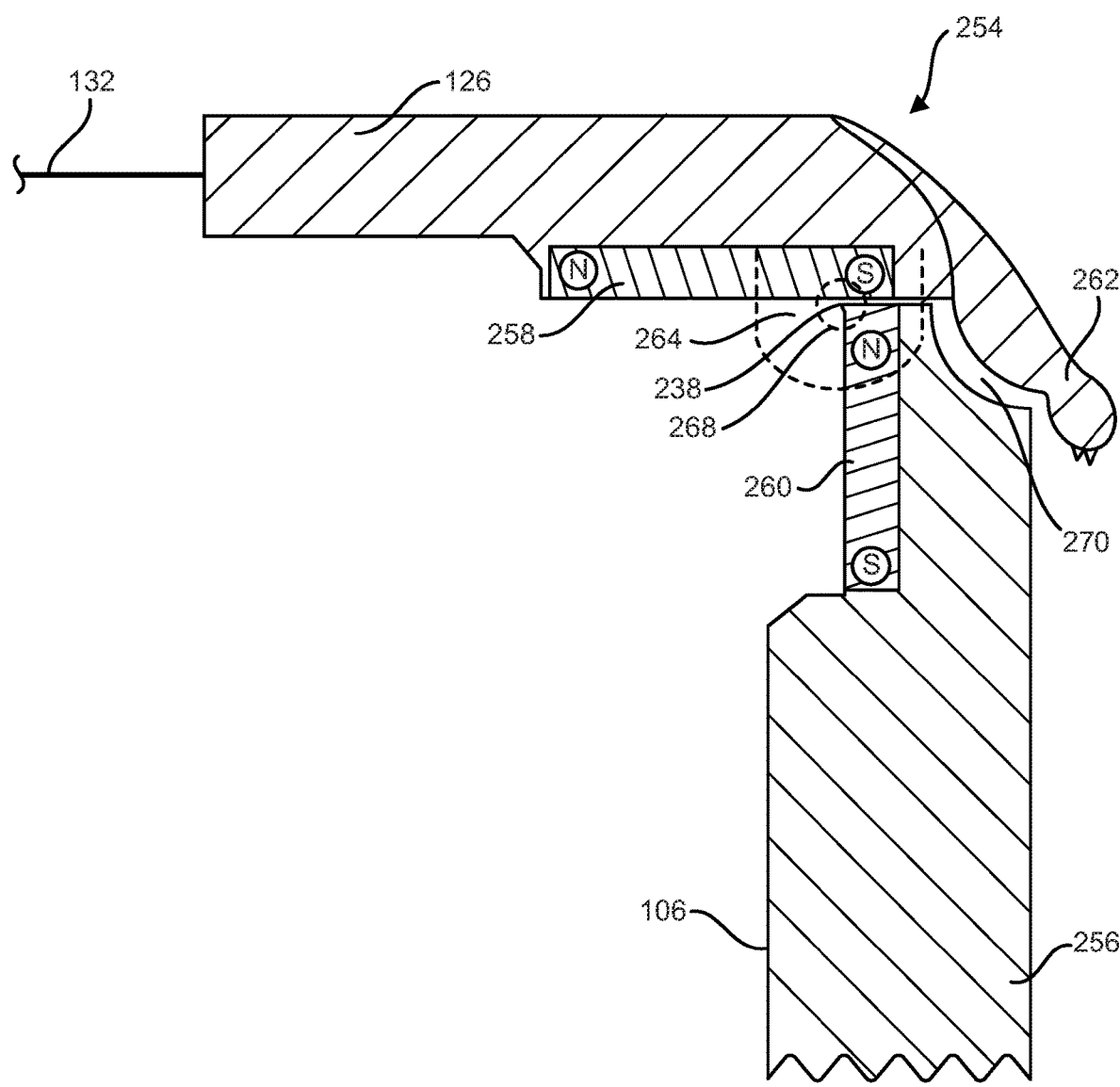
FIG. 20B shows a middle sectional lateral partial view of the third embodiment in open, testing position.
Figure 21:
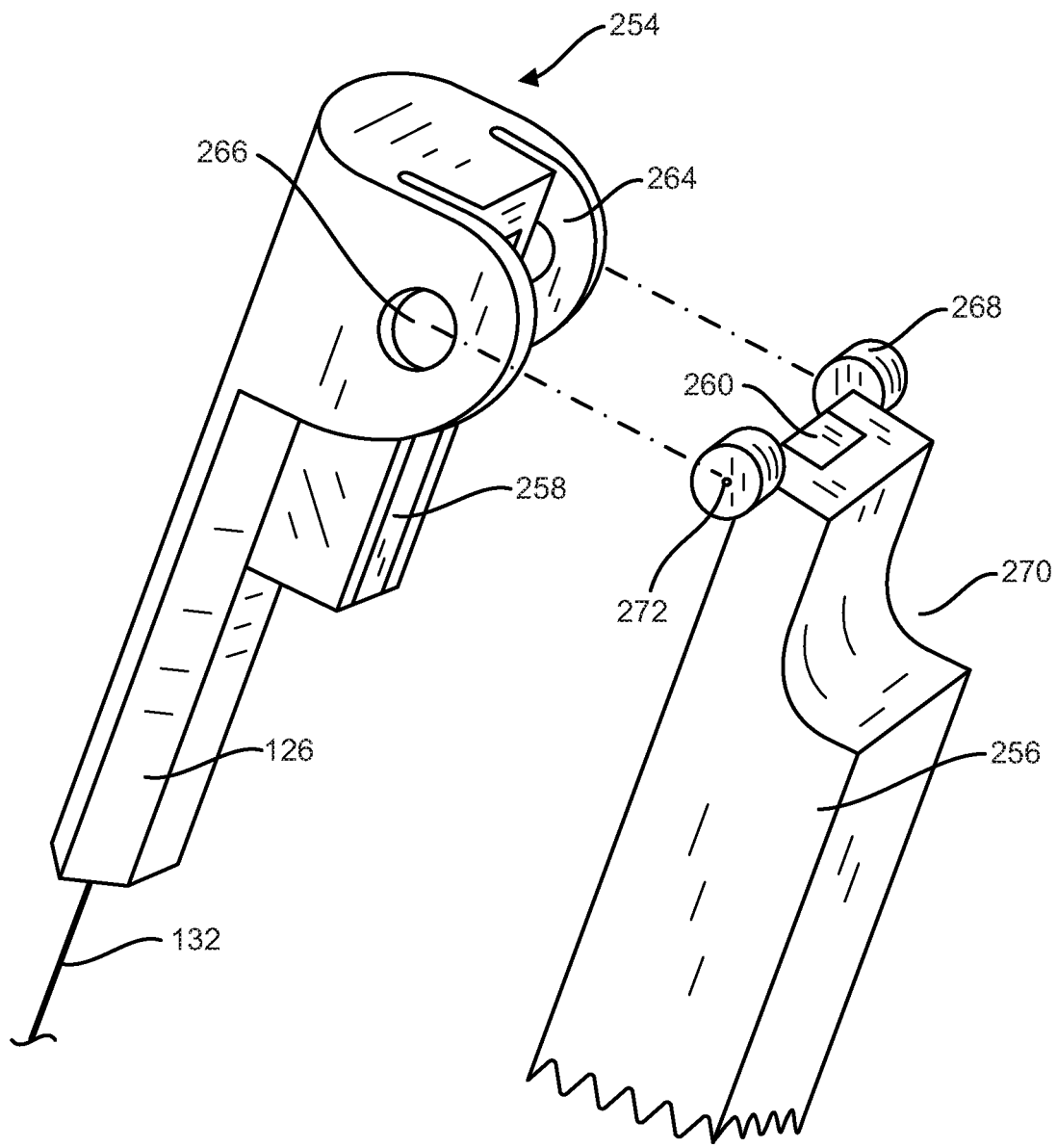
FIG. 21 shows an exploded perspective view of the head member and distal handle member of the third embodiment.

Third Embodiment FIGS. 20A, 20B, 21

FIG. 20A shows a lateral middle sectional view of a third embodiment in closed, storage position. This embodiment uses magnetic forces to power assist the pivot of a head member 254 upon a distal end of a handle member 256, A head member bar magnet 258 opposes a handle member bar magnet 260 aligned in mating polarity. One of these two magnets, such as the longer one, may be replaced by a section of ferromagnetic material that is attracted to the opposing magnetic without producing its own magnetic field. FIG. 20B shows a lateral middle sectional partial view of the third embodiment in open functional, testing position. The length of the head member bar magnet 258 is longer than the handle member bar magnet 260. The length differential is such that the full length of the ventral surface of the handle member bar magnet 260 is in contact with a portion of the head member bar magnet 258 while in closed, storage position and the full distal surface of the handle member bar magnet 260 is in contact with a portion of the head member magnet 258 while pivoted into open, testing position. FIG. 21 shows an exploded oblique distal lateral dorsal perspective partial view of the third embodiment with an activation lever 262 (shown in FIGS. 20A, 20B) removed, FIG. 21 more clearly shows the relationship of the head member 254 to the body of the handle member 256. An axle flange 264 has an axle hole 266 that fits over an axle peg 268 on the body of the handle member 256. The axle flanges 264 are thin, long and flexible enough to be flexed apart to straddle and clear the width of the paired axle pegs 268 for assembly. The material, such as ABS plastic, metal, etc., of the axle flanges 264 is resilient enough to allow a secure snap fit of the head member 254 over the axle pegs 268. The axle flanges 264 and/or the axle pegs 268 may have a bevel that aids in assembly but resists disassembly to the desired degree.

The body of the handle member 256 has a recess/cut out 270 so the activation lever 262 as shown in FIG. 20B does not prematurely abut against the body of the handle member 256 and interfere with the needed pivot motion of the head member 254.

A pivot moment of the head piece 272 should be at the distal ventral corner of the handle member bar magnet 260, This will allow the head member bar magnet 258 to alternately flip between contact with the distal surface and ventral surfaces of the handle member bar magnet 260. The bar magnets may be cylindrical and slid into channels that encompass approximately three quarters of their circumference. This leaves approximately one quarter of their side surface exposed for contact with the opposing magnet, yet will not rely on adhesives for their secure seating. Other geometries of magnets and mounting slots may be used.

Direct magnet to magnet contact will maximize the magnetic forces and minimize the bulk and cost of the magnets.

A fixed axle could be used also to hold the head member 254 to the body of the handle member 256. Two separate fixed axles may also be used that do not cross the magnets and interfere with their magnetic force.

Magnets of different geometries such as bar, cylinder, disc, horseshoe etc. may be used. Separate sets of magnets may also be used for the open and closed bias positions. A set of, three, or four magnets can be configured to accomplish the same function as the two magnets.

A variation of the third embodiment may just have magnets paired to favor the closed, storage position. The open testing position may be maintained during testing by the operator maintaining the opening force with a finger retained on the activation lever 262.

The operation of this third embodiment that uses magnets is identical to the previous two embodiments and amendable to the previous variations that do not pertain to the power assist mechanism.

Advantages

This third embodiment has a magnetic power source that will not fail. The magnetic flipping pivot motion adds interest and enjoyment to the operator's experience, similar to the interest and enjoyment of using a fidget device.

Fourth Embodiment FIGS. 22A, 22B, 23, 24, 25A-F

Figure 22A:
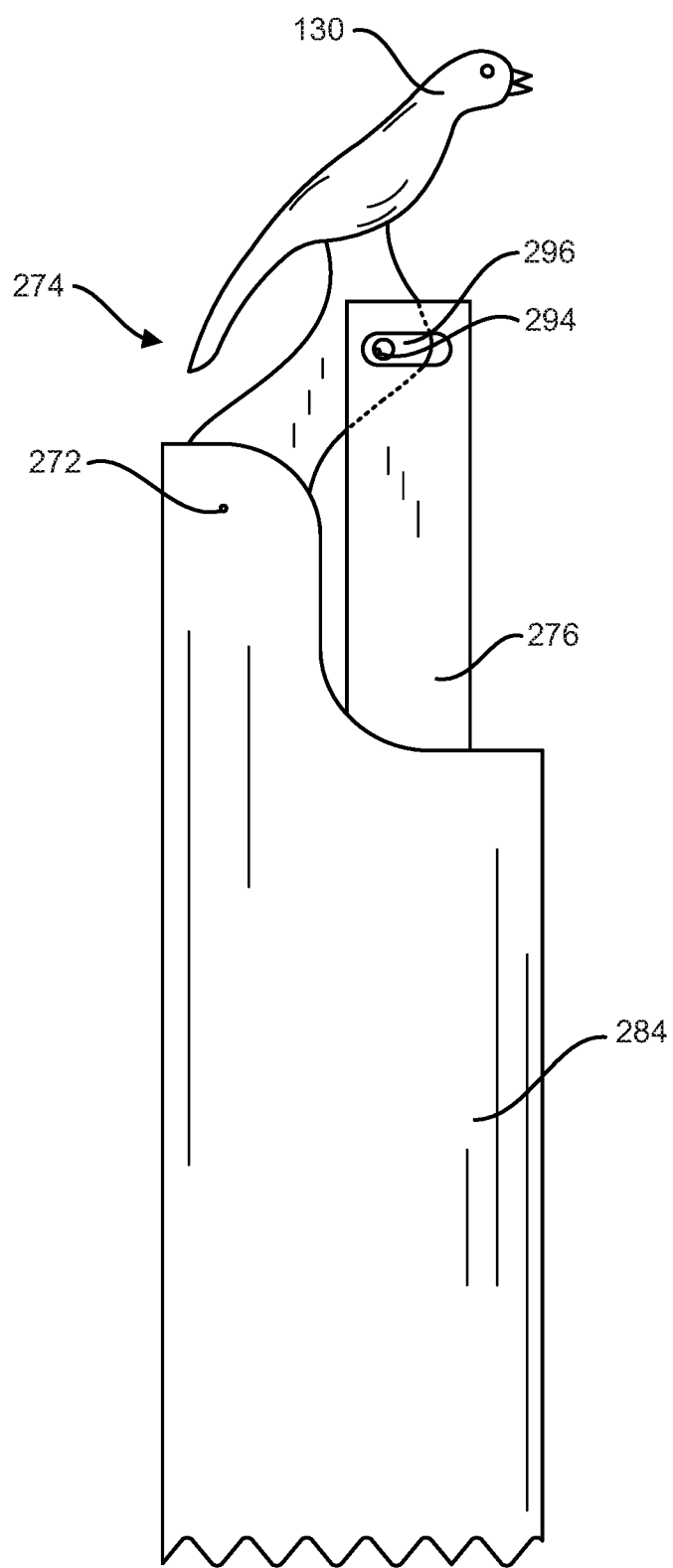
FIG. 22A shows a partial left lateral view of the distal end of the fourth embodiment in closed storage position.
Figure 22B:
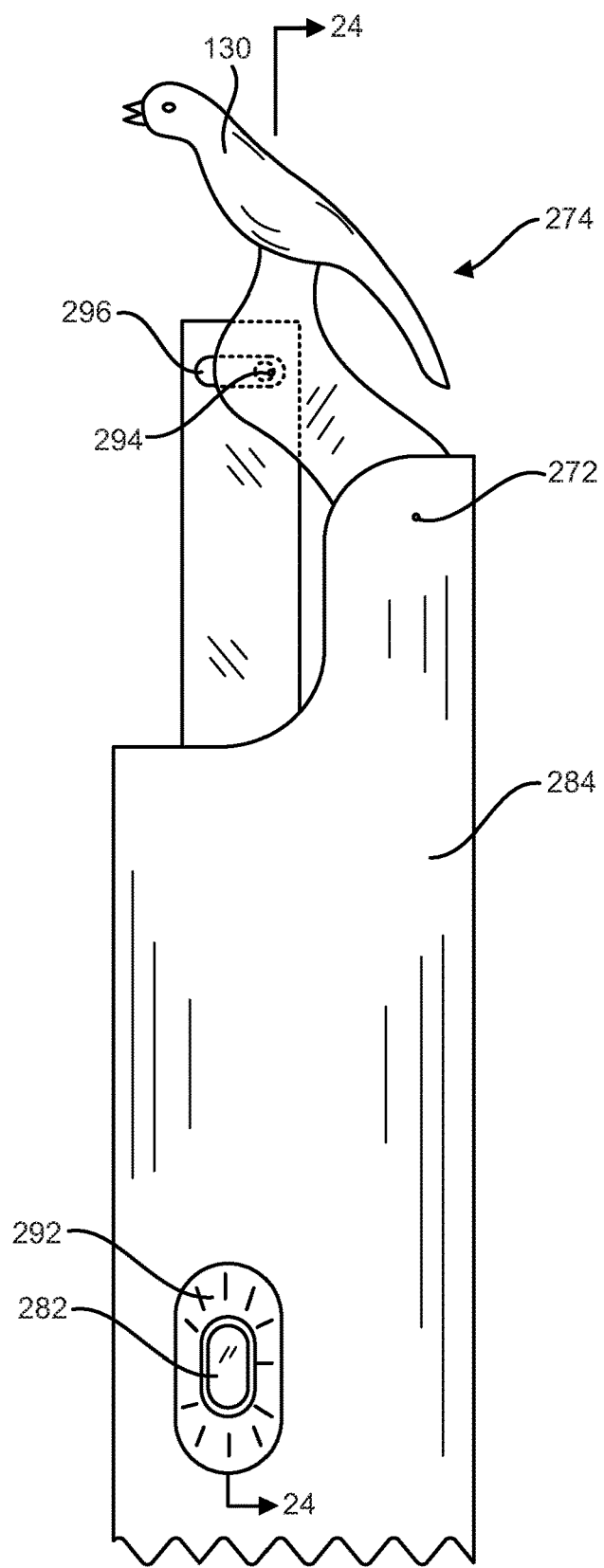
FIG. 22B shows a partial right lateral view of the distal end of the fourth embodiment in closed storage position.
Figure 23:
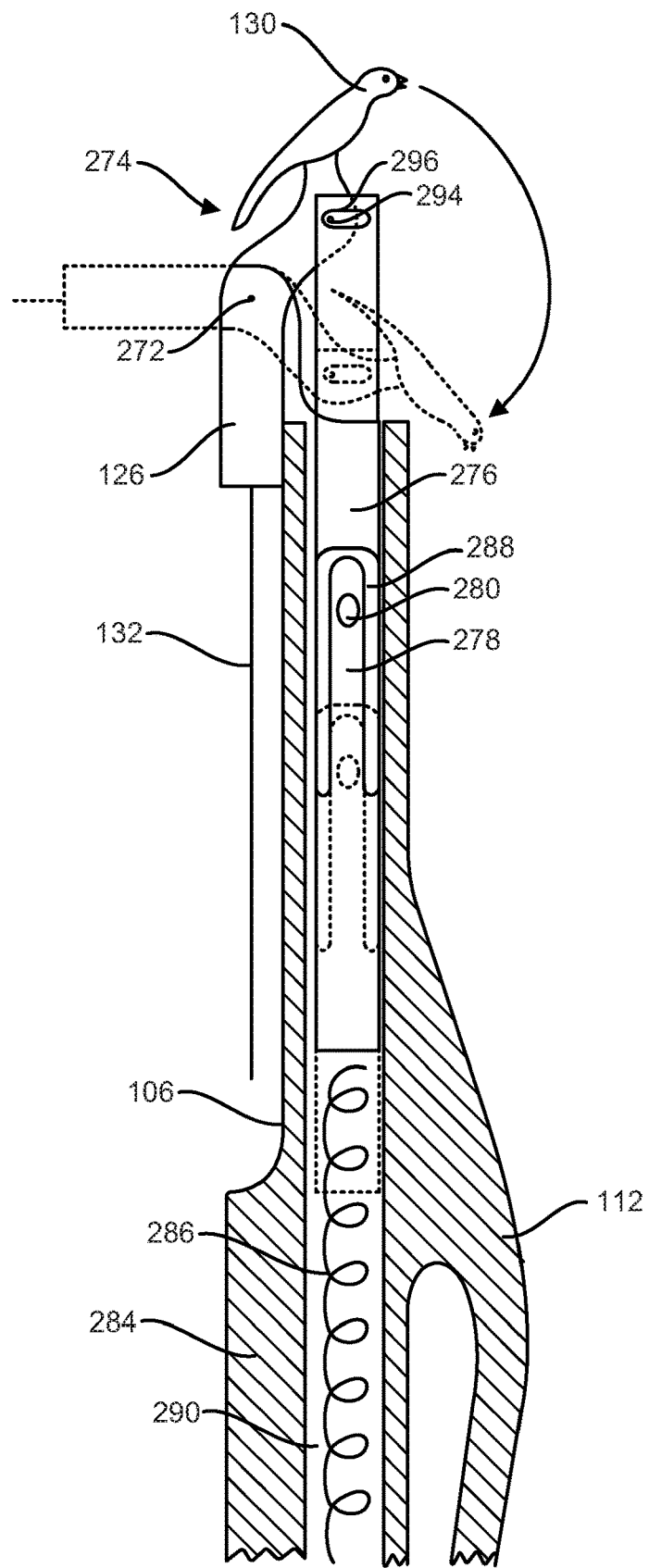
FIG. 23 shows a sectional lateral partial view of the fourth embodiment in closed, storage position and in phantom representing the embodiment in open, testing position.
Figure 24:
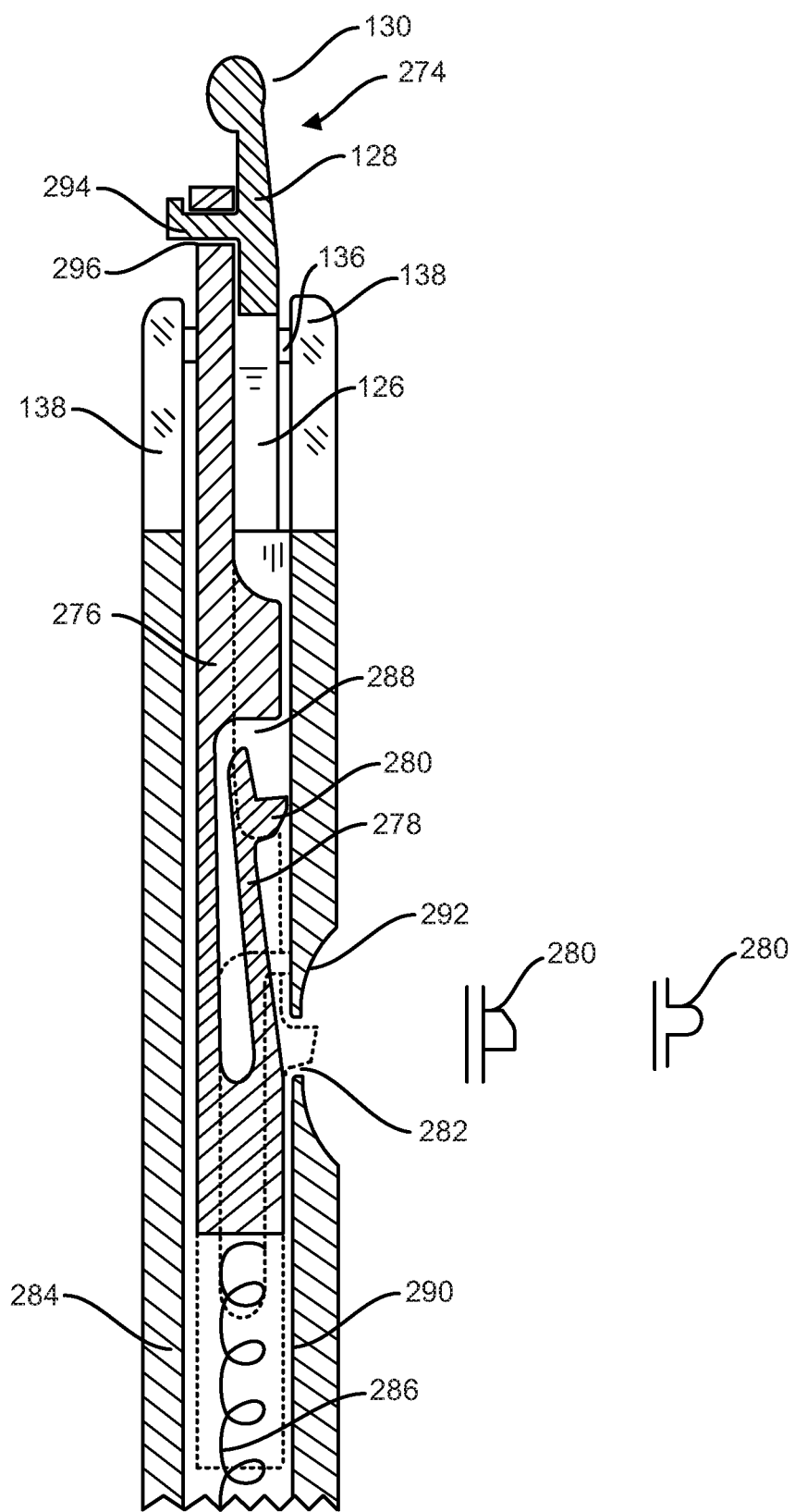
FIG. 24 shows a sectional ventral partial view of the embodiment of FIG. 22B taken at the sectioning plane and in the direction indicated by section lines 24-24.

A fourth embodiment is shown in partial lateral view in FIGS. 22A and 22B, FIG. 23 shows a left lateral cutaway/sectional view of the fourth embodiment which utilizes a Scotch yoke and a spring and latch piston mechanism. FIG. 24 shows the embodiment of FIG. 22B and FIG. 23 taken at the sectioning plane indicated by section lines 24-24 of FIG. 22B. The Scotch yoke mechanism translates the rotary motion of a head member 274 to linear motion of the piston 276 and vice versa. The piston 276 has a leaf/flat spring 278 in line with its long axis. The free end of the leaf spring 278 has a locking button/latch 280 that protrudes from a hole 282 in a handle member 284 only when the head member 274 is pivoted into the full open, testing position. The protrusion of the locking button 280 through the hole 282 holds the piston 276 in place against the expansile force of a compression spring 286. The head member 274 is thus also held in place through the mechanical linkage of the Scotch yoke when the piston is held in place.

The piston 276 has a cavity 288 to allow room for deflection of the leaf spring 278 so the locking button 280 can fit within the confines of a piston cylinder 290 as seen in FIG. 24. The handle member 284 has a recess/dimple 292 surrounding the hole 282. This recess 292 allows the locking button 280 to protrude from the hole 282 in the lateral surface of the handle member 284, but not protrude past the border line of the lateral surface of the handle member 284. This configuration allows finger access to press the locking button 280 inward and release it from the hole 282 while leaving the locking button 280 relatively protected from accidental release. Once the locking button 280 is released from the hole 282, the locking button 280 will ride with the piston 276 and be retained by the piston cylinder 290 as the piston 276 is pushed to the distal end of the piston cylinder 290 under the expansile force of the compressed spring 286.

This distal excursion of the piston 276 translates through the Scotch yoke linkage to pivoting of the head member 274 into closed storage position. A peg 294 and a slot 296 of the Scotch yoke mechanism may have several configurations as pictured in FIGS. 25 A-F that allow quick easy assembly yet discourage separation of the two components during use.

FIGS. 25 A-F show a few variations of flares, lips, bevels, flanges, etc. that help maintain the peg 294 within the slot 296 during the range of motion of these two component parts during normal use.

The locking button 280, hole 282, and leaf spring 278 mechanism can be aligned in an axial plane of choice irrespective of the planes of the Scotch yoke function and head member 274 pivot function.

A variation of the fourth embodiment may lack the structures for the locking/latching mechanism. In this variation, the embodiment does not lock into the open, testing position. The open, testing position is maintained during testing by the operator maintaining the opening force with a finger retained on the activation lever 130. In this variation the power assist mechanism will automatically close the embodiment once the opening force on the activation lever 130 is released by the operator.

Operation

Operation of this fourth embodiment with the Scotch yoke, and spring with latch piston mechanism, is almost identical to use of the first embodiment other than the button-release, automatic closure mechanism and the need to fully pivot the head member 274 until locked in full open testing position. The closure mechanism is activated by pressing the locking button 280 from its protruding position through the hole 282 using a finger with no need to reposition the grasp of the operator. Release of the locking button 280 from the hole 282 allows the piston 276 to ride automatically toward the distal end of the handle member 284 under the expansile force of the compressed spring 286. This movement of the piston 276 translates into closure of the head member 274 through the Scotch yoke mechanical linkage.

This embodiment is grasped identically to the first embodiment. The head member 274 is pivoted open in an almost identical manner, but must be manually pivoted the full ninety degrees until fully opened to lock and maintain the open testing position.

One advantage of this fourth embodiment is increased pivot range of the head member 274 that favors the storage position bias. Any pivot position of the head member 274 short of fully locked open, testing position will be under power assist to automatically revert back to the closed, storage position. This reduces the chance of accidental full opening which could damage the filament 132. The closure method is also simplified with a single press of a button.

Fifth Embodiment—FIGS. 26A-27D

Figure 26A:
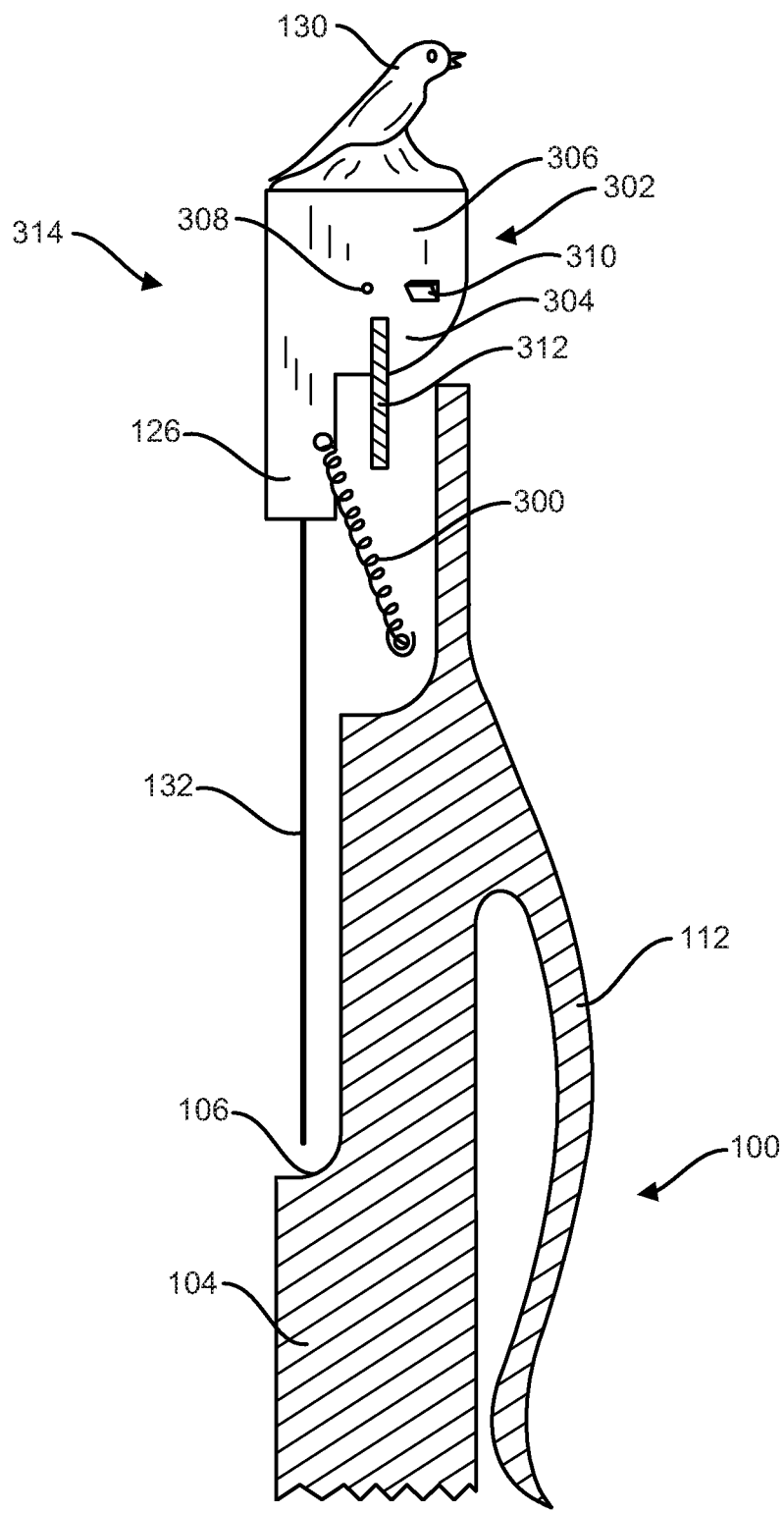
FIG. 26A shows a lateral sectional partial view of the fifth embodiment in closed, storage position.
Figure 26B:
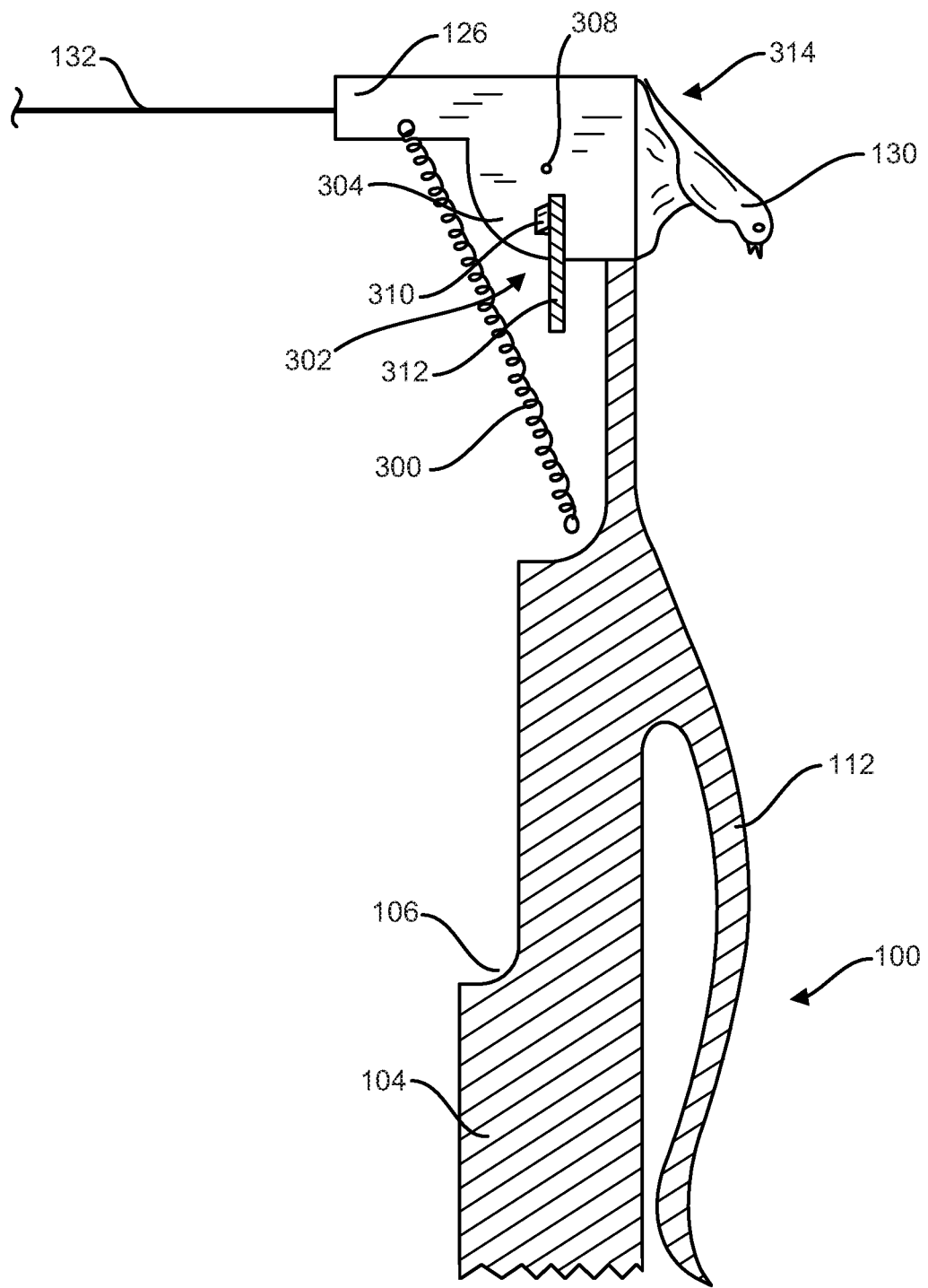
FIG. 26B shows a lateral sectional partial view of the fifth embodiment in open, testing position.

FIGS. 26A and 26B show lateral sectional views of a fifth embodiment that utilizes a tension spring 300 and a locking/latching cam 302. FIG. 26A shows a partial sectional view of the distal end of the embodiment in closed, storage position while FIG. 26B shows the same view in open, testing position. The locking/latching cam 302 consists of a vane 304 that is a component of a body 306 of head member 314. The vane 304 protrudes perpendicular to an axis of a pivot moment 308 of head member 314. A locking/latching ramp 310 protrudes from a lateral surface of the vane 304. The closed, storage state proximal edge of the ramp 310 starts on level with the lateral surface of the vane 304. The locking/latching ramp 310 rises on an incline distally in closed storage state until terminating in a vertical, steep drop off with a closed, storage state distal surface perpendicular to the lateral surface of the vane 304. The locking ramp 310 is aligned so it engages with a catch 312 when a head member 314 is pivoted to full open, testing position as seen in FIG. 26B.

FIGS. 27A-27D show a schematic of the locking/latching cam 302 mechanism relative to the catch 312 mechanism during the pivoting of the head member 314 between closed, storage position and open, testing position. The geometry and function of the components of the locking/latching cam 302 and catch 312 are more clearly seen in FIGS. 27A-27D As the locking/latching ramp 310 engages with the catch 312, the catch 312 rides up the locking/latching ramp 310 as the head member 314 continues to pivot. The catch 312 is mounted on a leaf/flat spring 316. The leaf spring 316 is only under tension while the catch 312 is on the locking/latching ramp 310. When the locking cam 302 is pivoted into full open, testing position, the catch 312 falls off the closed, storage state distal edge of the locking/latching ramp 310 and engages against the closed, storage state distal vertical edge of the locking/latching ramp 310, thus locking/latching the head member 314 in open, testing position.

Figure 27A:
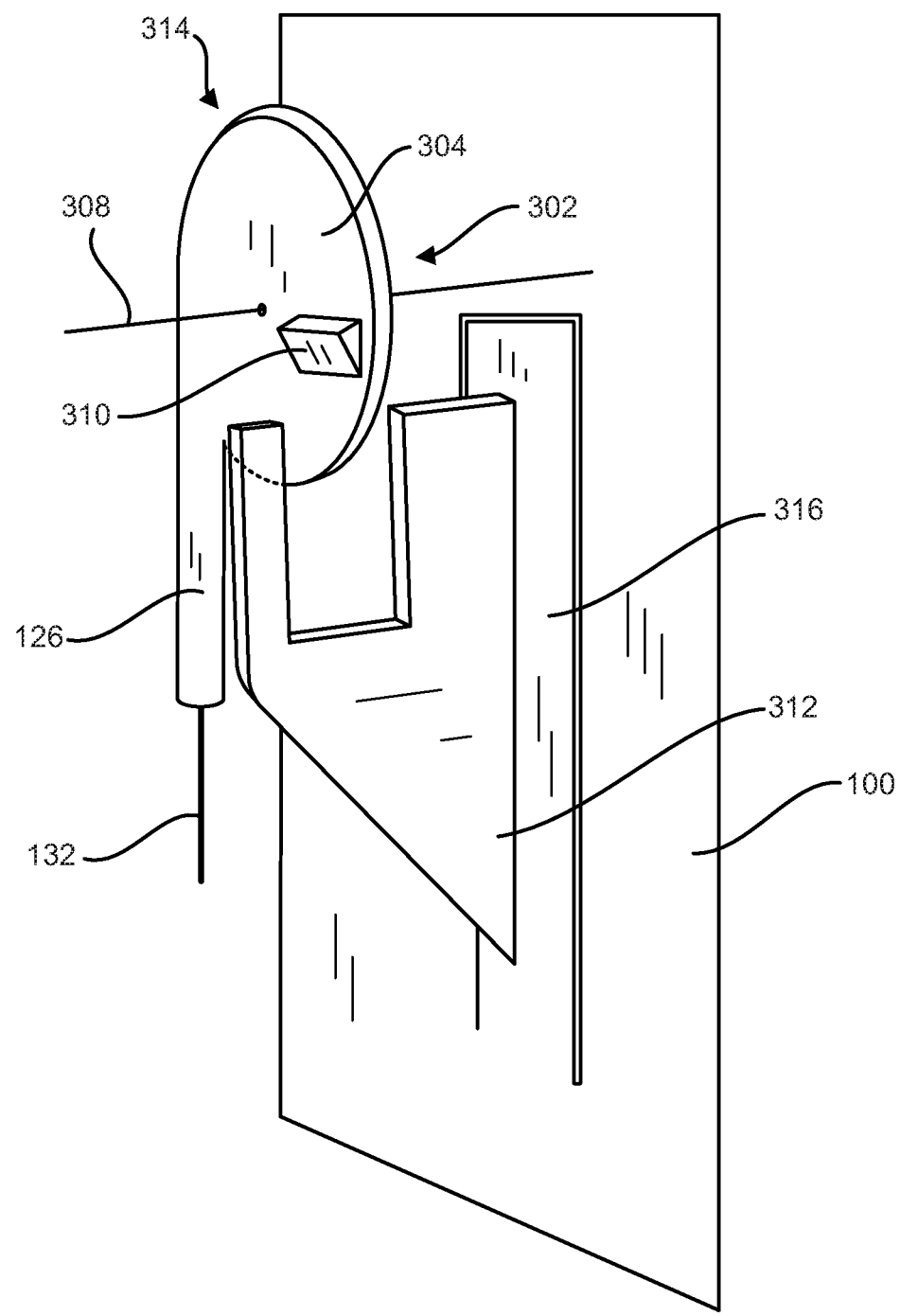
FIGS. 27A to 27D show the function in schematic perspective views of the locking/latching can and leaf spring mechanism in the fifth embodiment as it is rotated/pivoted in use.
Figure 27B:
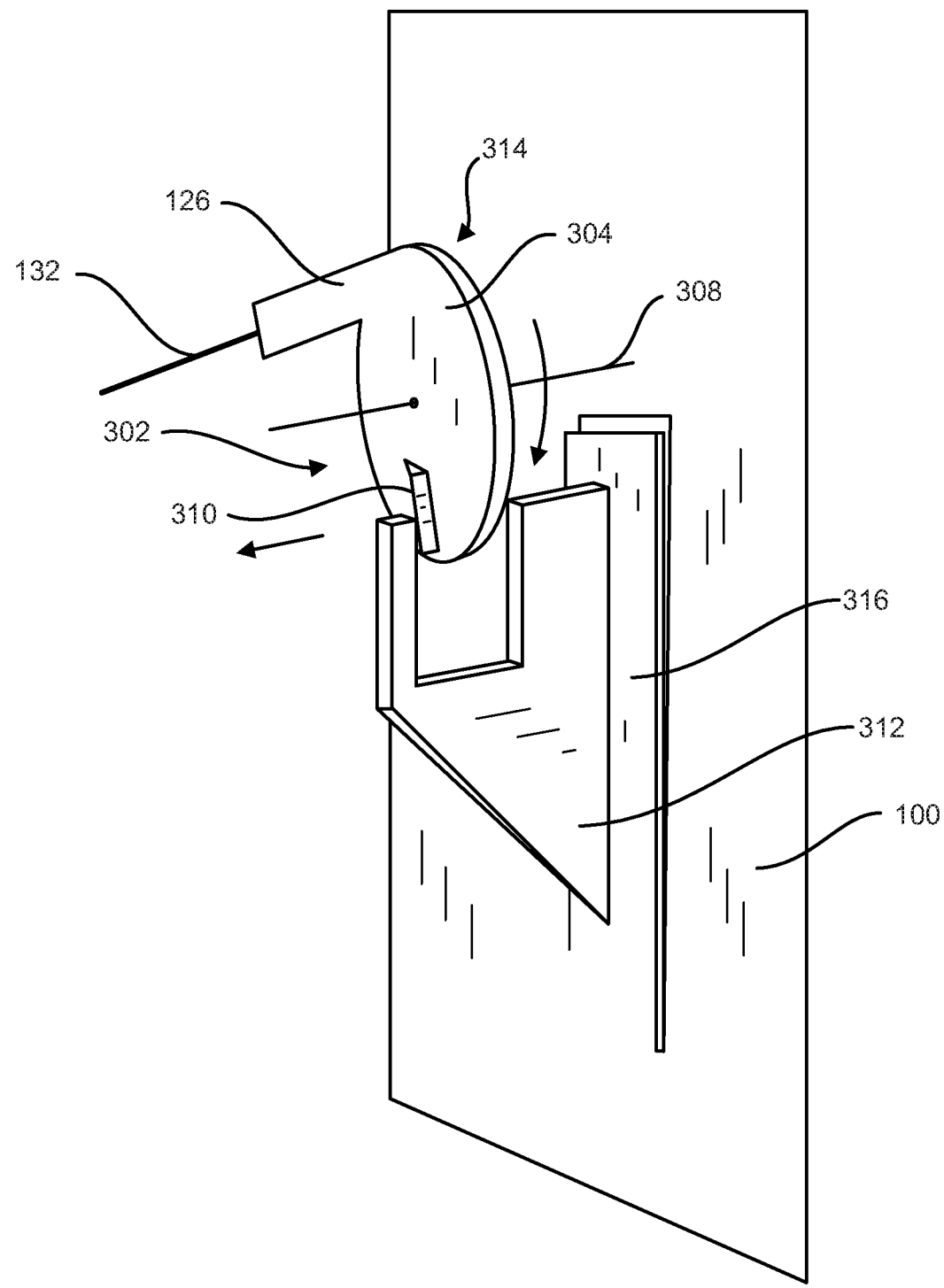

When the head member 314 is latched into open, testing position, this position is maintained by the leaf spring 316 exerting a force to hold the catch 312 against the vane 304 behind the closed, storage state distal vertical edge of the locking/latching ramp 310. The rotary force exerted on the head member 314 by the tension spring 300 favors the closed storage position. This rotary force also helps to maintain the catch 312 against the closed, storage state distal vertical edge of the locking/latching ramp 310 when the head member 314 is latched into open testing position. FIG. 27B shows the catch 312 riding up the locking/latching ramp 310 as the locking/latching cam 302 is rotated toward open testing position. The catch 312 pulls on the leaf spring 316 and deflects the leaf spring inward/deeper as it rides up the locking/latching ramp 310.

Figure 27C:
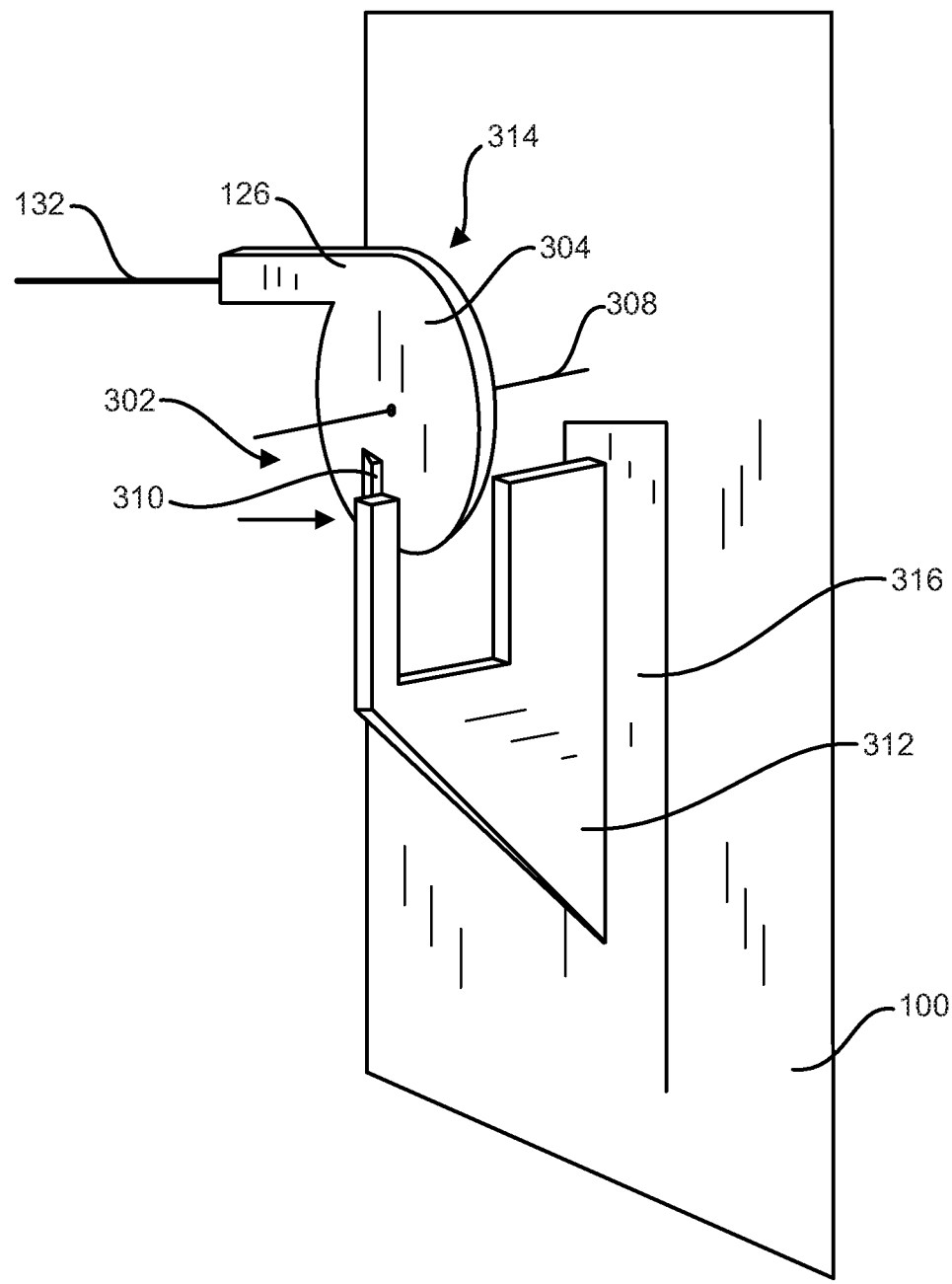
Figure 27D:
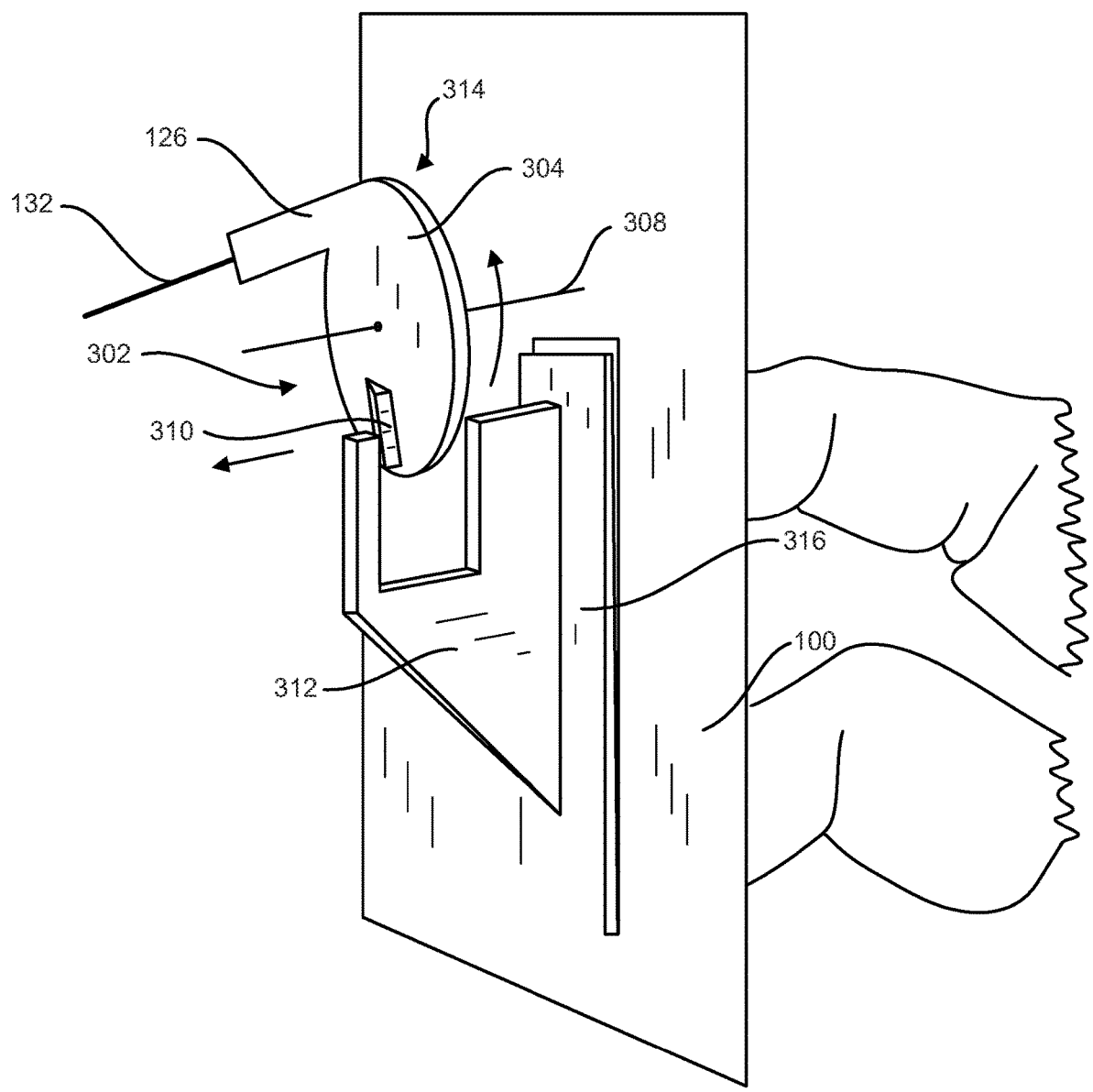

FIG. 27C shows the elastic force of the leaf spring 316 rebounding/recoiling outward to its resting position, thus pulling the catch 312 behind the locking ramp 310 and latching the locking/latching cam 302 into open testing position. To pivot the head member 314 back to closed storage position, the operator presses the leaf spring 316 inward to release the catch 312 when it clears the closed, storage state distal vertical edge of the locking/latching ramp 310 as shown in FIG. 27D. The rotary force on the head member 314 exerted by the tension spring 300 will then power assist the head member 314 automatically back to the closed storage position.

A variation of the fifth embodiment may lack the structures for the locking/latching mechanism. In this variation, the embodiment does not lock into the open, testing position. The open, testing position is maintained during testing by the operator maintaining the opening force with a finger retained on the activation lever 130. In this variation, the power assist mechanism will automatically close the embodiment once the opening force on the activation lever 130 is released by the operator.

Operation—FIGS. 26A-27D

This fifth embodiment is operated in the same fashion as the fourth embodiment and has the same advantages of increased filament security and simple, quick button-release to pivot the head member 314 back to closed, storage position with the leaf spring serving as a button.

6th Embodiment—FIGS. 28-31

Figure 28:
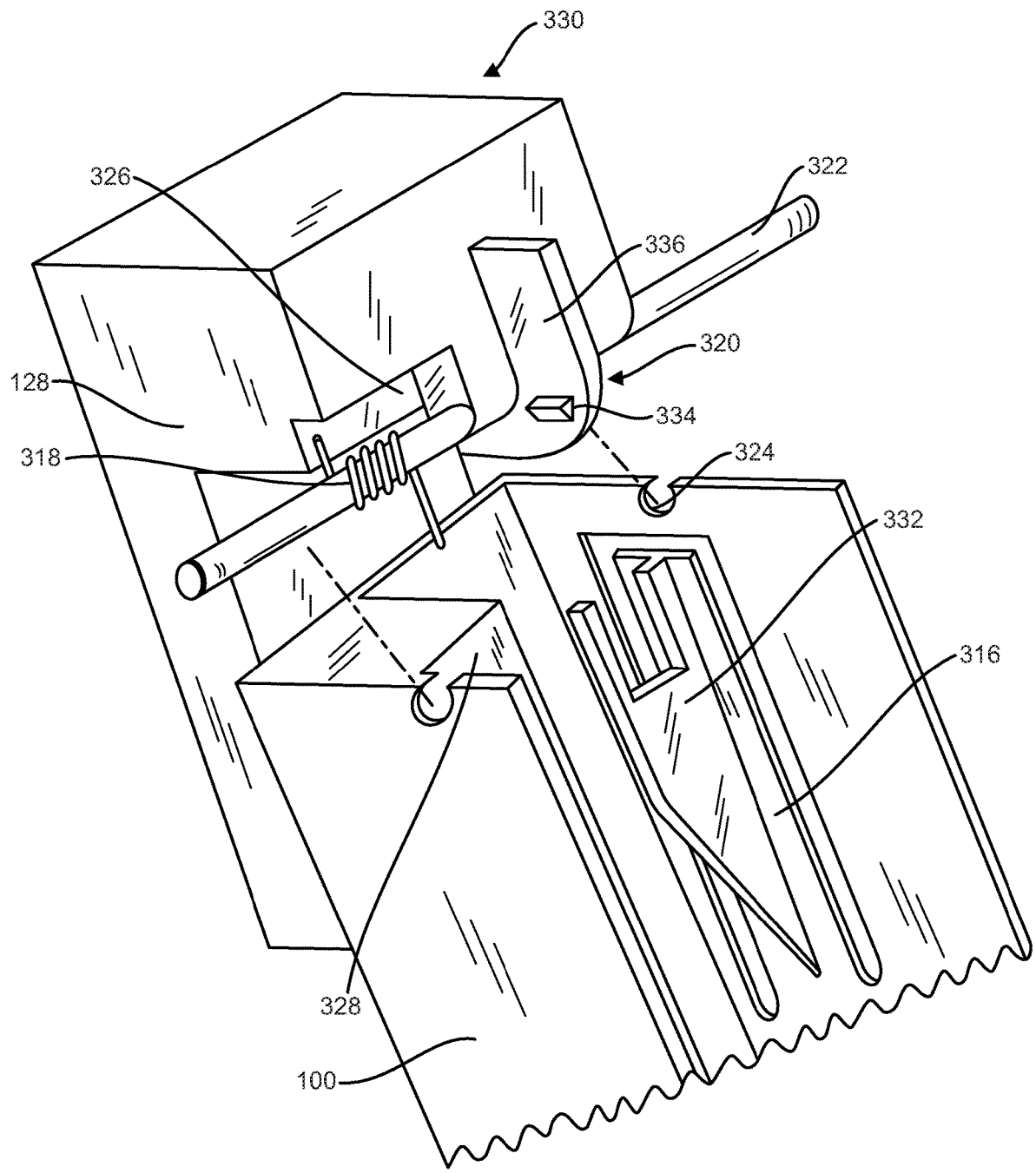
FIG. 28 shows a schematic perspective exploded partial view of the sixth embodiment in closed, storage position.
Figure 29:
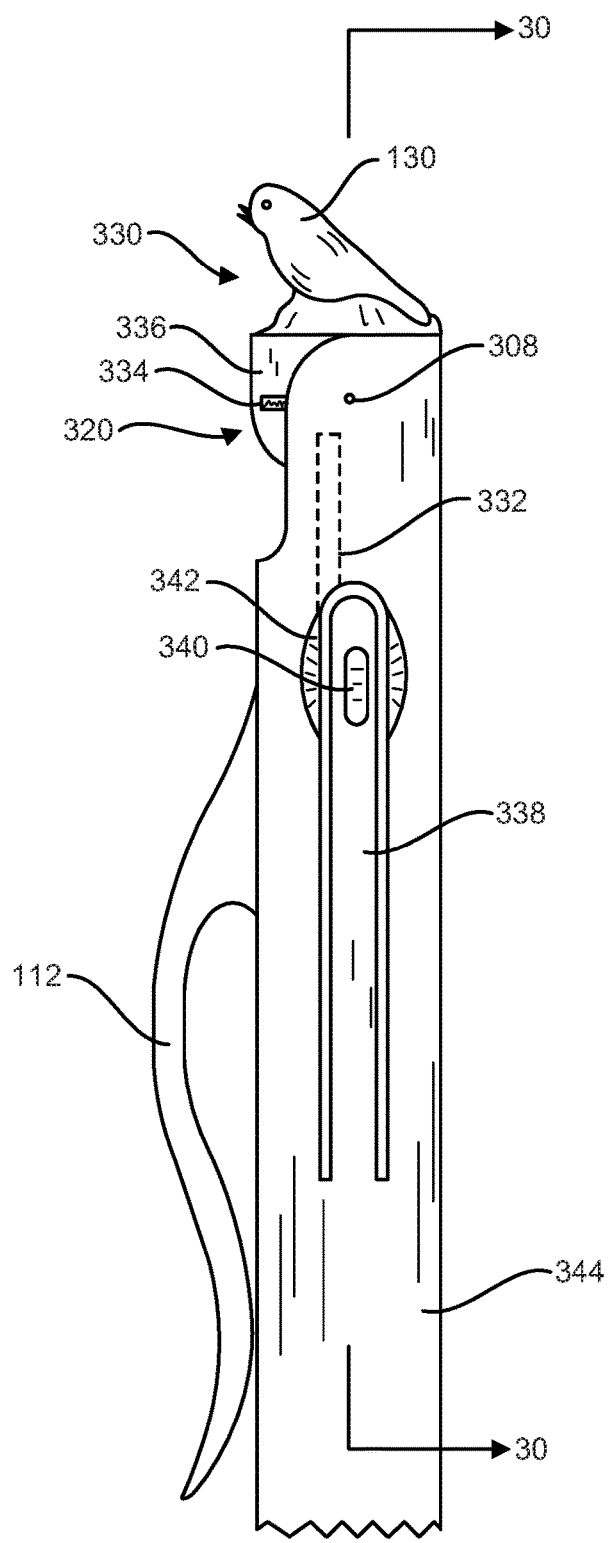
FIG. 29 shows a right lateral partial view of the sixth embodiment in closed, storage position.
Figure 30:
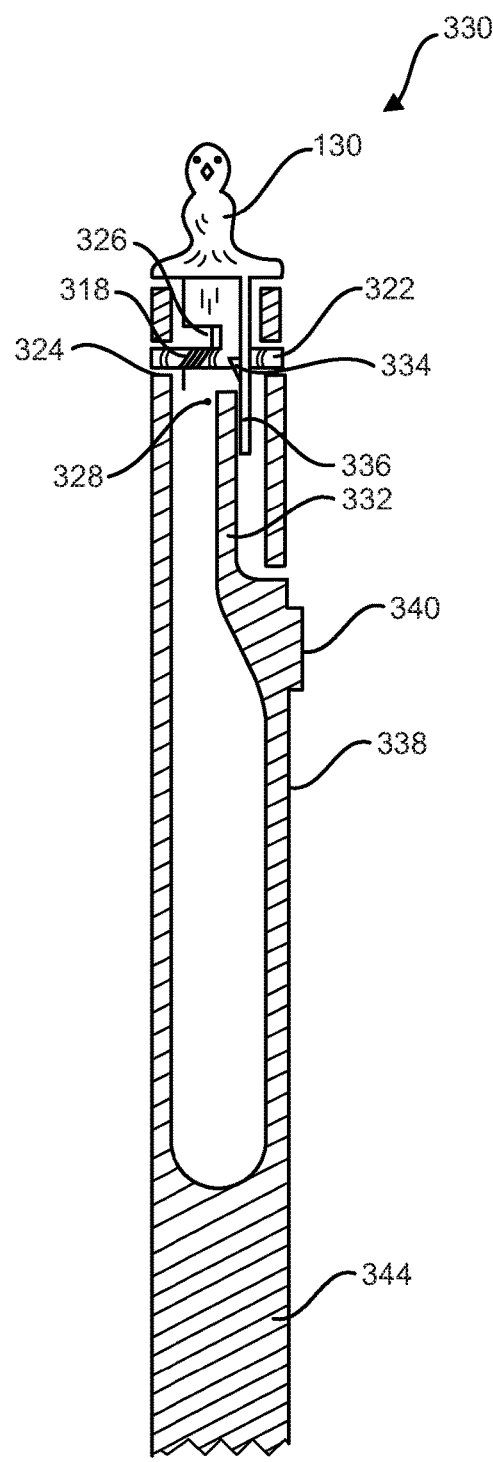
FIG. 30 shows a dorsal partial sectional partial view of the embodiment of FIG. 29 taken at sectioning plane indicated by section lines 30-30.

FIG. 28 shows a distal dorsal lateral exploded view of a schematic of a sixth embodiment that utilizes a torsion spring 318 and a latching (locking) cam 320. This embodiment is almost identical to the fifth embodiment other than the spring mechanism. This embodiment has a torsion spring 318 that threads over a section of an axle 322. The axle 322 can snap fit into an axle mounting hole 324 or have a fixed axle. One elongated free end of the torsion spring 318 abuts against a wall of an alcove 326 for spring counterforce in head member 330 while the other elongated free end of the torsion spring 318 abuts against a wall of an alcove 328 for spring 318 counterforce in handle member 100. The spring tension is aligned to force a head member 330 into closed, storage position. FIG. 29 shows a right lateral view of the sixth embodiment with dotted line/phantom representation of a catch 332 that cannot be seen from the surface in this view. FIG. 30 shows a dorsal partial sectional view of the sixth embodiment of FIG. 29 taken at the sectioning plane indicated by section lines 30-30. The catch/latch and release mechanism is composed of a latching (locking) ramp 334 on a vane 336 that interacts with the catch 332 mounted on a leaf spring 338.

Figure 31A:
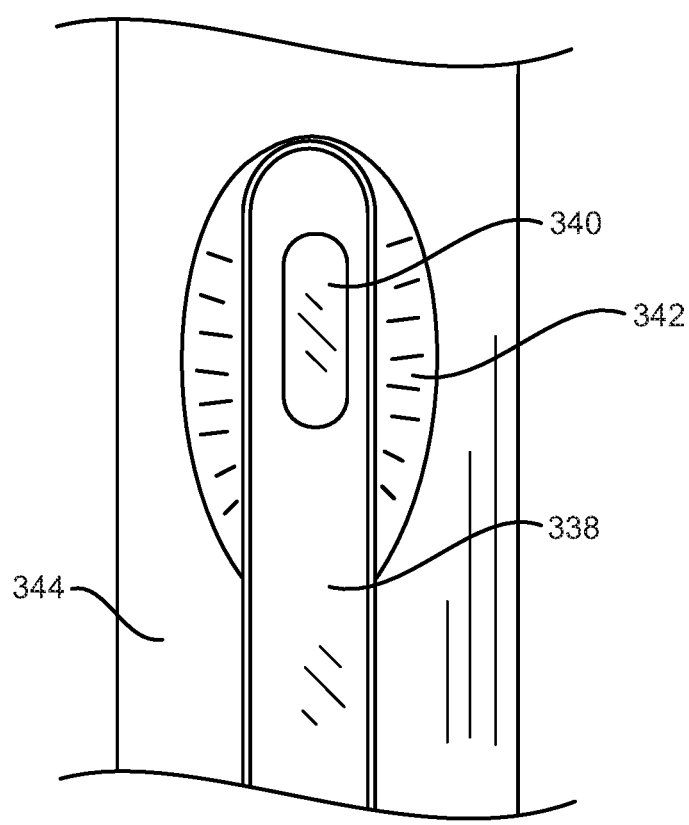
FIG. 31A shows a right lateral surface partial view of the leaf/flat spring and button of the fourth, fifth, and sixth embodiments.
Figure 31B:
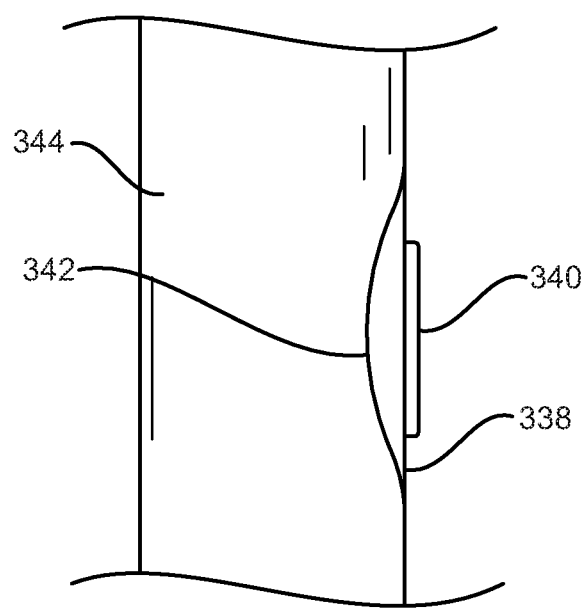
FIG. 31B shows a dorsal surface partial view of the leaf/flat spring and button of the fourth, fifth, and sixth embodiments.

FIG. 31A shows a lateral view of the leaf spring 338 and FIG. 31B shows a dorsal view. These two views show a button 340 protruding from the lateral surface of the leaf spring 338 near its free distal end. These two views also show a recess/dimple 342 in a body 344 of handle member 100 surrounding the free distal end of the leaf spring 338. The button 340 and the recess 342 assist the ability to press the leaf spring 338 inward to unlatch the latching (locking) cam 320 and have the head member 330 automatically power assist under spring force back to the closed, storage position.

A variation of the sixth embodiment may lack the structures for the locking/latching mechanism. In this variation, the embodiment does not lock into the open, testing position. The open, testing position is maintained during testing by the operator maintaining the opening force with a finger retained on the activation lever 130. In this variation, the power assist mechanism will automatically close the embodiment once the opening force on the activation lever 130 is released by the operator.

Operation

The operation of this sixth embodiment is identical to the operation of the fifth embodiment with all the same added advantages of increased filament protection and quick easy button-release to pivot the head member 330 back to closed, storage position.

Seventh Embodiment—FIGS. 32-37I

The seventh embodiment is shown in partially exploded perspective view in FIG. 32 and sectional views in FIGS. 33A,33B,37A-I. This embodiment utilizes a retractable cam mechanism 346 as in U.S. Pat. No. 3,288,115A shown schematically in FIGS. 33A and 33B.

The retractable cam mechanism 346 is coupled with a Scotch yoke mechanical linkage to translate the linear piston motion of a plunger 348 to a pivoting rotary motion of a filament arm 350.

The retractable cam mechanism 346 as used in modern retractable ballpoint writing pens is an already well known conventional element and in common use with several other variations (such as an angled tooth cam and follower mechanism, triangular tilting cam mechanism, etc.). With this embodiment, slightly more excursion of the retractable cam mechanism 346 may be needed than found in an average writing pen, but no more than commonly found in specialty pens such as retractable markers, etc.

Figure 33A:
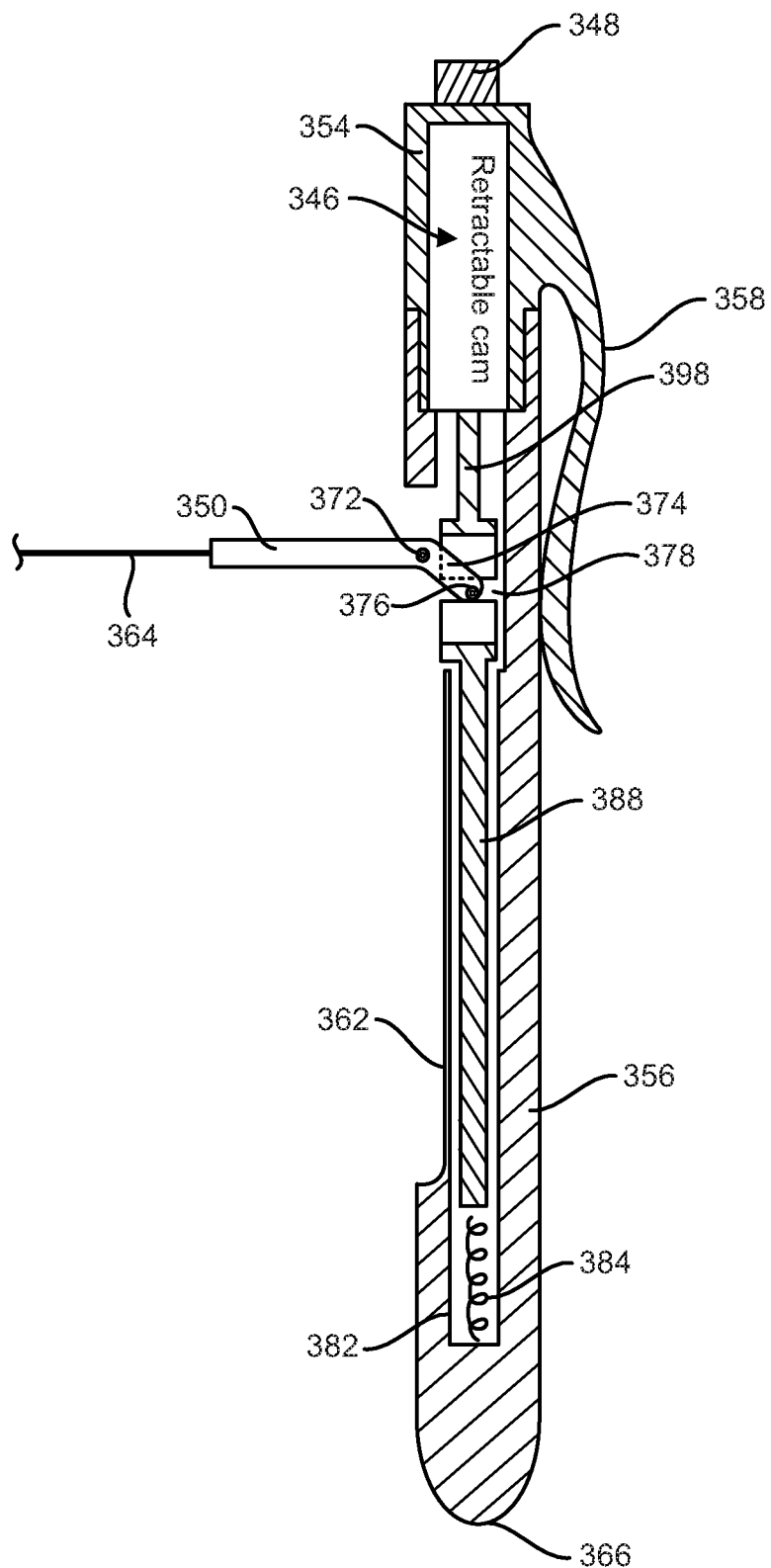
FIG. 33A shows a sectional view of the embodiment of FIG. 32 taken at the sectioning plane indicated by section lines 33-33 with the filament arm in open, testing position.
Figure 33B:
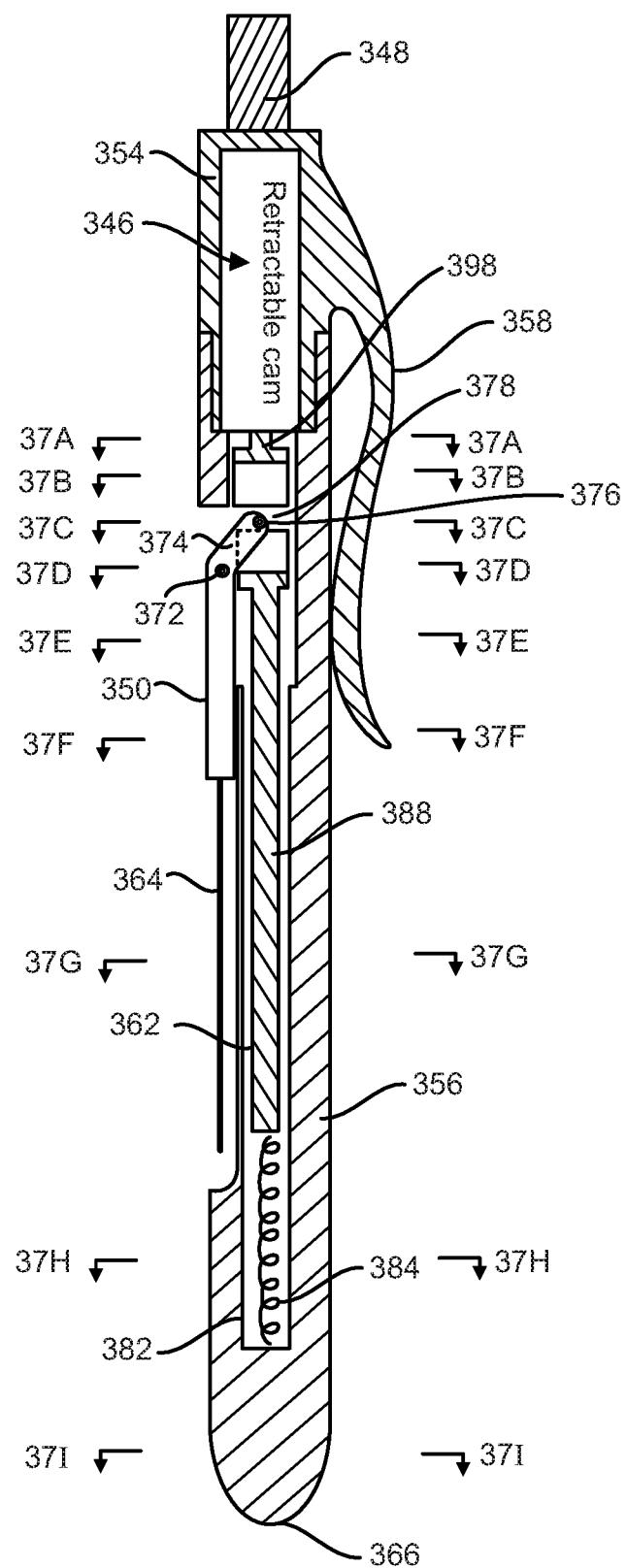
FIG. 33B shows a sectional view of the embodiment of FIG. 32 taken at the sectioning plane indicated by section lines 33-33 with the filament arm in closed, storage position.

FIG. 32 shows a partially exploded ventral lateral perspective view of the embodiment. FIG. 33A shows the embodiment of FIG. 32, in open testing position, taken at the sectioning plane indicated by section lines 33-33 of FIG. 32. FIG. 33B shows the same view as FIG. 33A, except the filament arm 350 is in closed storage position.

Figure 34:
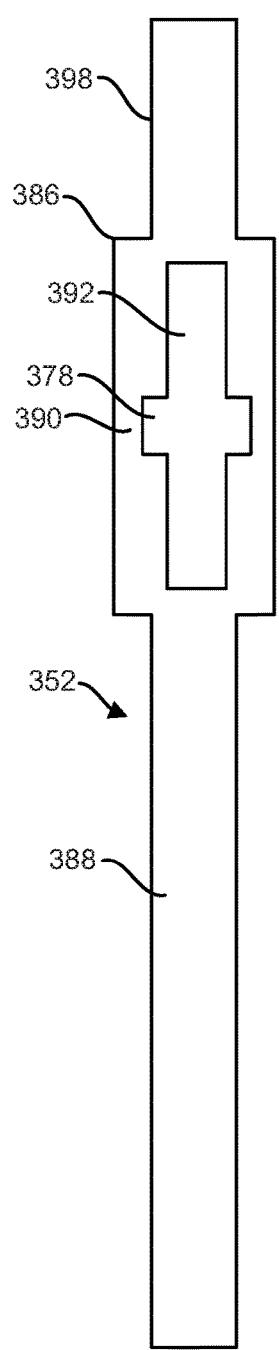
FIG. 34 shows a plan ventral view of the piston of the seventh embodiment.
Figure 35:
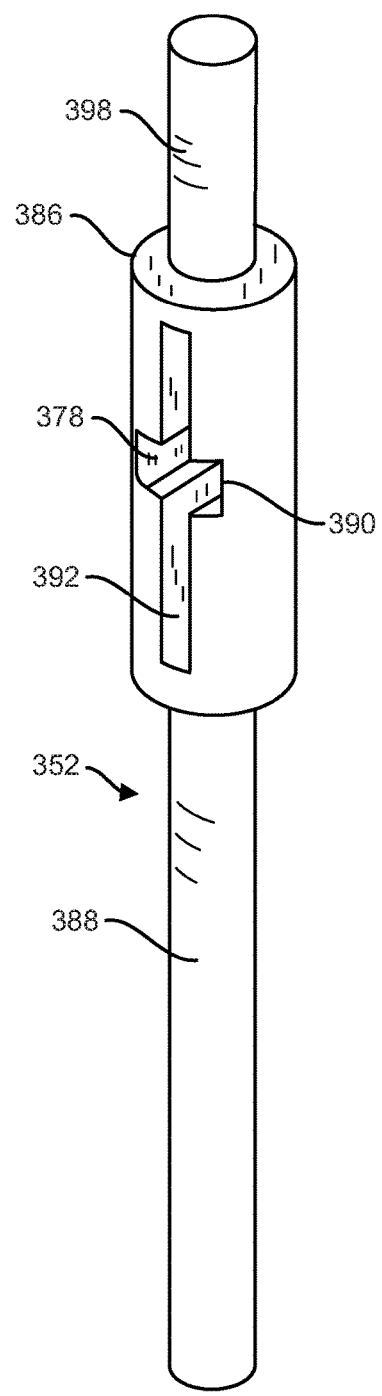
FIG. 35 shows a ventral left lateral distal perspective view of the piston of the seventh embodiment.
Figure 36:
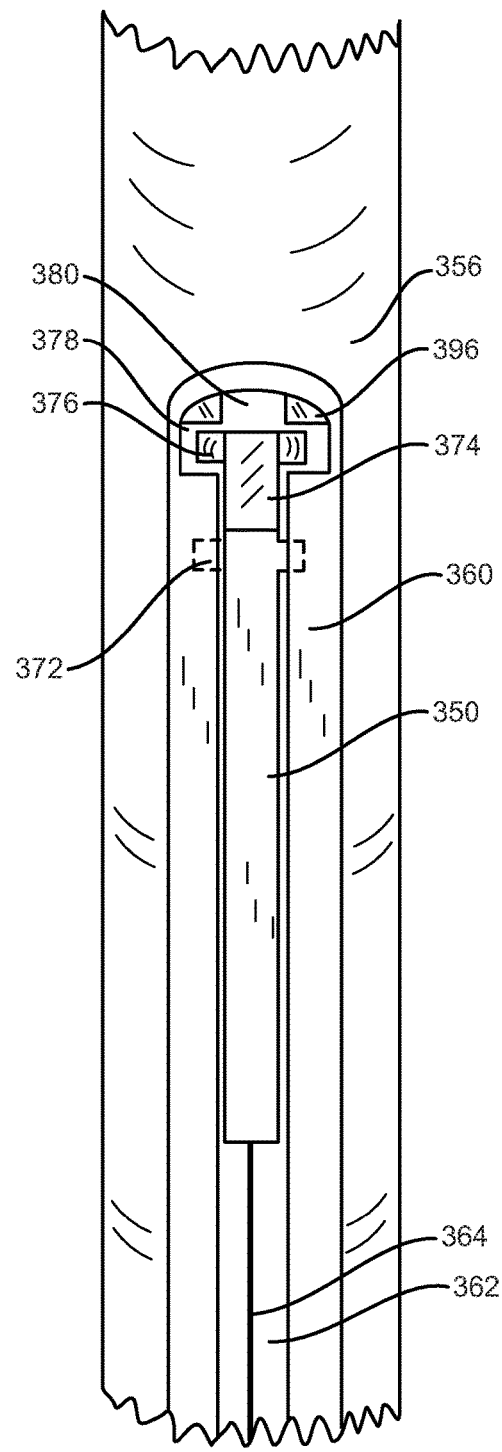
FIG. 36 shows a ventral partial view of the seventh embodiment in closed, storage position.

FIG. 33B also has sectional lines at levels 37A through 37I that represent the sectional planes of the sectional views in FIGS. 37A-37I. FIG. 34 shows a plan/profile ventral view of a piston 352 while FIG. 35 shows a ventral left lateral distal perspective partial view of the piston 352 isolated (removed) from the embodiment. FIG. 36 shows a ventral view of the assembled embodiment at the level of the filament arm 350 while in closed, storage position.

The embodiment has the plunger button 348 as in a modern retractable ballpoint pen and is seen in FIGS. 32, 33A, 33B. There is a cap 354 that snap fits, screws on, glues on or is secured/fastened by other simple fashion to a handle member 356. A pocket clip 358 as in previous embodiments and similar to one on a writing pen is attached to, or formed with, the cap 354 as in FIGS. 33A and 33B. The pocket clip 358 may also be attached to, or formed with, the handle member 356 toward its distal end. The ventral surface of the handle member 356 has a channel lip 360 as seen in FIG. 32 that serves as a buttress to guard fingers from accidently covering a channel 362. A filament 364 could be damaged as it pivots in and out of the channel 362 if the filament 364 contacts the fingers grasping the embodiment.

The channel lip 360 is more critical in this embodiment than the others since the filament 364 protrudes from a more proximal level on the handle member 356. This level is approximately the same level as the operator's natural instinctive grasp used during operation of the embodiment when performing sensory testing.

This seventh embodiment also has a proximal end 366 of handle member 356 which can have any of the previously mentioned configurations.

Figure 37A:
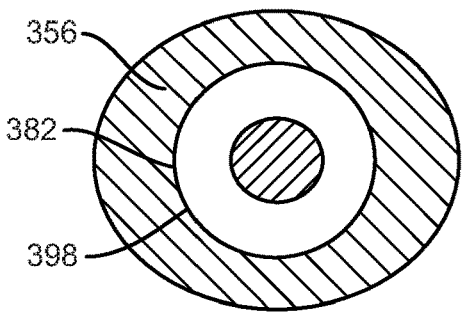
FIGS. 37A to 37I show multiple cross-sectional views of the embodiment of FIG. 33B taken at the sectioning planes indicated by section lines 37A-37A to 37I-37I.
Figure 37B:
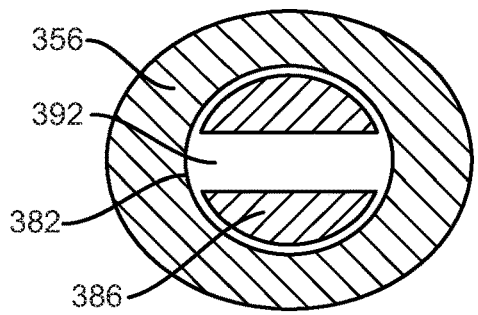
Figure 37C:
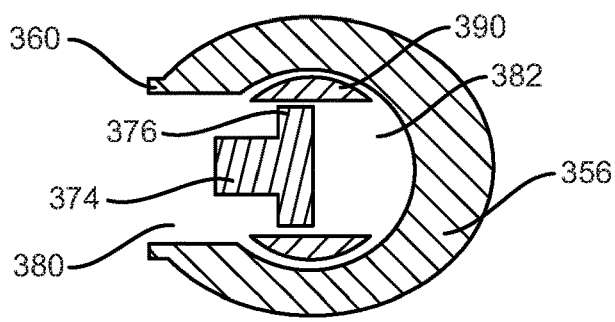
Figure 37D:
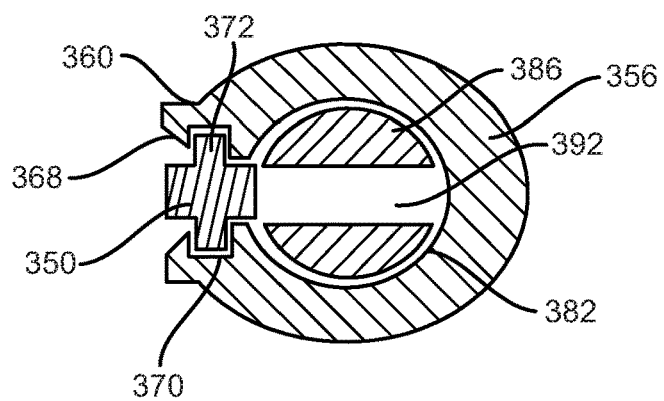
Figure 37E:
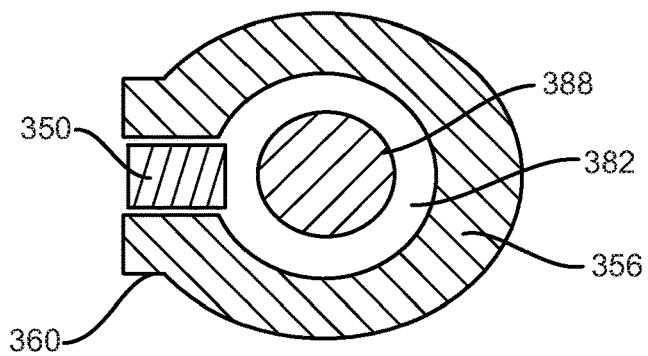
Figure 37F:
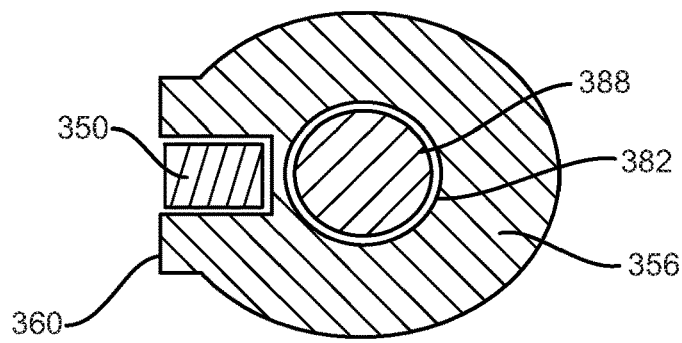
Figure 37G:
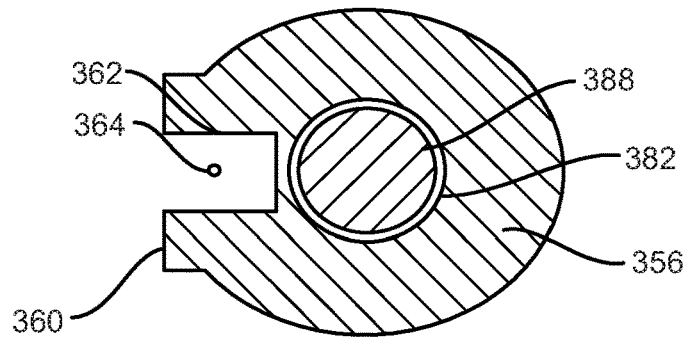
Figure 37H:
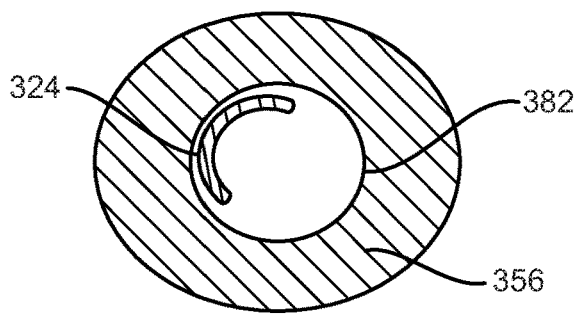
Figure 37I:
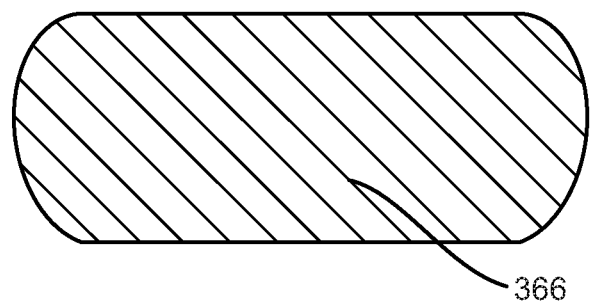

For reduced cost and ease of assembly, the filament arm 350 can be snap fit in place through the ventral surface via a bevel 368 to guide assembly of axle peg 372 into an axle mounting seat 370 in the channel lip 360 shown in FIG. 37D. A fixed axle could also be used. The axle mounting seat 370 mates with an axle peg 372 paired on each side where the filament arm 350 meets a lever 374 for Scotch yoke. At the free end of the lever 374 for Scotch yoke, there is a peg 376 for Scotch yoke in paired configuration as shown in FIGS. 32, 33A, 33B, 36, and 37C.

The peg 376 for Scotch yoke inserts into a slot 378 in piston 352 for Scotch yoke as shown in FIGS. 33A and 33B. During assembly, the pegs 376 for Scotch yoke can pass into the piston slot 378 through a window 380 for Scotch yoke assembly as shown in FIGS. 32, 36 and 37C.

A piston body 388 sits in a piston cylinder 382. A compression spring 384 sits in the piston cylinder 382 proximal to the piston body 388. FIGS. 34 and 35 show the piston 352 has an expansion 386 for Scotch yoke. The piston body 388 is proximal to the expansion 386 for Scotch yoke. The piston body 388 is slim/narrow enough to sit within the confines of the handle member 356 without communicating with the channel 362. The piston body 388 and the piston cylinder 382 have length that allows alignment of the piston 352 to be maintained throughout the full range of piston 352 excursion during normal use.

The materials of the piston 352 are stiff and have low friction against the cylinder.

The expansion 386 for Scotch yoke shown in FIGS. 34, 35, 37B-37D has sufficient diameter to allow for the piston slot 378 to be fashioned within it, while also allowing room for a lateral wall 390 of slot on each side to maintain the continuity and function of the piston 352. The expansion 386 for Scotch yoke also has a channel/slot 392 for excursion of lever 374 for Scotch yoke. The channel/slot 392 for excursion of lever 374 for Scotch yoke has sufficient dimensions that prevent abutment between the lever 374 for Scotch yoke and the piston 352 during their functional range of motion.

FIG. 36 shows the window 380 for Scotch yoke assembly on the ventral side of the handle member 356. The window 380 for Scotch yoke assembly is bordered by a bevel 396 to guide assembly of Scotch yoke shown in FIG. 36.

The window 380 for Scotch yoke assembly has dimensions to allow the pegs 376 for Scotch yoke to pass through. The window 380 is positioned at a level distal to the axle mounting seat 370 as shown in FIGS. 32, 36. The piston 352 has a shaft 398 from retractable cam mechanism 346 as seen in FIG. 33A, 33B, 34, 35, 37A.

The shaft 398 from retractable cam mechanism 346 links the motion of the retractable cam mechanism 346 to the piston 352.

Assembly of the seventh embodiment starts with the cap 354 removed from the handle member 356. From the open distal end of the handle member 356, the spring 384, followed by the piston body 388 are inserted into the piston cylinder 382. The cap 354 is put in place. The filament arm 350 is attached bypassing the pegs 376 for Scotch yoke through the window 380 for Scotch yoke assembly and into the piston slots 378. The axle pegs 372 are snap fit into the axle mounting seats 370.

A variation of the seventh embodiment may lack the retractable cam mechanism 346 but maintain the plunger 348, Scotch yoke, and spring 384 mechanism. In this variation, the power assist bias favors only the closed, storage position. The open, testing position is maintained by the operator retaining a finger on the depressed plunger 348 during testing. The variation closes automatically under power assist once the operator releases the depression on the plunger 348.

Operation of the seventh embodiment is similar to a modern retractable click ballpoint writing pen. The embodiment can be grasped and retrieved from a breast pocket, operated for testing, and returned to storage in a breast pocket, all without changing the initial retrieval grasp position. This maximizes the speed, efficiency and ease of testing.

The seventh embodiment is grasped in an identical manner as the first embodiment. The index finger of the operating hand depresses the plunger 348 which via the retractable cam mechanism 346 pushes the piston 352 to a biased position where the pegs 376 for Scotch yoke are proximal to the fulcrum formed by the axle pegs 372. This position leverages the filament arm 350 into full open, testing position that is held stable by the spring 384 force against the retractable cam mechanism 346 analogous to a retractable pen in deployed writing position. Another depression of the plunger 348 alternately retracts the piston 352 to another biased position where the pegs 376 for Scotch yoke are distal to the fulcrum formed by the axle pegs 372. This position leverages the filament arm 350 back into fill closed, storage position. Repeat depressions of the plunger 348 thus alternately positions the filament arm 350 between the biased open, testing position and the biased closed, storage position.

This seventh embodiment has several advantages. The embodiment looks fairly similar to a retractable ballpoint writing pen. The plunger mechanism of a ballpoint writing pen is very familiar to most operators and the deployment and storage by alternately pressing the plunger 348 is very intuitive. The retractable cam mechanism 346 is very reliable and proven by a long history of use in retractable writing pens. The distal mounted plunger 348 is unlikely to accidently depress and expose the filament 364 to potential damage. Another advantage is that the filament arm 350 will autocorrect to the chosen biased position with any depression of the plunger 348 that falls short of the fully depressed/clicked position.

DRAWINGS—REFERENCE NUMERALS 100 handle member
102 head member
104 body of handle member
106 channel
108 ventral surface of handle member
110 dorsal surface of handle member
112 pocket clip
114 proximal end of handle member
116 scraper tip
118 proximal end of head member
120 distal end of head member
122 ventral surface of head member
124 dorsal surface of head member
126 (filament) arm
128 body of head member
130 (activation) lever
132 (testing) filament
134 axle mounting hole
136 axle peg
138 retaining flange
140 distal end of handle member
142 flat tip
144 partial bevel tip
146 point
148 rounded tip
150 pivot moment
152 testing position contact surface
154 storage position contact surface
156 piston cylinder
158 spring
160 piston body
162 contact table (of piston)
164 bias corner
166 (filament mounting) bore
168 locking slider
170 slider body
172 slider locking flange
174 (slider) finger tab
176 slider shaft
178 body locking flange
180 ridge
182 gap
184 guard (for activation lever)
186 bridge
188 (handle member) cap extension
190 window (for filament arm protrusion)
192 window (for activation lever protrusion)
194 cap
196 exchangeable filament assembly
198 receiving shaft
200 spine (of receiving shaft)
202 bore (in exchangeable filament assembly)
204 dorsal ridge (of receiving shaft)
206 alignment slot
208 (shaft)locking flare/wedge
210 tip locking bevels
212 (shaft distraction) buttress
214 (tip distraction) buttress
216 exchangeable filament base
218 lateral receiving tip
220 (lateral surface) peg-in-hole arrangement
222 exchangeable filament base
224 receiving tip
226 bore
228 leaf spring
230 handle member
232 storage position contact surface
234 body of head member
236 head member
238 pivot moment
240 bias corner
242 testing position contact surface (of head member)
244 filament arm
246 recess
248 handle member
250 channel
252 (testing) filament
254 head member
256 handle member
258 (head member) bar magnet
260 (handle member) bar magnet
262 activation lever
264 axle flange
266 axle hole
268 axle peg
270 recess
272 pivot moment
274 head member
276 piston
278 leaf spring
280 locking button
282 hole
284 handle member
286 spring
288 cavity
290 cylinder
292 recess/dimple
294 peg
296 slot
298 filament
300 (tension) spring
302 locking/latching cam
304 vane
306 body of head member
308 pivot moment
310 locking/latching ramp
312 catch
314 head member
316 leaf spring
318 torsion spring
320 locking/latching cam
322 axle
324 axle mounting hole
326 alcove (head member)
328 alcove (handle member)
330 head member
332 catch
334 locking/latching ramp
336 vane
338 leaf spring
340 button 342 recess/dimple
344 body of handle member
346 retractable cam mechanism
348 plunger
350 filament arm
352 piston
354 cap
356 handle member
358 pocket clip
360 lip
362 channel
364 filament
366 proximal tip
368 bevel
370 axle mounting seat
372 axle peg
374 lever for Scotch yoke
376 peg for Scotch yoke
378 slot
380 window
382 cylinder
384 spring
386 expansion (for Scotch yoke)
388 piston body
390 lateral wall of slot
392 channel/slot (for lever for Scotch yoke)
396 bevel
398 shaft (from retractable cam mechanism)

What is claimed is:

1. A sensory testing device comprising:
a head member;
a filament connected to the head member;
a handle member;
a pivot connection between the handle member and the head member configured to provide a pivoting movement of the head member about an axis relative to the handle member between a storage position and a testing position; and
a biasing device comprising an non-electrical power assist mechanism to provide:
a storage biasing force acting in a storage biasing force application pivot range of the head member to bias the head member toward the storage position, with the head member within the storage biasing force application pivot range, wherein the storage biasing force must be overcome in the storage biasing force application pivot range for the pivoting movement of the head member in relation to the handle member about the axis of the pivoting connection out of the storage biasing force application pivot range toward the testing position; and
a testing biasing force acting in a testing biasing force application pivot range of the head member to bias the head member toward the testing position, with the head member within the testing biasing force application pivot range, wherein the testing biasing force must be overcome in the testing biasing force application pivot range for the pivoting movement of the head member in relation to the handle member about the axis of the pivoting connection out of the testing biasing force application pivot range toward the storage position, wherein the non-electrical power assist mechanism is configured such that the storage biasing force application pivot range overlaps with the testing biasing force application pivot range or the storage biasing force application pivot range is immediately adjacent to the testing biasing force application pivot range.

2. A sensory testing device in accordance with claim 1, wherein:
the filament is a part of a filament assembly, the filament assembly further comprising a filament base; and
the head member comprises a filament arm whereby the filament assembly is connectable to the filament arm and disconnectable from the filament arm to exchange the filament assembly with a replacement filament assembly.

3. A sensory testing device in accordance with claim 1, further comprising a sliding locking mechanism, wherein:
the head member comprises a filament arm; and
the sliding mechanism comprises a bolt lock portion that slides to lock the filament arm to the handle member to secure the filament in the storage position.

4. A sensory testing device in accordance with claim 1, wherein:
the head member comprises an activation lever arm extending laterally outward with respect to a longitudinal axis of the head member, the activation lever arm being engagable for pivoting the head member.

5. A sensory testing device in accordance with claim 4, further comprising a pocket clip connected to the handle member, wherein the pocket clip is on a same side of the sensory testing device as the activation lever arm, which is opposite to a side at which the filament, connected to the head member, pivots between the storage position and the testing position.

6. A sensory testing device in accordance with claim 4, wherein:
the handle member further comprises a distal extension guard limiting access to the activation lever arm at a longitudinal end of the handle member, thereby guarding the activation lever from an application of an unintentional pivoting force while the head member is in the storage position.

7. A sensory testing device in accordance with claim 1, wherein the head member comprises contact surfaces forming a part of the biasing device, the contact surfaces forming a squared off portion to define the testing position and the storage position.

8. A sensory testing device in accordance with claim 7, wherein the biasing device comprises:
a piston with a contact table at a top portion of the piston that makes contact with contact surfaces of the head member;
a piston cylinder located within the handle member, the piston being positioned in the piston cylinder; and
a spring located in the piston cylinder and below the piston exerting a spring force between the piston and the contact surfaces of the head member as well as allowing the piston to retract into the piston cylinder to allow the head member to rotate about the axis.

9. A sensory testing device in accordance with claim 1, wherein:
the handle member defines a channel; and
at least a portion of the filament is positioned in the channel to protect the filament with the head member in the storage position.

10. A sensory testing device in accordance with claim 9, wherein the channel is flanked by a channel lip thereby:
facilitating a proper grasp that does not cover the channel and interfere with motion of the filament into or out of the channel;
and facilitating a proper alignment of the handle member.

11. A sensory testing device in accordance with claim 1, wherein the handle member comprises a functional end, wherein the head member is at an opposite end from the functional end.

12. A sensory testing device in accordance with claim 1, wherein the head is removably connected to the handle by axle pins snap fit connected to the head member or snap fit connected to the handle member.

13. A sensory testing device in accordance with claim 1, wherein the biasing device comprises:
- a leaf spring supported by the handle member and axially aligned with the handle member, the spring member contacting contact surfaces of the head member to allow the head member to pivot about the axis.

14. A sensory testing device in accordance with claim 1, wherein the biasing device comprises:
- a magnet connected to the head member or the handle member;
- a magnetically attractive surface on the head member or the handle member that opposes the magnet whereby a magnetic force between the head member and the handle member provides the testing biasing force and the storage biasing force.

15. A sensory testing device in accordance with claim 1, wherein the biasing device comprises:
- a retractable cam mechanism;
- a Scotch yoke and a spring-loaded piston mechanism coupled with the retractable cam wherein there is a mechanical linkage to translate the linear piston motion of a retractable cam to a pivoting rotary motion of a filament arm.

16. A sensory testing device in accordance with claim 1, wherein:
- the handle member has a predetermined cross-sectional shape to facilitate a tactile alignment of the handle member with a hand of a user.

17. A sensory testing device comprising:
- a head member;
- a filament connected to the head member;
- a handle member;
- a pivot connection between the handle member and head member configured to provide a pivoting movement of the head member about a pivot axis relative to the handle member between a storage position and a testing position;
- and a biasing means applying a biasing force to the head member to bias the head member toward at least one of the storage position and the testing position, the biasing means having an application range acting over a full range of rotation of the pivoting movement between the storage position and the testing position;
- further comprising an activation lever arm connected to the head member, wherein:
- a longitudinal axis of the head member passes through the pivot axis;
- the activation lever arm extends laterally outward with respect to the longitudinal axis of the head member;
- the activation lever arm is engagable for pivoting the head member for pivoting movement of the head member about the pivot axis relative to the handle member between the storage position and the testing position;
- wherein the biasing force applied by the biasing means, in the application range, comprises:
- a storage biasing force acting in a storage biasing force application pivot range of the head member to bias the head member toward the storage position, with the head member within the storage biasing force application pivot range, wherein the storage biasing force must be overcome in the storage biasing force application pivot range for the pivoting movement of the head member in relation to the handle member about the axis of the pivoting connection out of the storage biasing force application pivot range toward the testing position;
- and a testing biasing force acting in a testing biasing force application pivot range of the head member to bias the head member toward the testing position, with the head member within the testing biasing force application pivot range, wherein the testing biasing force must be overcome in the testing biasing force application pivot range for the pivoting movement of the head member in relation to the handle member about the axis of the pivoting connection out of the testing biasing force application pivot range toward the storage position, wherein the storage biasing force application pivot range overlaps with the testing biasing force application pivot range or the storage biasing force application pivot range is immediately adjacent to the testing biasing force application pivot range.

18. A sensory testing device in accordance with claim 17, wherein the biasing device comprises:
- a Scotch yoke and a spring and latch piston mechanism translating the rotary motion with the pivoting movement of the head member to linear motion of the piston; and
- a locking button latch that protrudes from a hole in the handle member when the head member is pivoted into the testing position.

19. A sensory testing device in accordance with claim 17, wherein the biasing device comprises:
- a tension spring and a locking or latching cam;
- a vane that is a component of a body of the head member that protrudes perpendicular to the pivot axis moment; and
- a locking or latching ramp that protrudes from a lateral surface of the vane and is aligned so the locking or latching ramp engages with a catch when the head member is pivoted to the testing position.

20. A sensory testing device in accordance with claim 17, wherein the biasing device comprises:
- a torsion spring that threads over a section of an axle, said torsion spring is aligned to force a head member into closed storage position;
- a vane that is a component of a body of the head member that protrudes perpendicular to the pivot axis moment; and
- a locking or latching ramp that protrudes from a lateral surface of the vane and aligned so the locking or latching ramp engages with a catch when the head member is pivoted to the testing position.

* * * * *